US007693563B2

(12) United States Patent
Suresh et al.

(10) Patent No.: US 7,693,563 B2
(45) Date of Patent: Apr. 6, 2010

(54) METHOD FOR IMAGE PROCESSING AND CONTOUR ASSESSMENT OF THE HEART

(75) Inventors: Mitta Suresh, Richardson, TX (US); Jude Dalton, Nottingham (GB)

(73) Assignee: Chase Medical, LLP, Richardson, TX (US)

( * ) Notice: Subject to any disclaimer, the term of this patent is extended or adjusted under 35 U.S.C. 154(b) by 1656 days.

(21) Appl. No.: 10/769,745

(22) Filed: Jan. 30, 2004

(65) Prior Publication Data

US 2004/0153128 A1    Aug. 5, 2004

Related U.S. Application Data

(60) Provisional application No. 60/526,023, filed on Dec. 1, 2003.

(51) Int. Cl.
*A61B 5/05*      (2006.01)
(52) U.S. Cl. ........................ 600/407; 382/128
(58) Field of Classification Search ............. 600/439, 600/450, 416, 509, 508, 529, 407; 382/128; 128/661; 364/413.03
See application file for complete search history.

(56) References Cited

U.S. PATENT DOCUMENTS

| 4,352,988 A | 10/1982 | Ishida |
| 4,436,684 A | 3/1984 | White |
| 4,777,962 A * | 10/1988 | Watson et al. ............ 600/529 |
| 5,072,384 A | 12/1991 | Doi et al. |
| 5,151,856 A * | 9/1992 | Halmann et al. .......... 600/508 |
| 5,235,510 A | 8/1993 | Yamada et al. |
| 5,239,591 A | 8/1993 | Ranganath |
| 5,273,038 A | 12/1993 | Beavin |
| 5,319,551 A | 6/1994 | Sekiguchi et al. |
| 5,360,006 A | 11/1994 | Geiser et al. |
| 5,375,156 A | 12/1994 | Kuo Petravic et al. |

(Continued)

FOREIGN PATENT DOCUMENTS

WO     01/16886     3/2001

(Continued)

OTHER PUBLICATIONS

F. P. van Rugge et. al., "Magnetic Resonance Imaging during dobutamine Stress for detection and localization of coronary artery disease" *Circulation* 1994; 90, No. 1, pp. 127-138.

(Continued)

*Primary Examiner*—Brian Casler
*Assistant Examiner*—Jonathan G Cwern
(74) *Attorney, Agent, or Firm*—Meyertons, Hood, Kivlin, Kowert & Goetzel, P.C.; Eric B. Meyertons

(57) ABSTRACT

One embodiment discloses a computerized method of facilitating cardiac intervention. The method may include inputting patient data and creating a computerized interactive model of a heart based on the patient data. The model may include features. The model may simulate at least one proposed cardiac intervention by adding or deleting features to the model, and determining the effects of the proposed cardiac simulation upon the entire model. Simulations may be repeated to allow the user to determine an optimal cardiac intervention. A template and/or patient specific instrument may be created from the model to use as a guide during the cardiac intervention.

40 Claims, 56 Drawing Sheets

U.S. PATENT DOCUMENTS

| | | | |
|---|---|---|---|
| 5,433,199 A | 7/1995 | Cline et al. | |
| 5,435,310 A * | 7/1995 | Sheehan et al. | 600/416 |
| 5,450,850 A | 9/1995 | Iinuma | |
| 5,509,084 A | 4/1996 | Tanaka | |
| 5,533,085 A | 7/1996 | Sheehan et al. | |
| 5,559,901 A | 9/1996 | Lobregt | |
| 5,570,430 A | 10/1996 | Sheehan et al. | |
| 5,601,084 A * | 2/1997 | Sheehan et al. | 600/450 |
| 5,633,951 A | 5/1997 | Moshfeghi | |
| 5,684,398 A | 11/1997 | Takiguchi et al. | |
| 5,687,737 A | 11/1997 | Branham et al. | |
| 5,704,791 A | 1/1998 | Gillio | |
| 5,734,739 A | 3/1998 | Sheehan et al. | |
| 5,755,577 A | 5/1998 | Gillio | |
| 5,757,877 A | 5/1998 | Wilting | |
| 5,779,634 A | 7/1998 | Ema et al. | |
| 5,791,908 A | 8/1998 | Gillio | |
| 5,800,177 A | 9/1998 | Gillio | |
| 5,800,178 A | 9/1998 | Gillio | |
| 5,803,914 A | 9/1998 | Ryals et al. | |
| 5,807,256 A | 9/1998 | Taguchi et al. | |
| 5,817,022 A | 10/1998 | Vesely | |
| 5,839,440 A | 11/1998 | Liou et al. | |
| 5,889,524 A | 3/1999 | Sheehan et al. | |
| 5,892,515 A | 4/1999 | Kobayashi et al. | |
| 5,902,239 A | 5/1999 | Buurman | |
| 5,920,660 A | 7/1999 | Goto | |
| 5,923,770 A | 7/1999 | O'Donnell et al. | |
| 5,947,899 A | 9/1999 | Winslow et al. | |
| 5,954,648 A | 9/1999 | Van Der Brug | |
| 5,963,211 A | 10/1999 | Oikawa et al. | |
| 6,024,705 A | 2/2000 | Schlager et al. | |
| 6,045,512 A | 4/2000 | Roteliuk et al. | |
| 6,047,090 A | 4/2000 | Makram Ebeid | |
| 6,106,466 A | 8/2000 | Sheehan et al. | |
| 6,185,447 B1 | 2/2001 | Alley et al. | |
| 6,190,320 B1 | 2/2001 | Lelong | |
| 6,201,165 B1 | 3/2001 | Grant et al. | |
| 6,205,349 B1 | 3/2001 | Kim et al. | |
| 6,205,411 B1 | 3/2001 | DiGioia, III et al. | |
| 6,230,048 B1 | 5/2001 | Selvester et al. | |
| 6,241,699 B1 | 6/2001 | Suresh et al. | |
| 6,268,730 B1 | 7/2001 | Du | |
| 6,298,112 B1 | 10/2001 | Acharya et al. | |
| 6,315,735 B1 | 11/2001 | Joeken et al. | |
| 6,346,940 B1 | 2/2002 | Fukunaga | |
| 6,366,684 B1 | 4/2002 | Gerard et al. | |
| 6,373,920 B1 | 4/2002 | Hsieh | |
| 6,398,728 B1 | 6/2002 | Bardy | |
| 6,415,048 B1 | 7/2002 | Schneider | |
| 6,421,565 B1 | 7/2002 | Hemmingsson | |
| 6,438,403 B1 | 8/2002 | Cline et al. | |
| 6,442,417 B1 | 8/2002 | Shahidi et al. | |
| 6,445,183 B1 | 9/2002 | Shimizu et al. | |
| 6,447,453 B1 | 9/2002 | Roundhill et al. | |
| 6,447,454 B1 | 9/2002 | Chenal et al. | |
| 6,454,712 B1 | 9/2002 | Oonuki | |
| 6,454,776 B1 | 9/2002 | Tajima et al. | |
| 6,468,218 B1 | 10/2002 | Chen et al. | |
| 6,470,070 B2 | 10/2002 | Menhardt | |
| 6,473,488 B2 | 10/2002 | Menhardt | |
| 6,473,634 B1 | 10/2002 | Barni | |
| 6,482,146 B1 | 11/2002 | Alferness et al. | |
| 6,487,432 B2 | 11/2002 | Slack | |
| 6,493,571 B1 | 12/2002 | Bis et al. | |
| 6,496,560 B1 | 12/2002 | Lin et al. | |
| 6,510,337 B1 | 1/2003 | Heuscher et al. | |
| 6,522,324 B1 | 2/2003 | Bosma et al. | |
| 6,526,307 B2 | 2/2003 | Foo | |
| 6,535,623 B1 | 3/2003 | Tannenbaum et al. | |
| 6,545,678 B1 | 4/2003 | Ohazama | |
| 6,557,558 B1 | 5/2003 | Tajima et al. | |
| 6,559,641 B2 | 5/2003 | Thesen | |
| 6,563,941 B1 | 5/2003 | ODonnell et al. | |
| 6,573,717 B2 | 6/2003 | Thesen | |
| 6,574,304 B1 | 6/2003 | Hsieh et al. | |
| 6,587,541 B2 | 7/2003 | Menhardt | |
| 6,608,916 B1 | 8/2003 | Wei et al. | |
| 6,608,917 B1 | 8/2003 | Wei et al. | |
| 6,628,743 B1 | 9/2003 | Drummond et al. | |
| 6,801,643 B2 * | 10/2004 | Pieper | 382/128 |
| 7,136,540 B2 | 11/2006 | Kiyuna | |
| 7,327,862 B2 | 2/2008 | Murphy et al. | |
| 7,333,643 B2 | 2/2008 | Murphy et al. | |
| 2001/0012913 A1 | 8/2001 | Iliff | |
| 2001/0029333 A1 | 10/2001 | Shahidi | |
| 2001/0031919 A1 | 10/2001 | Strommer et al. | |
| 2001/0036245 A1 | 11/2001 | Kienzle, III et al. | |
| 2002/0016541 A1 | 2/2002 | Glossop | |
| 2002/0031204 A1 | 3/2002 | Vilsmeier | |
| 2002/0032377 A1 | 3/2002 | Thesen | |
| 2002/0035321 A1 | 3/2002 | Bucholz et al. | |
| 2002/0042566 A1 | 4/2002 | Matsuzaki et al. | |
| 2002/0070970 A1 | 6/2002 | Wood et al. | |
| 2002/0077540 A1 | 6/2002 | Kienzle, III | |
| 2002/0077541 A1 | 6/2002 | Kienzle, III | |
| 2002/0082498 A1 | 6/2002 | Wendt et al. | |
| 2002/0087075 A1 | 7/2002 | Bucholz | |
| 2002/0095313 A1 | 7/2002 | Haq | |
| 2002/0127523 A1 | 9/2002 | Edic et al. | |
| 2002/0167533 A1 | 11/2002 | Tirumalai et al. | |
| 2003/0000535 A1 | 1/2003 | Galloway, Jr. et al. | |
| 2003/0018251 A1 | 1/2003 | Solomon | |
| 2003/0038802 A1 | 2/2003 | Johnson et al. | |
| 2003/0069494 A1 | 4/2003 | Jolly | |
| 2003/0078494 A1 | 4/2003 | Panescu et al. | |
| 2003/0095697 A1 | 5/2003 | Wood et al. | |
| 2003/0114750 A1 | 6/2003 | Brock-Fisher et al. | |
| 2003/0187362 A1 | 10/2003 | Murphy et al. | |
| 2004/0015081 A1 * | 1/2004 | Kramer et al. | 600/439 |
| 2004/0049115 A1 | 3/2004 | Murphy et al. | |
| 2004/0049116 A1 | 3/2004 | Murphy et al. | |
| 2004/0176678 A1 | 9/2004 | Murphy et al. | |
| 2004/0176679 A1 | 9/2004 | Murphy et al. | |
| 2004/0193042 A1 | 9/2004 | Scampini et al. | |
| 2005/0020929 A1 * | 1/2005 | Murphy et al. | 600/509 |
| 2005/0043609 A1 | 2/2005 | Murphy et al. | |
| 2005/0203580 A1 * | 9/2005 | Prentice et al. | 607/9 |
| 2007/0014452 A1 | 1/2007 | Suresh et al. | |

FOREIGN PATENT DOCUMENTS

| | | |
|---|---|---|
| WO | 2004/068406 | 8/2004 |
| WO | 2004/070553 | 8/2004 |

OTHER PUBLICATIONS

Antman, Elliott M. et al., "Abciximab Facilitates the Rate and Extent of Thrombolysis—Results of the Thrombolysis in Myocardial Infarction (TIMI) 14 Trial", *Circulation*, Jun. 1, 1999, pp. 2720-2732.

Keegan, Jennifer et al., "Interleaved Spiral Cine Coronary Artery Velocity Mapping", *Magnetic Resonance in Medicine*, vol. 43, 2000, pp. 787-792.

Medina, R. et al., "Reconstruction of Three-Dimensional Shapes in Biplane Angiography: a Fuzzy and Evolutionary Approach", *Computers in Cardiology*, Hannover, Germany, Sep. 1999, 26, pp. 663-666.

Miles, K.A., "Measurement of tissue perfusion by dynamic computed tomography", *The British Journal of Radiology*, 1991, vol. 64, No. 761, pp. 409-412.

Mochizuki, Teruhito et al., "Demonstration of Acute Myocardial Infarction by Subsecond Spiral Computed Tomography-Early Defect and Delayed Enhancement", *Circulation*, 1999, 99, pp. 2058-2059.

Rumberger, John A. et al., "Use of Ultrafast Computed Tomography to Quantitate Regional Myocardial Perfusion: A Preliminary Report", *Journal of the American College of Cardiology*, vol. 9, No. 1, Jan. 1987, pp. 59-69.

J.M. Guccione et al., "Passive Material Properties of Intact Ventricular Myocardium Determined from a Cylindrical Model" *Journal of Biomechanical Engineering*, vol. 113, Feb. 1991.

K.D. Costa et al., "A Three-Dimensional Finite Element Method for Large Elastic Deformations of Ventricular Myocardium: I-Cylindrical and Spherical Polar Coordinates" *Journal of Biomechanical Engineering*, Nov. 1996, vol. 118, pp. 452-463.

P.J. Hunter et al., "Modeling the mechanical properties of cardiac muscle" *Progress in Biophysics & Molecular Biology*, 69 (1998) pp. 289-331.

R. Mazhari et al., "Integrative Models for Understanding the Structural Basis of Regional Mechanical Dysfunction in Ischemic Myocardium" *Annals of Biomedical Engineering*, 2000, vol. 28, pp. 979-990.

Hurst et al., "Hurst's The Heart, Arteries and Veins, 9th Edition" McGraw-Hill, 1998, Chapters 18-20, pp. 623-684.

Y. Sun et al., "A comprehensive model for right-left heart interaction under the influence of pericardium and baroreflex" *The American Journal of Physiology*, 1997, pp. H1499-H1515.

Malchijani, V. B. et al., "Three-dimensional coupled fluid—Structure simulation of pericardial bioprosthetic aortic valve function" *ASAIO Journal*, 1997, 43:M387-M392.

Olszewski, M. E., "Segmentation of Cardiac Magnetic Resonance Images Using Multidimensional Active Appearance Models", Department of Electrical and Computer Engineering, The University of Iowa, Apr. 2001.

Patel, N. C. et al., "Neurological Outcomes in Coronary Surgery: Independent Effect of Avoiding Cardiopulmonary Bypass" *Ann. Thorac. Surg.* 2002;74:400-6, Presented at the 38th Annual Meeting of The Society of Thoracic Surgeons, Fort Lauderdale, FL, Jan 28-30, 2002.

F.H. Sheehan et. al., "Advantages and applications of the centerline method for characterizing regional ventricular function" *Circulation* 1986; 74, No. 2, pp. 293-305.

Imamaki, M. et. al., "Prediction of improvement in regional left ventricular function after coronary artery bypass grafting: quantitative stress-redistribution $^{201}$ Tl imaging in detection of myocardial viability" *J. Cardiovascular Surg.* Oct. 2002; vol. 43, No. 5: pp. 603-607.

E. R. Holman et. al., "Detection and Quantification of Dysfunctional Myocardium by Magnetic Resonance Imaging" *Circulation* 1997; vol. 95, No. 4; pp. 924-931.

van der Geest, Rob J. et al., "Comparison Between Manual and Semiautomated Analysis of Left Ventricular Volume Parameters from Short-Axis MR Images", Journal of Computer Assisted Tomography, vol. 21, No. 5, 1997, pp. 756-765.

Weiss, Robert M. et al., "Evaluation of Cardiovascular Structure and Function with Electron-Beam Computed Tomography", Marcus Cardiac Imaging, 1996, vol. 2, Chapt. 53: 820-828.

Dai, Xiaolong et al., "Left-Ventricle Boundary Detection from Nuclear Medicine Images", (http://www4.ncsu.edu/eos/users/w/wes/homepage/daiHTML/cmrg_JDI.fm3.html#FN1) Journal of Digital Imaging, vol. 11, No. 1, Feb. 1998.

Di Donato, M. et al. "Regional Myocardial performance of non-ischaemic zones remote from anterior wall left ventricular aneurysm—Effects of aneurysmectomy", European Heart Journal, (1995) 16, 1285-1292.

T.F. Cootes and C. J. Taylor, "Statistical Models of Appearance for Computer Vision" Jul. 10, 2000 http://cvl.umiacs.umd.edu/users/nanda/Academics/Academic.html.

Cootes, T. F. et al., "Constrained Active Appearance Models" (http://citeseer.nj.nec.com/cache/papers/cs/22292/http:zSzzSzwww.wiau.man.ac.ukzSz~bimzSzPaperszSziccv2001.pdf/cootes01constrained.pdf) Proc. Int. Conf. on Computer Vision 2001, vol. I, pp. 748-754, 2001.

nerac.com "tech track: cardiac MRI", Question No. 1193837.005, Apr. 11, 2003.

U.S. Appl. No. 10/135,465, filed Apr. 30, 2002, Murphy et al.
U.S. Appl. No. 10/800,461, filed Mar. 15, 2004, Murphy et al.
U.S. Appl. No. 10/800,433, filed Mar. 15, 2004, Murphy et al.
U.S. Appl. No. 10/768,403, filed Jan. 30, 2004, Murphy et al.
U.S. Patent Application entitled A System and Method for Facilitating Cardiac Intervention, Jan. 30, 2004, Murphy et al.

nerac.com "tech track: Florence H Sheehan", Question No. 1199989.005, Feb. 28, 2003.

nerac.com "RetroSearch: Active Appearance Models", Question No. 1199989.009, Sep. 15, 2003.

nerac.com "tech track: cardiac MRI", Question No. 1193837.005, Apr. 12, 2003.

International Search Report and Written Opinion for PCT/US04/02604 mailed Oct. 6, 2004.

International Preliminary Examination Report for PCT /US04/02604 mailed Dec. 21, 2004.

International Search Report and Written Opinion for PCT/US04/02669 mailed Feb. 3, 2005.

Written Opinion for PCT/US04/02669 mailed Feb. 3, 2005.

Kim, R. J. et al. "The Use of Contrast-Enhanced Magnetic Resonance Imaging to Identify Reversible Myocardial Dysfunction" The New England Journal of Medicine, vol. 343, No. 20, Nov. 16, 2000, 1445-1452.

McEachen II, J. C. et al. "Shape-Based Tracking of Left Ventricular Wall Motion" IEEE Transactions on Medical Imaging, vol. 16, No. 3, Jun. 1997, 270-283.

Chalana, V. et al. "A Multiple Active Contour Model for Cardiac Boundary Detection on Echocardiographic Sequences" IEEE Transactions on Medical Imaging, vol. 15, No. 3, Jun. 1996, 290-298.

Setarehdan, S. K. et al. "Automatic Left Ventricular Feature Extraction and Visualisation from Echocardiographic Images" Computers in Cardiology 1996, 9-12.

Jacob G. et al. "Robust Contour Tracking in Echocardiographic Sequences" 6th International Conference on Computer Vision. ICCV '98 Bombay, Jan. 4-7, 1998 IEEE International Conference on Computer Vision, New York, NY: IEEE, US, Jan. 4, 1998, pp. 408-413.

Office Action for U.S. Appl. No. 10/135,465 mailed on Jul. 17, 2006, available in PAIR.

Office Action for U.S. Appl. No. 10/135,465 mailed on Feb. 21, 2007, availabe in PAIR.

Notice of Allowance for U.S. Appl. No. 10/135,465 mailed on Sep. 13, 2007, available in PAIR.

Office Action for U.S. Appl. No. 10/354,884 mailed on Nov. 1, 2006, available in PAIR.

Office Action for U.S. Appl. No. 10/354,884 mailed on Nov. 1, 2006, available in PAIR.

Office Action for U.S. Appl. No. 10/354,884 mailed on Jul. 19, 2007, available in PAIR.

Office Action for U.S. Appl. No. 10/713,911 mailed on Aug. 23, 2007, available in PAIR.

Office Action for U.S. Appl. No. 10/768,403 mailed on Mar. 6, 2007, available in PAIR.

Notice of Allowance for U.S. Appl. No. 10/768,403 mailed on Sep. 21, 2007, available in PAIR.

Supplemental Search Report for PCT/US04/02604 mailed Sep. 6, 2006.

* cited by examiner

WALL THICKNESS SYSTOLE
$d_s = CL_{SO} - CL_{SI}$

WALL THICKNESS DIASTOLE
$d_d = CL_{DO} - CL_{DI}$

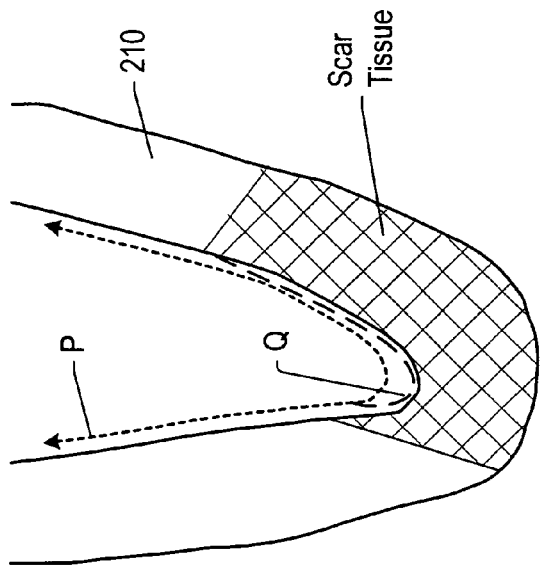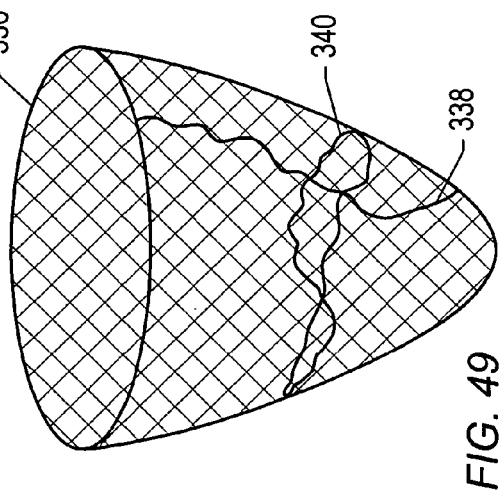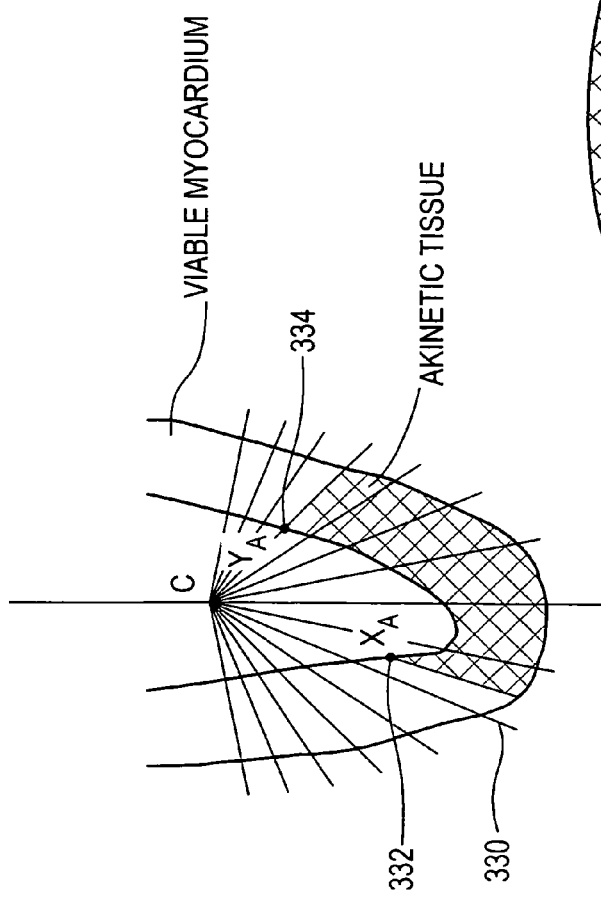
FIG. 48
FIG. 49
FIG. 47

$\varepsilon_x \neq \varepsilon_y$  $\varepsilon$ = Modulus Of Elasticity

| -1 | 0 | +1 |
|---|---|---|
| -2 | 0 | +2 |
| -1 | 0 | +1 |

Gx

| +1 | +2 | +1 |
|---|---|---|
| 0 | 0 | 0 |
| -1 | -2 | -1 |

| $I_{11}$ | $I_{12}$ | $I_{13}$ | $I_{14}$ | $I_{15}$ | $I_{16}$ | $I_{17}$ | $I_{18}$ | $I_{19}$ |
|---|---|---|---|---|---|---|---|---|
| $I_{21}$ | $I_{22}$ | $I_{23}$ | $I_{24}$ | $I_{25}$ | $I_{26}$ | $I_{27}$ | $I_{28}$ | $I_{29}$ |
| $I_{31}$ | $I_{32}$ | $I_{33}$ | $I_{34}$ | $I_{35}$ | $I_{36}$ | $I_{37}$ | $I_{38}$ | $I_{39}$ |
| $I_{41}$ | $I_{42}$ | $I_{43}$ | $I_{44}$ | $I_{45}$ | $I_{46}$ | $I_{47}$ | $I_{48}$ | $I_{49}$ |
| $I_{51}$ | $I_{52}$ | $I_{53}$ | $I_{54}$ | $I_{55}$ | $I_{56}$ | $I_{57}$ | $I_{58}$ | $I_{59}$ |
| $I_{61}$ | $I_{62}$ | $I_{63}$ | $I_{64}$ | $I_{65}$ | $I_{66}$ | $I_{67}$ | $I_{68}$ | $I_{69}$ |

| $K_{11}$ | $K_{12}$ | $K_{13}$ |
|---|---|---|
| $K_{21}$ | $K_{22}$ | $K_{23}$ |

FIG. 64

| $P_1$ | $P_2$ | $P_3$ |
|---|---|---|
| $P_4$ | $P_5$ | $P_6$ |
| $P_7$ | $P_8$ | $P_9$ |

FIG. 65

● Intersection short axis and long axis

● Centre located.

METHOD FOR IMAGE PROCESSING AND CONTOUR ASSESSMENT OF THE HEART

PRIORITY CLAIM

This application claims priority to U.S. application Ser. No. 10/713,911 entitled "SYSTEM AND METHOD FOR FACILITATING CARDIAC INTERVENTION" filed Jan. 30, 2003 and to U.S. Provisional Patent Application No. 60/526,023 entitled "METHOD AND SYSTEM FOR IMAGE PROCESSING AND CONTOUR ASSESSMENT" filed Dec. 1, 2003.

RELATED PATENTS

This patent application incorporates by reference in its entirety U.S. patent application Ser. No. 10/135,465 entitled "A System and Method for Facilitating Cardiac Intervention," filed on Apr. 30, 2002.

BACKGROUND OF THE INVENTION

1. Field of the Invention

This invention relates generally to systems for identifying the features that contribute to the cardiac performance of an individual patient through the use of imaging methods, and in particular to a computerized system and method for facilitating and assessing cardiac intervention methods.

2. Description of the Related Art

The circulatory system of a human works as a closed system where the effects of one part of the system are felt by all other parts of the system. For example, if a person's blood pressure rises then there is a corresponding pressure decrease in the venous system, the decrease is much smaller than the increase in the arterial side because of the fact that venous vasculature is more compliant than the arterial vasculature. Within the circulatory system the key component is the heart. Any change to any component of the heart will have an effect felt throughout the entire system.

The primary function of a heart in an animal is to deliver life-supporting oxygenated blood to tissue throughout the body. This function is accomplished in four stages, each relating to a particular chamber of the heart. Initially, deoxygenated blood is received in the right auricle of the heart. This deoxygenated blood is pumped by the right ventricle of the heart to the lungs where the blood is oxygenated. The oxygenated blood is initially received in the left auricle of the heart and ultimately pumped by the left ventricle of the heart throughout the body. The left ventricular chamber of the heart is of particular importance in this process as it is responsible for pumping the oxygenated blood through the aortic valve and ultimately throughout the entire vascular system.

A myocardial infarction (i.e., a heart attack) may not affect two different people in the same manner. The extent of the damage due to an infarction is based on many factors, such as: location of the infarction, extent of collateral flow in the blockage area, health of the heart prior to infarction, etc. A person's unique damage will have a corresponding unique effect on his/her entire cardiac system. For example, the infarction damage in one patient may be isolated to a small section of the ventricle wall. In another person, the infarction may involve not only the ventricle wall but also the septum. In still another person, the infarction might involve the papillary muscles. Over time, these unique damages will cause the heart to respond in different ways in an attempt to keep the circulatory system operating optimally.

Various treatments are currently employed to repair, replace or mitigate the effects of damaged components of the heart. Some of these treatments involve grafting new arteries onto blocked arteries, repairing or replacing valves, reconstructing a dilated left ventricle, administering medication, or implanting mechanical devices. All these treatments apply standard repairs to unique problems with a minimum of analysis as to what the optimum intervention should involve. Typically, the current procedures do not involve analyzing the performance of the cardiac system after the treatment to see what effect the treatment has had on the entire system. For example, a patient with blocked arteries may undergo a standard treatment of placing 5-6 grafts on their heart due solely to a short visual inspection of angiographic films that show some stenosis of the arteries of the heart. No analysis is performed to see if placing 3-4 grafts will achieve the same perfusion of the myocardium as the 5-6 grafts. It is simply a situation where the user decides that more is better, which may not be true. Placing 5-6 grafts requires more surgical time, longer pump runs, and incisions into numerous areas of the body to recover the needed grafts. This increases morbidity to the patient and may contribute to death of the patient who may not tolerate the additional stress of a longer, more invasive procedure. On some patients, the extra grafts may be needed, since collateral flow, or flow from other arteries, is not sufficient to perfuse the entire myocardium. On other patients, the grafts may not be needed, since sufficient flows will be generated from fewer grafts. Currently, the user has no way of knowing if the total number of grafts that he put in was appropriate.

A similar procedure is used to place stents in a vessel. Stents are placed in vessels based on an assessment of blockage and ability to access the obstructed area. No method of analysis is performed to determine the effects of placing a stent, to analyze how many stents should be placed, and/or to determine if the placement of stents produces a better result than bypassing.

The current process for repairing and replacing valves relies heavily on the user's knowledge and intuition. There is no precise way to determine how much a valve or structural component needs to change or what the effect of that change will be. The current procedure for determining if the correct repair was made is to complete the repair, remove the patient from cardiopulmonary bypass, and let the heart start beating. When the heart's performance reaches a normal range, an echocardiography is taken of the valve to ensure that it is not regurgitant. If the repair left some regurgitation, then the patient must go back on cardiopulmonary bypass, the heart must be stopped again, reopened, and additional repair work must be performed. This checking procedure is repeated after the second repair to ensure that the procedure has been correctly done. This procedure subjects the patient to unnecessary risks by exposing them to longer than necessary bypass runs and reperfusion injuries each time the heart is weaned of cardioplegia. This procedure also takes up valuable operating room and staff time. This multiple repair scenario for valve procedures is typical for most patients. Additionally, this assessment method only assesses one factor related to the performance of the valve and ventricle regurgitation. A user may perform a procedure, which corrects the existing problem, but the procedure may create another problem or diminish the performance of the ventricle. The user has little, if any, way to know if he compromised ventricle performance, since current analytical tools only look for flow across the valve. It would be desirable to have available methods to identify and evaluate the positioning of the valve apparatus, the attached tissue, and their combined performance.

Similarly, it would be desirable to have improved methods to determine when to replace or repair a valve. Typically, this is left to the judgment of the user based on a review of two-dimensional echocardiography studies. Users who are unfamiliar with repair techniques may opt for replacement when repair is not only possible but also the best course of action for the patient. Typically, a valve replacement will be done without knowing what effect it will have on the other elements of the mitral valve apparatus, left ventricle, left atrium and the overall functioning of the heart. For example, a replacement that attaches the chordae tendinae to the new valve may have a much different effect on the ventricle than a replacement that excludes the chordae tendinae. It would be useful to have a method to assist the user in making this assessment. Repairs are typically undertaken to shorten the chordae and annulus without knowing what effect the repairs will have on the entire apparatus. The current solution is to make the repair and let the heart beat to see what the repair has done.

What is needed, therefore, is a reliable method and apparatus to allow a user to determine which elements of the heart are not contributing to, or are decrementing from, the performance of the heart. It is also desirable to have a method and apparatus to allow the user to simulate the treatment on a portion of those elements and see the effect the treatment has on the other elements and the heart as a whole prior to performing the surgery.

SUMMARY

In one embodiment, a computerized system and method of facilitating cardiac intervention is disclosed. A computerized method includes inputting patient data and creating a computerized interactive model of a diseased heart based on the patient data. The computerized interactive model may include at least one feature that simulates at least one proposed cardiac intervention treatment. A proposed cardiac intervention may be simulated by adding, deleting, and/or modifying at least one feature of the model. A simulation may include determining the effects of the proposed cardiac intervention upon the entire model. A simulation may be repeated to allow the user to determine an optimal cardiac intervention. Specific surgical procedures may be modeled using the methods outlined herein. Additionally, a template may be created from the model to use as a guide during the surgical procedure. Cardiac instruments may be designed from the model and/or images created. Cardiac instruments may include patient specific templates and/or patient specific instruments for use before, during, and/or after a cardiac intervention.

Some embodiments are directed to the preoperative analysis of a patient's heart condition and computer assisted manipulation of the patient's heart to simulate procedures. Procedures that may be simulated include, but are not limited to, coronary artery bypass grafting, stent placement, surgical ventricular repair, valve repair and replacement, and implantation of devices.

An embodiment of a method of diagnosing disease of a human heart may include providing one or more images of heart tissue from the heart to a computer system. A method may include comparing one feature of one image of the one or more images of heart tissue from the heart to one or more reference features in a database to assess a state of the heart. In some embodiments, a plurality of images may be provided to a computer system and an at least a three-dimensional model created from at least some of the images. A feature of the multi-dimensional model/image may be compared to a database of heart features. In other embodiments, a system may include a CPU. A system may include system memory coupled to the CPU. System memory may store one or more computer programs executable by the CPU. The computer programs may be executable to perform the method. In an embodiment, a carrier medium may store program instructions executable to carry out the method of diagnosing a disease in a heart. In some embodiments, a report for the diagnosis of the heart may be prepared.

In an embodiment, a method of assessing treatments for disease of a human heart may include providing at least one image of heart tissue from the heart to a computer system. An image may include a plurality of features. A first modification may be performed on at least one of the plurality of features. One or more second modifications may be performed on at least one of the plurality of features. The first modification may be compared to at least one of the second modifications. In some embodiments, a plurality of images may be included and an at least a three-dimensional model created from some of the images. An image of the results may be created by a computer system.

In an embodiment, a method of assessing surgical procedures for a human heart may include providing at least one image of heart tissue from the heart to a computer system. One or more features derived from the image may be modified. An affect of the modification may be assessed. An assessment may be carried out by a computer system. A modification of one or more features may be carried out by a computer system. In some embodiments, a plurality of images may be included and an at least three-dimensional model created from some of the images. An image of the results may be created by a computer system.

In an embodiment, a method of designing cardiac instruments may include providing at least one image of heart tissue from a human heart to a computer system. A method may include creating a pattern of at least a portion of at least one cardiac instrument using at least one image. In some embodiments, a plurality of images may be included and an at least three-dimensional model created from some of the images. An image of the results may be created by a computer system. Images created by a computer system of a design of a cardiac instrument may be used to assist in the manufacturing of the instrument.

In an embodiment, a method of determining a volume of a heart may include providing a plurality of images of at least a portion of the heart to a computer system. A method may include assessing a volume in the portion by using the computer system to assess areas on the image. In some embodiments, a plurality of images may be included and an at least three-dimensional model created from some of the images. An image of the results may be created by a computer system. In one embodiment, an end diastolic volume of a heart may be assessed by a computer system if at least one provided image depicts the heart in a substantially expanded condition. In one embodiment, an end systolic volume of a heart may be assessed by a computer system if at least one provided image depicts the heart in a substantially contracted condition.

In an embodiment, a method of determining an ejection fraction of a human heart, may include providing a plurality of images of heart tissue from the heart to a computer system. A method may include assessing at least a first volume and a second volume of a portion of a heart by using the computer system to assess areas on at least two of the images. The volumes may include at least one end diastolic volume and at least one end systolic volume. In some embodiments, a plurality of images may be included and an at least three-dimensional model created from some of the images. An image of the results may be created by a computer system.

In an embodiment, a method of assessing a viability of tissue in a human heart may include providing one or more images of tissue from the human heart to a computer system. A method may include assessing viability of the heart tissue by using the computer system to assess a contrast between two or more sections in at least one image. In some embodiments, a plurality of images may be included and an at least three-dimensional model created from some of the images. An image of the results may be created by a computer system. In some embodiments, a method of assessing a viability of tissue in a human heart may include providing at least one image of tissue from the heart to a computer system. The method may include dividing at least one image into a plurality of sections. The section may or may not be regular and/or evenly distributed. A value may be assigned to at least one of the sections. The value may be a function of a feature of the section. The value of at least one of the sections may be used to assess viability of the heart tissue in or proximate to at least one of the sections. A feature of the section may include the color of the feature. Color may include grayscale as well.

In some embodiments, a method to assess motion of tissue in a human heart may include providing a plurality of images of tissue from the heart to a computer system. The plurality of images may be used to create one or more three-dimensional images of the heart tissue. Motion of at least one section of the three-dimensional image may be assessed to assess asynergy of the heart tissue. One or more three-dimensional images of the assessed asynergy may be created by a computer system.

In an embodiment, a method to assess transmurality of scarring of tissue in a human heart may include providing at least one image of tissue from the heart to a computer system. An extent of heart tissue scarring may be assessed by using the computer system to assess a contrast between at least two sections in at least one image. One or more three-dimensional images of the assessed transmurality may be created by a computer system. Progressive coloring of the assessed transmurality may be used in the created image to display the extent of scarring.

In an embodiment, a method of assessing viability of human heart tissue may include providing at least one image of heart tissue from a human heart to a computer system. A wall thickness of the heart tissue may be assessed by using the computer system to assess a contrast between at least two sections in at least one image. One or more three-dimensional images of the assessed shape may be created by a computer system. Progressive coloring of the assessed wall thickness may be used in the created image to display the extent of tissue thin enough to be considered "dead" tissue.

In some embodiments, a method of assessing a mitral valve in a human heart may include providing at least one image of heart tissue from a human heart to a computer system. A state of a mitral valve in the heart may be assessed by using the computer system to assess one or more distances between two papillary muscles of the heart and/or one or more angles between a mitral valve and one or more papillary muscles. One or more at least three-dimensional images of the assessed condition of a mitral valve may be created by a computer system. In one embodiment, a distance between portions of a human heart may be assessed. The distance may be between two papillary muscles, a papillary muscle and a mitral valve, and/or a papillary muscle and another portion of a human heart. A method may include locating at least two reference points on at least one image of the heart tissue. One or more distances in the heart tissue may be assessed by using the computer system to assess a distance between a plurality of reference points. In one embodiment, images provided to a computer system may be used to assess angles in a human heart. Two or more reference lines and/or planes may be located in at least one image of human heart tissue. Reference lines may be used to assess one or more angles in a heart.

In an embodiment, a method of assessing blood flow in a human heart may include providing at least two images of heart tissue from the heart, a velocity of fluid through a portion of a human heart and a time frame over which the images were collected to the computer system. Fluid flow through a portion of a human heart may be assessed by using the computer system to assess areas on the images. One or more at least three-dimensional images of the assessed blood flow may be created by a computer system.

In some embodiments, a method of analyzing a shape of human heart tissue may include providing at least one image of heart tissue from a human heart to a computer system. At least one image may be divided into a plurality of sections. A shape of the heart tissue may be assessed by using the computer system to assess a curvature of at least one of the sections. One or more three-dimensional images of the assessed shape may be created by a computer system.

In an embodiment, a method of assessing mitral regurgitation in a human heart may include providing at least two images of heart tissue from a human heart and a velocity of blood as a function of time through a portion of the heart to a computer system. A mitral regurgitation of the heart may be assessed by using the computer system to assess at least a first and second volume of a portion of the heart and blood flow through a portion of the heart.

In some embodiments, a method of assessing a viability of human heart tissue may include providing at least two images of heart tissue from a human heart to a computer system. At least one reference point may be assigned to at least two images of the heart tissue. A viability of the heart tissue may be assessed by using the computer system to assess relative movement of at least one of the reference points between at least two images of the heart tissue. One or more three-dimensional images of the assessed viability may be created by a computer system. Progressive coloring of the assessed viability may be used in the created image to display the extent of nonviable tissue.

In an embodiment, a method of assessing heart reconstruction procedures may include providing at least one image of heart tissue from a human heart to a computer system. At least one of the images may include at least a portion of a mitral valve. At least one feature derived from the image may be modified. At least one of the features modified may include at least a portion of the mitral valve. An affect of the modification on one or more features derived from the image may be assessed. One or more three-dimensional images of the assessed results of the virtual heart reconstruction may be created by a computer system.

In an embodiment, a method of assessing cardiac electrical activity may include providing one or more images of heart tissue from a human heart to a computer system. One or more features of the image may be modified. An electrical affect of the modification on one or more features derived from the image may be assessed. One or more three-dimensional images of assessed electrical effects of the modification may be created by a computer system. Progressive coloring of the assessed viability may be used in the created image to display the extent of an electrical effect.

In one embodiment, a method of assessing a treatment of heart tissue from a human heart may include providing one or more images of heart tissue from the heart to a computer system. One or more features of the image may be modified. The computer system may be used to compare the modification of at least one feature of the image to one or more heart reference features in a database to assess the state of the human heart. The database may include data from one or more prior treatments of heart tissue from one or more human hearts.

In an embodiment, a method of creating multi-dimensional human heart tissue images may include providing a plurality of images of human heart tissue to a computer system. One or more of the images of human heart tissue may have been collected using a specified protocol. The plurality of images may be at least two-dimensional. At least one second image may be created using the computer system. The second image may be at least three-dimensional.

In some embodiments, a method of remotely assessing treatment of a human heart may include providing a heart procedure assessment program accessible via a network. At least one image of heart tissue from the heart may be provided to the heart procedure assessment program. The heart procedure assessment program may be accessed remotely to assess a procedure for treatment of the heart.

In one embodiment, a method of assessing a surgical procedure on a human heart may include allowing a user to perform a modification to at least one feature of the heart using a computer system. A performance of the user may be assessed by comparing the user's modification to a database of modifications.

In an embodiment, a method of assessing plication strategies on heart tissue from a human heart may include providing at least one image of heart tissue to a computer system. At least one of the images comprises at least a portion of an interior chamber of the heart. At least a portion of an interior chamber may be reconstructed. An effect of a reconstruction of at least a portion of the interior chamber on at least another portion of the heart may be assessed. One or more three-dimensional images of assessed plication strategies of the modification may be created by a computer system. Progressive coloring of the assessed plication may be used in the created image.

In some embodiments, a method of enhancing images may include providing at least two images of the heart tissue to a computer system. At least one image may include an enhanced portion. At least a portion of at least one image may be enhanced by combining at least a portion of at least one of the images with at least the enhanced portion of a second image.

In an embodiment a system may function to employ any of the methods described herein. The system may include a CPU. The system may include a system memory coupled to the CPU. The system memory may store one or more computer programs executable by the CPU. One or more computer programs may be executable to perform any of the methods outlined herein.

In some embodiments, a carrier medium may function to store program instructions. The program instructions may be executable to implement a method as described herein.

In an embodiment, a report may include a description of a result or an effect of a method as described herein.

In some embodiments, a method as described herein may include assessing a cost to be charged to a user for using the method based on a number of times the user applies the method.

BRIEF DESCRIPTION OF THE DRAWINGS

Advantages of the present invention may become apparent to those skilled in the art with the benefit of the following detailed description of the preferred embodiments and upon reference to the accompanying drawings in which:

FIG. 47 depicts an embodiment of a comparison of systole and diastole images to determine a border zone between akinetic and functional tissue.

FIG. 48 depicts an embodiment of a pictorial representation of a cross-sectional view of a ventricle and a method of measuring a scar as a percentage of an endocardial boundary.

FIG. 49 depicts an embodiment of a mesh that has anatomical landmarks of a heart and a location of a diseased tissue superimposed on it.

FIG. 63 depicts an embodiment of two examples of convolution masks.

FIG. 64 depicts an embodiment of an example image and a kernel.

FIG. 65 depicts an embodiment of an example of pseudo-convolution masks used to quickly compute approximate gradient magnitude.

Figure 1:
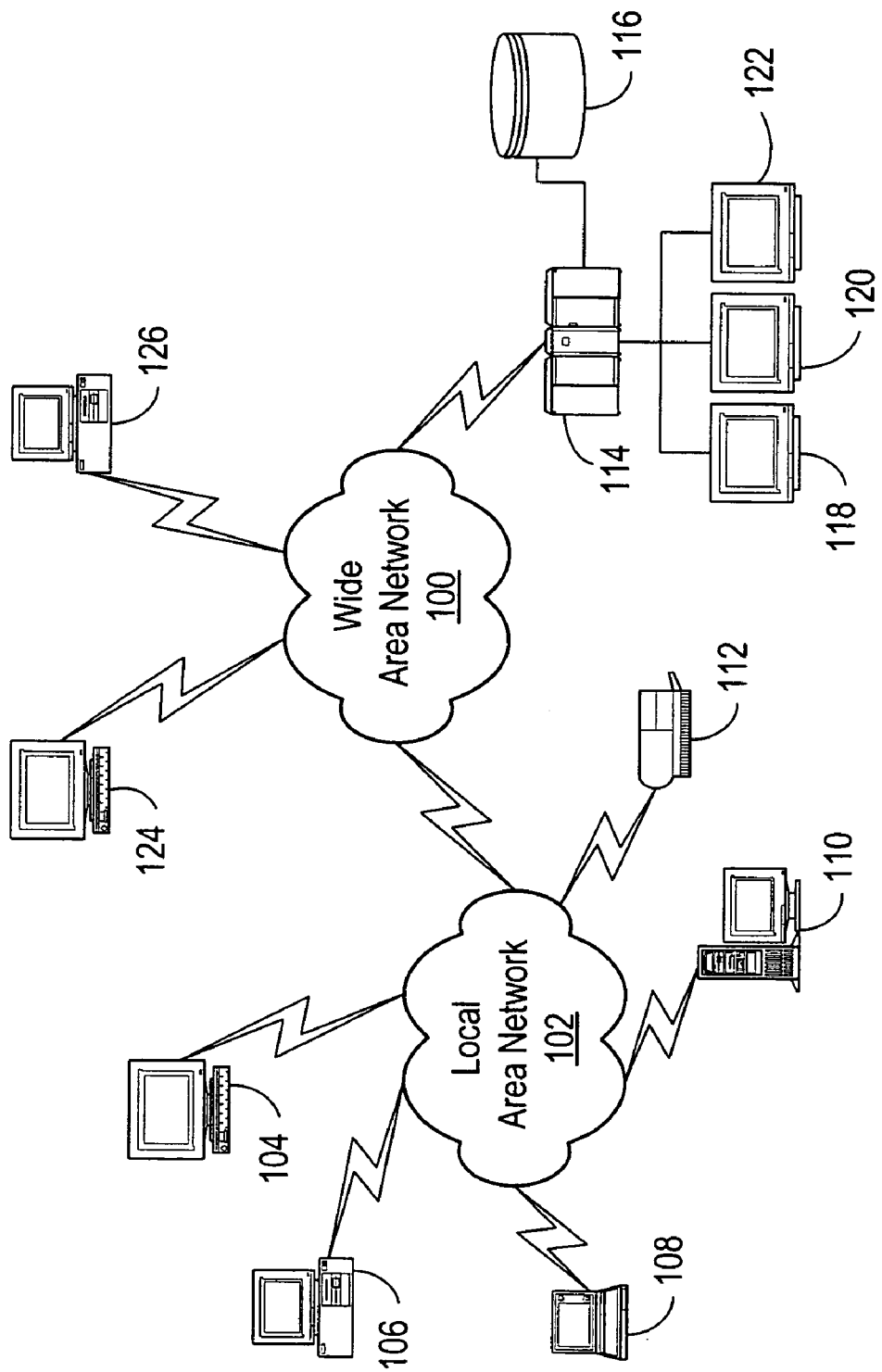
FIG. 1 depicts a network diagram of an embodiment of a wide area network that may be suitable for implementing various embodiments.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

Methods and apparatus of various embodiments will be described generally with reference to the drawings for the purpose of illustrating the particular embodiments only, and not for purposes of limiting the same. The illustrated embodiments address the ability of a user (e.g., a physician) to accurately assess the effects of cardiac disease on an individual patient and to use an appropriate treatment to restore the cardiac system to its optimal or best acceptable condition. In one embodiment, this is accomplished by using an analytical tool that takes images of the patient's own heart and collects other data related to the functioning of the heart. The collected data may be used to create a multi-dimensional finite element model and/or image of the heart. The multi-dimensional finite element image of the patient's heart may interact and respond to other models or a set of models. For example, the model of the patient's heart may also be connected to a model of the circulatory system and/or a model of the cardiac system. These models, in combination, may simulate the performance of the heart and its effect on the circulatory system. The use of these models may allow a user to determine the appropriate areas of the heart to be repaired, replaced, or otherwise medically treated for the patient. The models may also allow the user to determine the effects that the treatment may have on the portions of the heart and/or on the entire heart.

In an embodiment, a cardiac intervention process may include diagnosis, designing and/or manufacturing cardiac instruments, creating a procedure for cardiac modification, and/or prescribing a treatment of a cardiac disease. A cardiac disease may include any cardiac irregularity. A cardiac irregularity may be associated with a structural defect or abnormality of a heart. Other cardiac irregularities may be associated with a chemical or hormonal imbalance. Additional cardiac irregularities may include electrical abnormalities (e.g., arrhythmia). A method may include analyzing and performing a virtual treatment of a cardiac irregularity. A method of performing a virtual cardiac intervention may be performed on a computer system. A computer system may be a local computer system, including, but not limited to, a personal computer. Other embodiments may include remote systems or two or more computers connected over a network.

FIG. 1 illustrates a wide area network ("WAN")according to one embodiment. WAN 100 may be a network that spans a relatively large geographical area. The Internet is an example of a WAN. WAN 100 typically includes a plurality of computer systems that may be interconnected through one or more networks. Although one particular configuration is shown in FIG. 1, WAN 100 may include a variety of heterogeneous computer systems and networks that may be interconnected in a variety of ways and that may run a variety of software applications.

One or more local area networks ("LANs") 102 may be coupled to WAN 100. LAN 102 may be a network that spans a relatively small area. Typically, LAN 102 may be confined to a single building or group of buildings. Each node (i.e., individual computer system or device) on LAN 102 may have its own CPU with which it may execute programs, and each node may also be able to access data and devices anywhere on LAN 102. LAN 102, thus, may allow many users to share devices (e.g., printers) and data stored on file servers. LAN 102 may be characterized by a variety of types of topology (i.e., the geometric arrangement of devices on the network), of protocols (i.e., the rules and encoding specifications for sending data and whether the network uses a peer-to-peer or client/server architecture), and of media (e.g., twisted-pair wire, coaxial cables, fiber optic cables, and/or radio waves).

Each LAN 102 may include a plurality of interconnected computer systems and optionally one or more other devices such as one or more workstations 104, one or more personal computers 106, one or more laptop or notebook computer systems 108, one or more server computer systems 110, and one or more network printers 112. As illustrated in FIG. 1, an example of LAN 102 may include at least one of each of computer systems 104, 106, 108, and 110, and at least one printer 112. LAN 102 may be coupled to other computer systems and/or other devices and/or other LANs 102 through WAN 100.

One or more mainframe computer systems 114 may be coupled to-WAN 100. As shown, mainframe 114 may be coupled to a storage device or file server 116 and mainframe terminals 118, 120, and 122. Mainframe terminals 118, 120, and 122 may access data stored in the storage device or file server 116 coupled to or included in mainframe computer system 114.

WAN 100 may also include computer systems connected to WAN 100 individually and not through LAN 102 such as, for purposes of example, workstation 124 and personal computer 126. For example, WAN 100 may include computer systems that may be geographically remote and connected to each other through the Internet.

Figure 2:
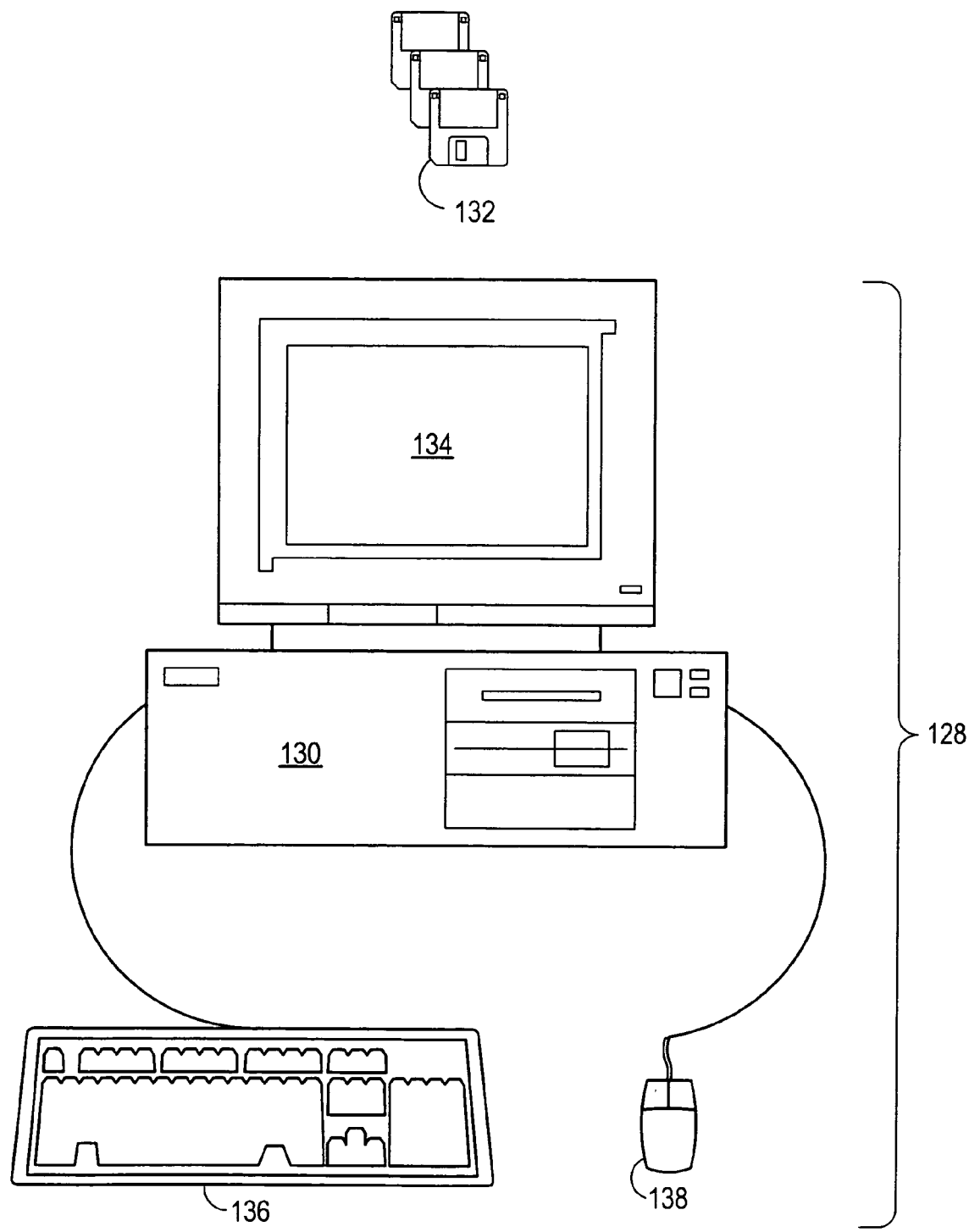
FIG. 2 depicts an illustration of an embodiment of a computer system that may be suitable for implementing various embodiments.

FIG. 2 illustrates an embodiment of computer system 128 that may be suitable for implementing various embodiments of a system and method for restricting the use of secure information. Each computer system 128 typically includes components such as CPU 130 with an associated memory medium such as floppy disks 132. The memory medium may store program instructions for computer programs. The program instructions may be executable by CPU 130. Computer system 128 may further include a display device such as monitor 134, an alphanumeric input device such as keyboard 136, and a directional input device such as mouse 138. Computer system 128 may be operable to execute the computer programs to implement a method for facilitating cardiac intervention as described herein.

Computer system 128 may include memory medium on which computer programs according to various embodiments may be stored. The term "memory medium" is intended to include an installation medium, e.g., a CD-ROM, or floppy disks 132, a computer system memory such as DRAM, SRAM, EDO RAM, Rambus RAM, etc., or a non-volatile memory such as a magnetic media (e.g., a hard drive or optical storage). The memory medium may also include other types of memory or combinations thereof. In addition, the memory medium may be located in a first computer that executes the programs or may be located in a second, different computer that connects to the first computer over a network. In the latter instance, the second computer may provide the program instructions to the first computer for execution. In addition, computer system 128 may take various forms such as a personal computer system, mainframe computer system, workstation, network appliance, Internet appliance, personal digital assistant ("PDA"), television system, or other device. In general, the term "computer system" generally refers to any device having a processor that executes instructions from a memory medium.

The memory medium may store a software program or programs operable to implement a method for restricting the use of secure information as described herein. The software program(s) may be implemented in various ways, including, but not limited to, procedure-based techniques, component-based techniques, and/or object-oriented techniques, among others. For example, the software program(s) may be implemented using ActiveX controls, C++ objects, JavaBeans, Microsoft Foundation Classes ("MFC"), browser-based applications (e.g., Java applets), traditional programs, or other technologies or methodologies, as desired. A CPU such as host CPU 130 executing code and data from the memory medium may include a means for creating and executing the software program or programs according to the methods and/or block diagrams described herein.

Figure 3:
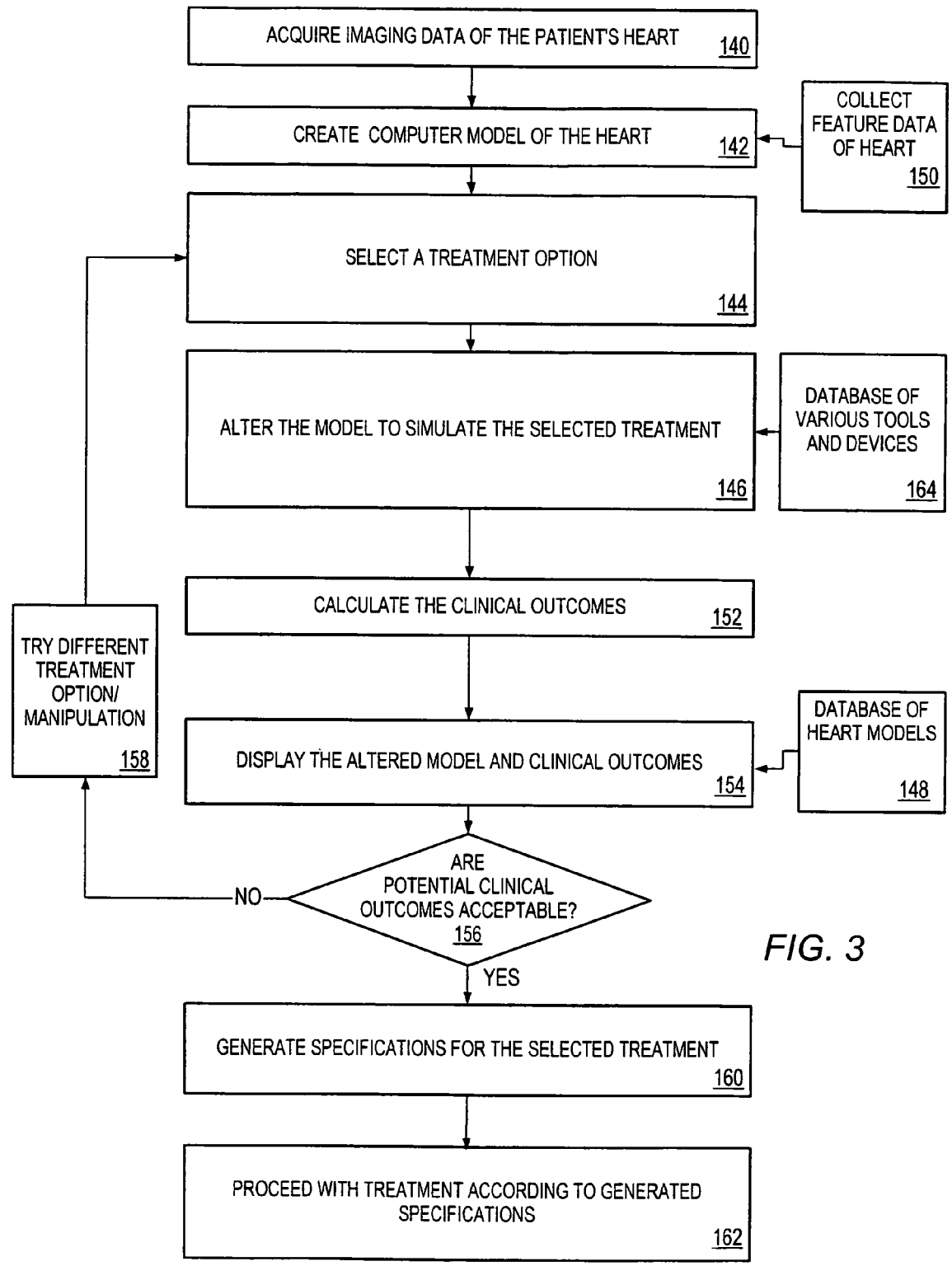
FIG. 3 depicts a flowchart of an embodiment of a method for performing a virtual interactive cardiac valve correction.

One embodiment of a cardiac intervention method may include a system and method for capturing the geometry of the heart and its components using imaging technologies. FIG. 3 depicts a flowchart of an interactive method for determining a treatment for a cardiac condition. The method begins with acquiring image data of the heart (140). Image data may be collected using a variety of imaging technologies that include, but are not limited to, MRI imaging, echocardiography, or PET. These imaging systems are common in most hospitals and the leading manufacturers of these systems are General Electric, Siemens, and Phillips. Additional features of the patient's heart may also be collected (150). Some additional features of the patient's heart that may be captured and/or calculated include:

a. Myocardial stiffness
  b. Ventricle wall thickness
  c. Heart rate
  d. Ventricle wall tension
  e. Right and left ventricle volumes
  f. Mitral Valve Annulus
  g. Chordae Tendinae
  h. Papillary Muscles
  i. Mitral Valve Leaflets
  j. Ventricle Endocardium Border
  k. Ventricle Epicardium Border
  l. Aortic valve annulus
  m. Aortic valve cusps
  n. Tricuspid valve apparatus
  o. Pulmonary valve apparatus
  p. Ventricle wall thickness
  q. Ventricles areas of akinesia
  r. Ventricle areas of dyskinesia
  s. Ventricle areas of asynergy
  t. Ventricle preload
  u. Ventricle filling pressure
  v. Heart's arterial system
  w. Heart's flow through the arterial system
  x. Heart's venous system
  y. Left and right atrium volumes
  z. Left and right atrium wall thickness.

Some or all of these features may be used to create a computer model of the patient's heart (142). In some embodiments, a computer model of the heart is a multi-dimensional finite element computer model. A computer model may include a mathematical model of a heart. A mathematical model may include an image or graphical representation of one or more of the dimensions of a computer model. One example of a multi-dimensional model is a three-dimensional model that displays not only the three dimensions of a geometry of a heart but may also depict this geometry as it changes over time. Multi-dimensional models (e.g., three-dimensional or greater than three-dimensional models) may include two-dimensional graphically displayed models that appear to be three-dimensional or greater models. For example, a computer screen may produce a two-dimensional model that appears three-dimensional. In some embodiments, multi-dimensional models (e.g., three or greater dimensional models) may include holographic projections. Other dimensions that may be modeled include physiological factors such as the production of hormones. For example, the heart produces a hormone B-type natriuretic peptide in reaction to increased wall stress. The production of this hormone could be depicted in the generated computer model. Another non-limiting example of a dimension of a heart model may include electrical activity of a heart.

Software producing the model may run on a personal computer, or it may run at a central location accessible by one or more personal computers. The computer model may be produced using a computer at one location and the model delivered to a different computer at another location.

A multi-dimensional model of a subject or patient's heart may allow a user to visually inspect the status of many elements of a heart. The user may use the computer model to assess and/or determine the condition of the patient's heart. Assessing information or data, as generally used herein, may be generally defined as qualitatively deriving or extrapolating a result from provided data. Determining information or data, as generally used herein, may be generally defined as a quantitative derivation or extrapolation of a result from provided data. Information assessed and/or determined from a computer model of the patient's heart and from the features of the heart may include, but is not limited to:

a. Areas of the mitral, aortic, tricuspid or pulmonary valves that may need to be repaired or replaced and what affect each repair may have on the other components.
  b. What vessels are blocked and may need to be grafted, where to graft and what effect the revascularized muscle may have on the other components.
  c. What areas of the ventricle are akinetic, dyskinetic or hibernating, to show what areas may be excluded during ventricular restoration and what effect the exclusion may have on the other components and aspects of the ventricle and heart.

d. How a patient's heart may respond to medication treatment.

e. The effects of placement of a corecap-restraining device, Myosplint shape changing device, or other device on the outside of the ventricle and how these devices may affect the heart.

f. The effects of chordae length adjustment or papillary base relocation on the heart.

g. The effects of placement of any ventricular assist device on the heart (e.g., a pacemaker).

h. The vessels that are blocked and may need to be stented, where to stent and the effect the revascularized muscle may have on the other components of the heart.

i. Determining and/or assessing possible electrical effects in the heart (e.g., arrhythmia) arising as a result of the proposed cardiac interventions.

j. Assessing fluid flow (e.g., blood) across a portion of the heart (e.g., the aorta) using at least some data from existing imaging and measuring protocols (e.g., CMR).

k. Assessing mitral regurgitation for a specific patient.

l. Assessing a percent of viable and/or nonviable tissue for the heart. Images acquired from, for example, an MRI may be provided to a computer system where the images have been enhanced. The images may have been enhanced using techniques such as gadolinium enhancement of the NRI. Enhancement techniques such as these may improve the contrast between viable and nonviable tissue in MRI images.

m. Analyzing a shape of the heart or a portion of a heart as well as assessing an affect occurring from reshaping or reconstructing a portion of a heart. During analysis, a heart may be divided into one or more sections or segments. A curvature of each of the sections may be measured. A computer system may be used to automatically measure a curvature of a section. The computer system may assess the shape of an interior chamber of the heart by determining the curvature of a plurality of sections. Determined curvatures may be added together to assess a shape of the heart.

n. A volume in a portion of a heart (e.g., an interior chamber of a human heart) may be assessed using the method and/or system described herein.

o. An end diastolic volume of a portion of a heart from a specific patient may be assessed by providing at least one image to a computer system.

p. An end systolic volume of a portion of a heart from a specific patient may be assessed by providing at least one image to a computer system.

q. An ejection fraction may be assessed by a computer system.

r. Motion of at least a portion of a heart may be analyzed to assess a viability of the portion of the heart.

s. A shape of at least a portion of a heart may be assessed by providing at least one image to a computer system.

t. A degree of transmurality of a portion of heart tissue scarring might be assessed by a computer system.

u. A thickness of at least a portion of a wall may be assessed.

v. Distances and angles between papillary muscles may be assessed. In an embodiment, distances and/or angles between papillary muscles and a portion of the heart may be assessed. Assessed angles and/or distances may be used to assess a condition of a mitral valve.

w. Flow of a fluid across a portion of a heart may be assessed. The fluid may include blood and/or some physiological fluid. The portion of the heart may include the aorta.

x. Mitral regurgitation of a human heart may be assessed by providing at least one image of a heart to a computer system.

y. Viability of human heart tissue may be assessed by assigning reference points to an image constructed by a computer system using patient specific data provided. Motion over time of the reference points may assist in assessing viability of human heart tissue by comparing the motion to "normal" heart tissue.

z. Particular procedures may be assessed. For example, plication procedures may be assessed using a computer system.

Based on a user's analysis of the functioning of the heart and the properties of the various components of the heart (e.g., the analysis listed above), a user may make a diagnosis of the heart's condition. Based on the diagnosis of the heart, the user may choose a treatment option (144).

A model may assist the user in the selection of a treatment option (144). After the user has selected a treatment option, the user may alter the computer model of the patient's heart (146) to simulate the proposed treatment of the heart. For example, the computer software may allow the user to alter the model by placing one or more synthetic devices in various portions of the computer model of the heart. The computer software, in certain embodiments, may include a database (164) that includes computer models of a variety of tools (e.g., surgical tools, medicants) and devices (e.g., pacemakers, stents, patches, staples, a shaper (such as a balloon or wire mesh used to reconstruct a left ventricle)) that may be used for a variety of treatments. Altering the computer model of the patient's heart may involve importing one or more of these tools or devices into the computer model from the database (164).

The computer model may also be used to analyze what effects the selected virtual treatment may have on the patient's heart. The insertion of cardiac devices or the performance of a surgical technique may alter the geometry of a patient's heart. The modeling software may alter the model of the patient's heart (146) in response to the selected treatment. The user may view the altered computer model to determine the geometrical effect of the proposed treatment. For example, the placement of a synthetic device into the heart may alter the shape and size of the heart. If a surgical procedure is contemplated by the user, the computer software may simulate the outcome of the surgery.

Additionally, the computer software may determine the effect of the treatment on various features of the patient's heart. For example, the software may calculate physiological properties of the heart based on known properties of hearts (152). The results of these calculations may be displayed in the computer model of the patient's heart (154). In addition to the altered computer model, the potential outcomes displayed may include, but are not limited to, the following:

a. The estimated performance of the valves and ventricle after the procedure; e.g., regurgitation, reduced flow across the valves, ejection fraction, etc.

b. The flow through the grafts or stents and what areas of the myocardium the grafts or stents may perfuse.

c. The volume and contractile state of the ventricle after excluding tissue.

d. The positioning and performance of the valve apparatuses after reconstruction of the ventricle.

e. The effects that a drug or combination of drugs may have on the entire heart.

The user may use the displayed information to diagnose the outcome of the proposed treatment on a patient's heart (156). Diagnosing the effect of the procedure on a cardiac irregularity, where cardiac irregularities may include, but are not limited to, structural, chemical, and/or electrical irregularities may include comparing the simulated computer model of the outcome of the treatment to what is generally accepted to one skilled in the art as a healthy/normal heart. Cardiac treatments may be assessed/determined by analysis of a model of each procedure (procedure not being limited merely to a surgical procedure). Treatments may also be assessed relative to a database of heart models, where the database of heart models may include, but is not limited to, data from prior cardiac surgical procedures and/or treatments, expert opinions (e.g., cardiac surgeon specialists), and/or data derived and/or extrapolated from prior cardiac surgical procedures/treatments and/or expert opinions. Databases may be continually updated as new information is gathered. New information may be in the form of procedures modeled by users and input into the system.

Cardiac surgical procedures specifically may be assessed. Surgical procedures may be assessed at least partially by the computer system, the computer system having been provided data at least in the form of two-dimensional images. The computer system may be provided a plurality of images. A user may modify at least one feature derived from the image. The feature may represent a portion of a heart (e.g., structural feature of the heart). In an embodiment, the feature may represent some aspect or characteristic of the heart (e.g., electrical or chemical). A feature may be modified virtually. A modification of a feature may be assessed. Assessment of a modification may include determining an effect that modifying at least one feature has on at least one other feature.

The designing and manufacture of surgical instruments may also be accomplished by methods set forth herein. The computer system may use the computer model of a patient's heart to design a cardiac instrument for a surgical procedure based on the information provided. A cardiac instrument may include, but is not limited to, an actual surgical tool employed by a surgeon during an operation, a patch, or a template. In an embodiment, designs for a cardiac instrument may be used to manufacture the instrument.

The user, after analysis of the modified computer model, is able to select the displayed intervention (156) or to decide to try another treatment or modify the current intervention (158). When the user decides to attempt another treatment, the cycle may repeat itself by returning to the treatment option portion of the method. When the user accepts the potential clinical outcomes, the model may produce one or more specifications for the selected treatment (160). These specifications may lead to the development of a template, or tools or devices, to guide the user in translating the virtual intervention on the model to the actual intervention on the heart (162). Tools and devices may include cardiac instruments such as ventricle patches, ventricle shapers, and sizers. A computer system may assist in designing cardiac instruments using the images as a model to produce patient specific devices. In some cases templates, tools, and/or devices may not be needed to perform the intervention and specifications. In such cases, the computer may prepare specifications for performing the selected surgical procedure. Additional devices may be generated from the models to help the user implement the surgical procedure that the model may have predicted to provide the best outcome. Furthermore, the use of some or all of the above listed factors may be used to evaluate the post-treatment condition of the patient. A database of (148) of surgical pathologies, treatments and outcomes may be gathered, maintained, and analyzed to further refine the treatment of cardiac diseases and disorders. The database may include heart models that may be used for comparison with the altered model of the patient's heart.

In some embodiments, users may assist in updating and/or maintaining a database. Users may assist in maintaining a database by correcting inconsistencies and/or flaws in the database. Users may directly make corrections and/or may be provided means to inform a database administrator about possible corrections. Users may assist in maintaining a database by providing further data based on personal research. Personal research may include academic and/or practical research. In certain embodiments, users may be offered incentives (e.g., monetary rewards) to assist in updating and/or maintaining a database.

In some embodiments, post-treatment imaging such as MRI, PET and echocardiography scanning of the above listed measurement points may show the user how well the patient has done in treatment. The images of the patient's heart before treatment and the model depiction of the treated heart, along with the predicted performance characteristics, may all be saved in a database. A user may compare actual data with predicted data and determine how to improve his technique to achieve the theoretical best results. Long-term follow up is enhanced when current images of the heart may be compared to pre- and post-treatment images of the heart. Images may be analytically compared for small changes in the heart's geometry and alignment. If small changes are detected early, less invasive measures may be taken to stop or slow the progression of the abnormality. Users may also use this database to pull up data on past patients who may have similar characteristics as the current patient under consideration, and compare his current treatment options to the past ones. Such methods may further contribute to improvement of techniques.

In certain embodiments, a subject's heart may be monitored over time (e.g., periods of weeks, months, or years). A subject's heart may be monitored using available imaging technology. Models created from the images provided may allow a user to monitor changes over time in a state of the subject's heart. For example, created models of akinetic areas of the subject's heart may be overlaid one on top of the other for comparison purposes. Methods may be used to determine progress of a patient and/or a patient's response to various treatments. In an embodiment, models may be used to create animated pictures over a time period(s) to pictorially show differences in the subject's ventricle at different times.

In an embodiment, a method may be employed to monitor a state of heart tissue over time. A subject's heart may be monitored (e.g., imaged) at rest and under stress (e.g., during and/or shortly after exercise). In some embodiments, heart stress may be initiated using artificial means such as drugs. Models of the heart at rest and under stress may be compared. For example, wall motion abnormalities may be better observed. Models of the heart at rest and under stress may be overlaid to pictorially show changes and/or abnormalities.

Figure 4:
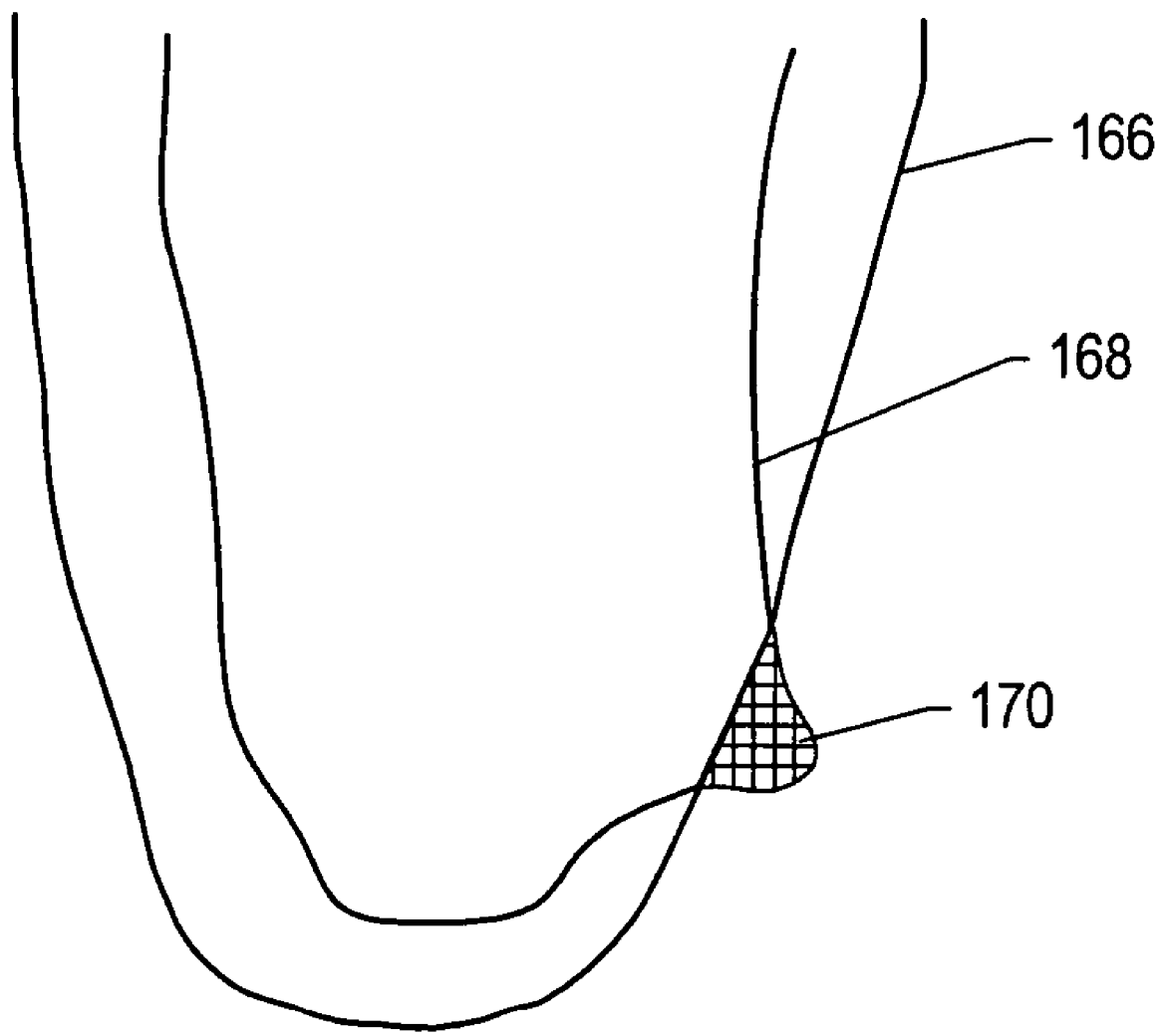
FIG. 4 depicts an embodiment of a pictorial representation of a cross-sectional view of a boundary image of an EDV and an ESV of a heart.

FIG. 4 depicts an embodiment of a pictorial representation of a cross-sectional view of a boundary image of an EDV and an ESV of a heart. In some embodiments, a method may be employed to assess the existence and extent of diskinetic aneurisms and/or dyskinetic area(s). In an embodiment, models and/or images of EDV 166 and ESV 168 of a subject's heart may be overlaid. The EDV may be transparent. The integrated model including the EDV and ESV may be manipulated by a user to facilitate evaluation of any possible aneurisms by the user. If the boundary of the ESV crosses over the boundary of the EDV then there may exist aneurism 170. The model may assess the existence of an aneurism. The model may calculate an extent of the aneurism by comparing the area of the ESV outside the boundary of the EDV to the area of the ESV inside the boundary of the EDV. Overlaid models may be pictorially demonstrated to more effectively communicate findings of the method.

In an embodiment, the method and systems described in FIG. 3 may be used to determine an appropriate treatment for cardiac valve correction. In a cardiac valve correction procedure, imaging information of the patient's ventricle is collected (140). Other information such as, but not limited to, stiffness, wall thickness, heart rate, wall tension, ventricle volume, valve apparatus locations, and epicardium and endocardium borders may be needed to convert the data to a multi dimensional model of the ventricle.

Figure 5:
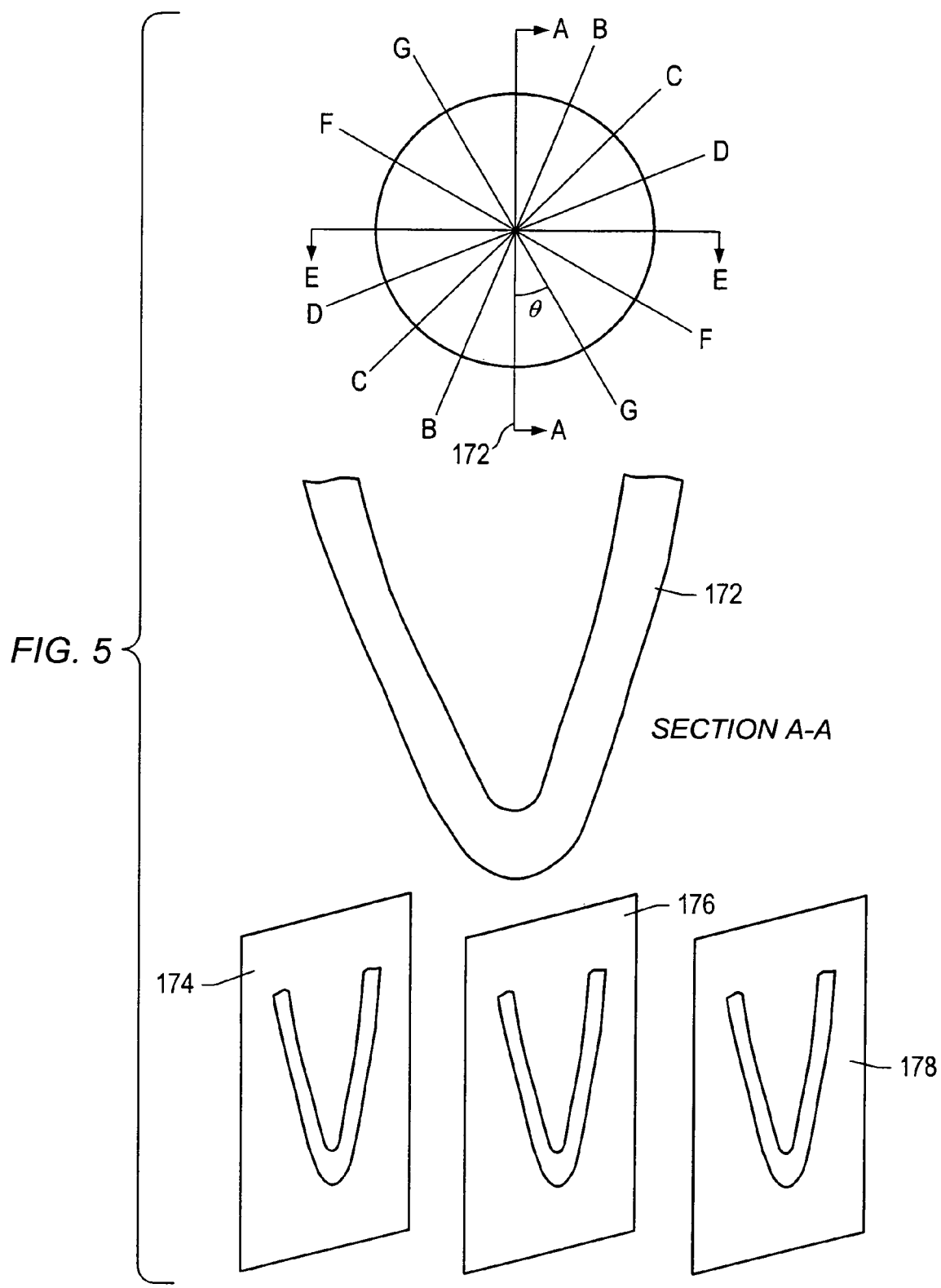
FIG. 5 depicts sectional views along the long axis of a heart obtained using MRI and Echocardiography.
Figure 6:
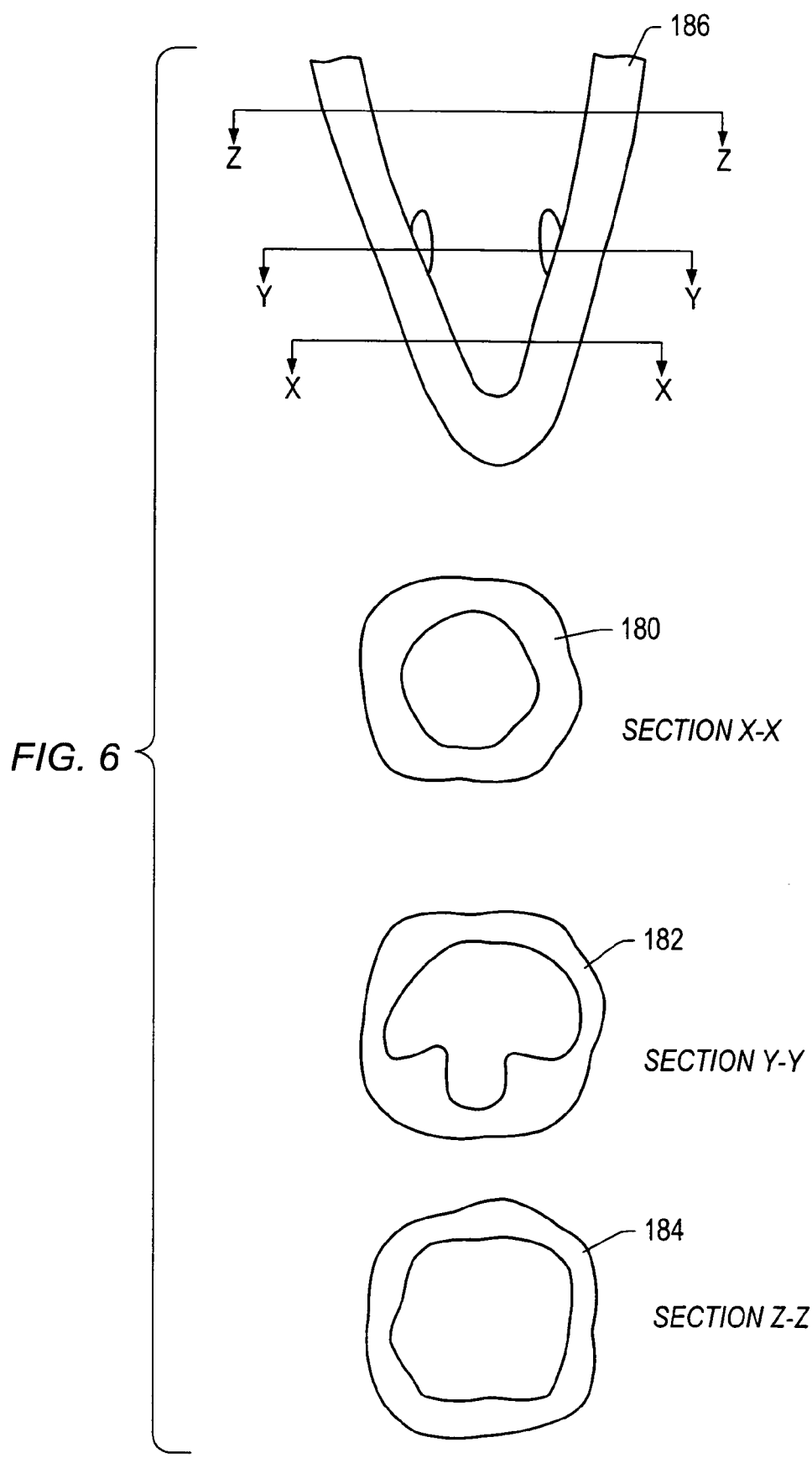
FIG. 6 depicts sectional views along the short axis of a heart using MRI and Echocardiography.

The imaging data is often acquired as sectional views (see, for examples FIGS. 5 and 6). For example, sectional views of a portion of a heart along the long axis are depicted in FIG. 5. Each sectional view (172, 174, 176, and 178) is taken along a different cross section of the portion of the heart. Sectional view 172 represents the image of the portion of the heart along plane AA. Other sectional views (174, 176, and 178) are collected along other planes (e.g., BB, CC, DD, EE, FF, or GG). Alternatively, data may be collected along the short axis of the portion of the heart as depicted in FIG. 6. FIG. 6 depicts three cross-sectional views (180, 182, and 184) of the heart 186 along planes XX, YY and ZZ (respectively). In some embodiments, data from both long axis and short axis scans of the heart may be used to prepare the computer model. It should be understood that the data from the long and short axis scans may be redundant and sectional data along only one axis may be necessary to create a model.

Figure 7:
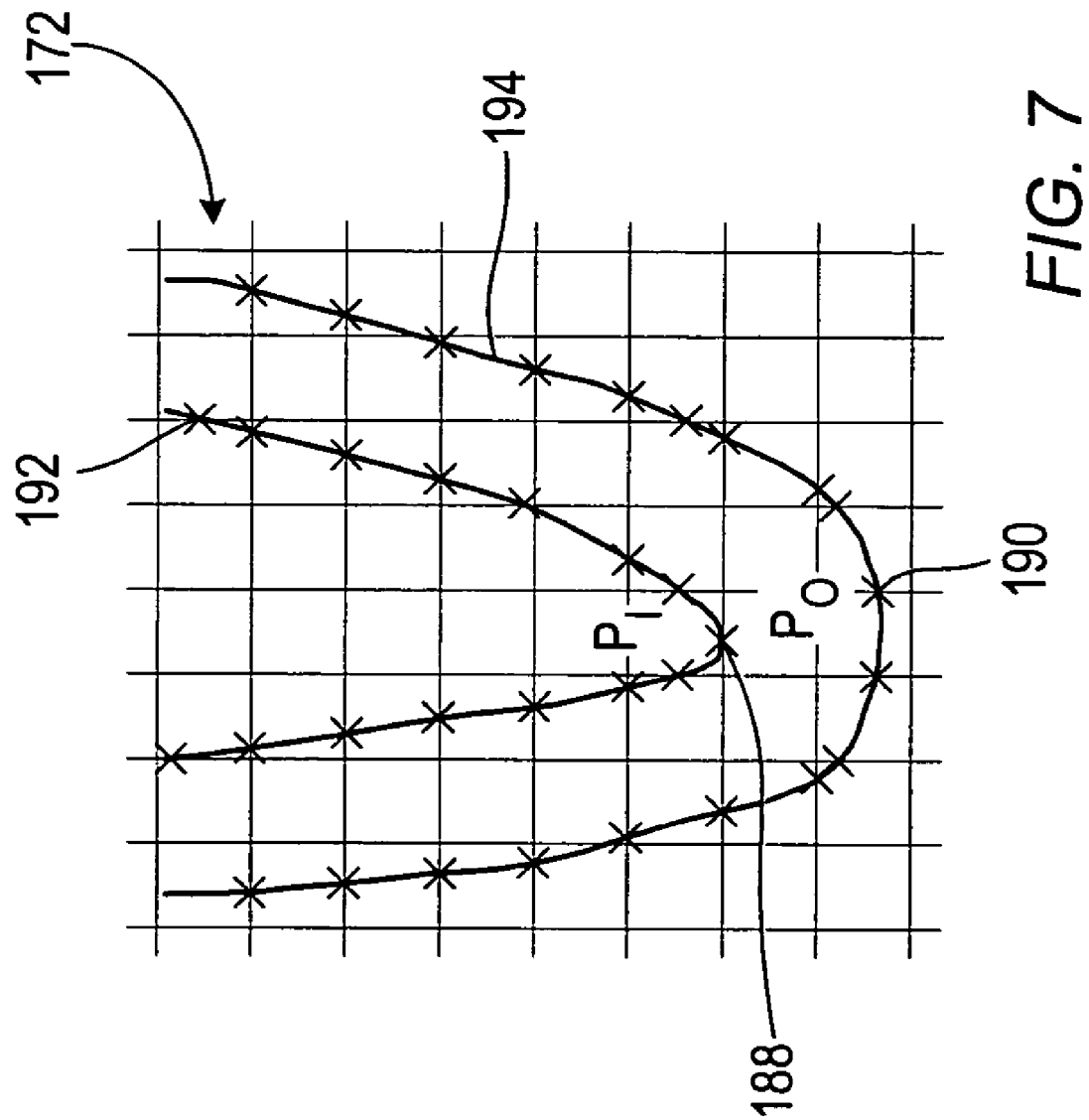
FIG. 7 depicts an embodiment of a model created from MRI images.

After the sectional views have been collected, the views may be combined to generate a three (or greater)-dimensional computer model of the heart. One method of combining sectional views and converting them into a model may be done by overlaying the sectional views on an XY grid. FIG. 7 shows cross-sectional view 172 of the heart along the long axis at plane AA from FIG. 5 with a grid superimposed over the cross-section. The points of intersection of endocardium ($P_I$, 188) and the epicardium ($P_O$, 190) with the grid lines are identified in XY coordinates, as depicted in FIG. 7. Similarly, XY coordinates of the other cross-sections (e.g., cross-sections 174, 176, and 178) are also identified using a grid. Since the angular relationship between each plane is known (e.g., angle θ between planes AA and GG as depicted in FIG. 5), all the data points may be converted into XYZ coordinates. The boundary layer generated by connecting the internal points $P_I$ of each cross-section defines the endocardial boundary 192, and the boundary layer generated by connecting the external points $P_O$ of each cross-section defines the epicardial boundary 194. In this manner, the heart may be defined in a three-dimensional space. Once the three-dimensional model is created, a time frame of the heart over which all the images were made may be added to show the heart movement during its cardiac cycle. In this manner, an example of a "four-dimensional" heart model may be created.

In some embodiments, a multi-dimensional model of heart tissue may be created. A plurality of images may be provided to a computer system. Provided images may be two-dimensional slices of a portion of a human body. Portions of the images may be segmented. Contours of various heart features may be derived from segmented portions of images. Contours along the short axis and/or long axis may be derived. The derived contours (e.g., derived from a short axis of a heart) may be aligned along an axis (e.g., along a long axis of the heart). Upon alignment, the derived contours may be used to form a wireframe model. From a wireframe model, a finite element model may be constructed. The finite element model may include one or more material properties of the modeled heart tissue.

In some embodiments, contours derived from a plurality of provided images may be used to form a wireframe model. Contours may include, for example, interpolated short-axis epicardial and endocardial contours. Contours of other heart features may be combined with the short-axis epicardial and endocardial contours. Contours of other heart features may be obtained using different techniques (e.g., enhanced MRI using dyes). For example, contours of non-viable tissue may be combined with the short-axis epicardial and endocardial contours.

In certain embodiments, derived short-axis contours may exist in three-dimensions. The derived short-axis contours are a reflection of the true position of the ventricle in three-dimensional space. To correct this, the centroid of the ventricle may be moved to the zero position so the ventricle will rotate as evenly as possible around a fixed point.

Figure 8:
FIG. 8 depicts an embodiment of an example of a wireframe model of a left ventricle including a portion of non-viable tissue.

Upon orienting the contours to be used in the correct locations in three-dimensional space, the contours may be triangulated using an algorithm. The myocardium may be created from one end to another and added to the model by assigning a specified number of triangles to each predetermined area or portion of the heart. Appropriate colors for a heart feature or an aspect may be assigned by the computer system and/or chosen by a user. FIG. 8 depicts an embodiment of an example of a triangulated wireframe model of a left ventricle including a portion of non-viable tissue.

Figure 9:
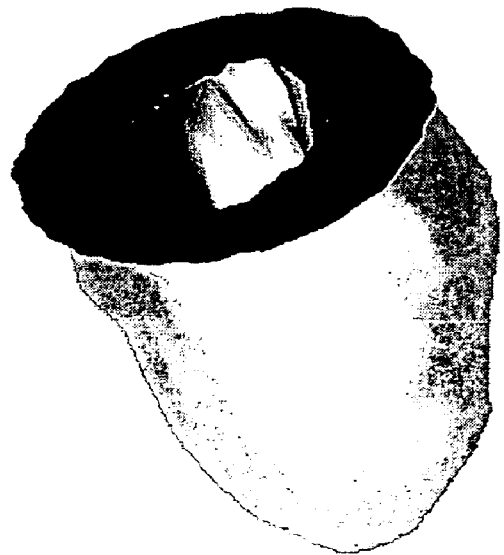
FIG. 9 depicts an embodiment of an example of a wireframe model of a left ventricle including a portion of non-viable tissue upon application of lighting parameters and calculated solid surface and vertex normals.
Figure 10:
FIG. 10 depicts an embodiment of an example of a wireframe model of a left ventricle including a portion of non-viable tissue upon application of a transparency option.
Figure 11:
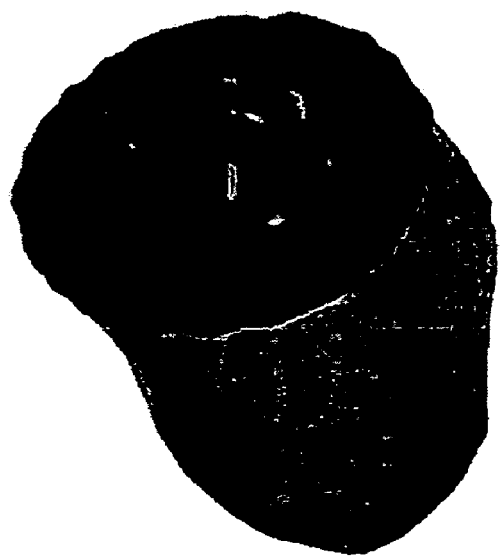
FIG. 11 depicts an embodiment of an example of a wireframe model of a left ventricle including a portion of non-viable tissue upon application of texture mapping.
Figure 12:
FIG. 12 depicts an embodiment of an example of a wireframe model of a left ventricle including a portion of non-viable tissue upon application of texture mapping and a transparency option.

After the completion of triangulation, lighting parameters may be applied by the computer system and/or selected by the user. The solid surface triangle and vertex normals may be calculated. Material lighting properties may be assigned to each surface. FIG. 9 depicts an embodiment of an example of a wireframe model of a left ventricle including a portion of non-viable tissue upon application of lighting parameters and calculated solid surface and vertex normals. The top of the ventricle depicted in FIG. 9 appears un-shaded as lighting normals have not been directly specified for this surface. This step may be intentionally skipped to aid the distinction of the two walls.

Figure 76:
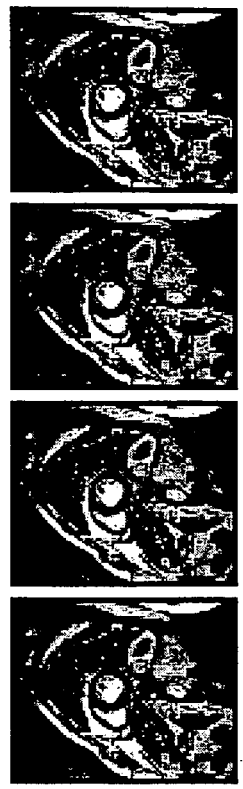
FIG. 76 depicts an embodiment of an example of a series of MRI images for a location I=2 over a phase.
Figure 76:

In an embodiment, in order to improve the visualization of the non-viable tissue in the myocardium, transparency options may be added to the model. Transparency options may allow the user to visualize the tissue with the press of a button or key. OpenGL blending options may be selected to best visualize all structures once transparency has been selected. FIG. 76 depicts an embodiment of an example of a wireframe model of a left ventricle including a portion of non-viable tissue upon application of a transparency option.

Figure 77:
FIG. 77 depicts an embodiment of a multi-dimensional image of a calculated average intensity.
Figure 78:
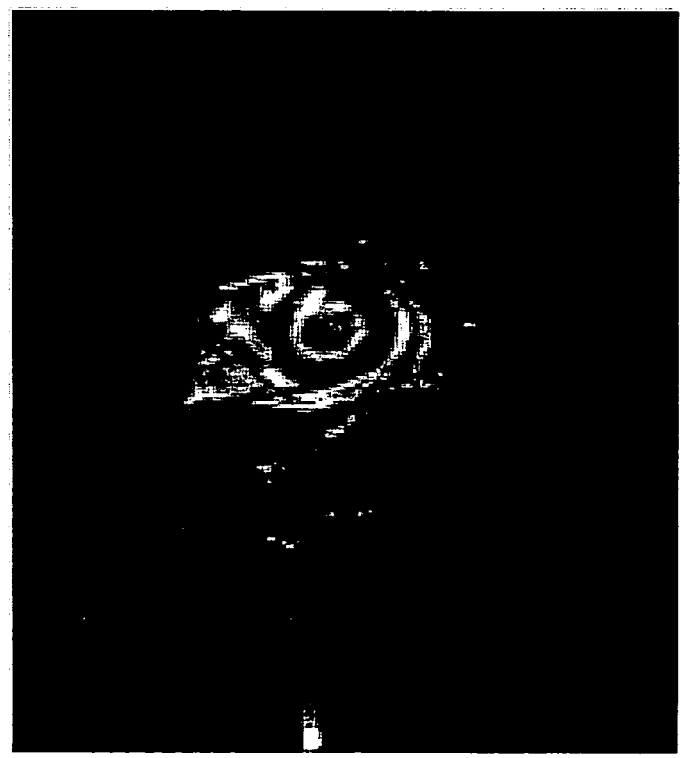
FIG. 78 depicts an embodiment of a multi-dimensional image of a calculated average variance.

In some embodiments, texture mapping may be added to the model to improve the realism of the model. FIG. 77 depicts an embodiment of an example of a wireframe model of a left ventricle including a portion of non-viable tissue upon application of texture mapping. FIG. 78 depicts an embodiment of an example of a wireframe model of a left ventricle including a portion of non-viable tissue upon application of texture mapping and a transparency option.

In some embodiments, in order to decrease blending artifacts, color blending rather than alpha blending may be utilized. In order to complete the model, keyboard options to select the rendering type, toggle options, display of the company logo, and/or model information may be added to the screen. In certain embodiments, the user may have full control of the rotation of the model with the mouse.

To be able to compare one ventricle data set to another (e.g., pre-op and post-op evaluation and/or studies done at rest and at stress), the wire frame may be designed such that the same number of triangles exist in selected portions of the modeled ventricle and/or in each of the modeled ventricles (e.g., each model has the same number of contours that define the endocardium, epicardium, etc.). Each contour may have a fixed number of vertices. For example, if there are 18 endocardial contours with 60 vertices, the endocardium is defined by 1080 triangles. Similarly the epicardium may be defined by the same number of triangles. If the endocardium and the epicardium are defined by the same number of triangles, then there will be a matching triangle for epicardium and endocardium. Using a standard number of triangles allows models from different times, states, and/or subjects to be more easily compared.

Figure 13:
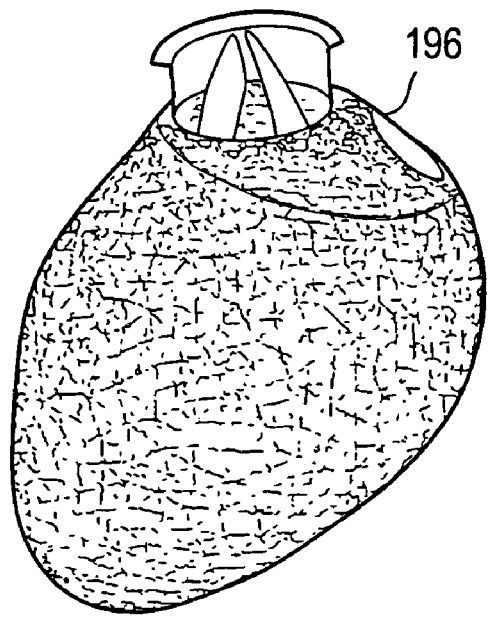
FIG. 13 depicts an embodiment of a model of a heart with a finite element grid.
Figure 14:
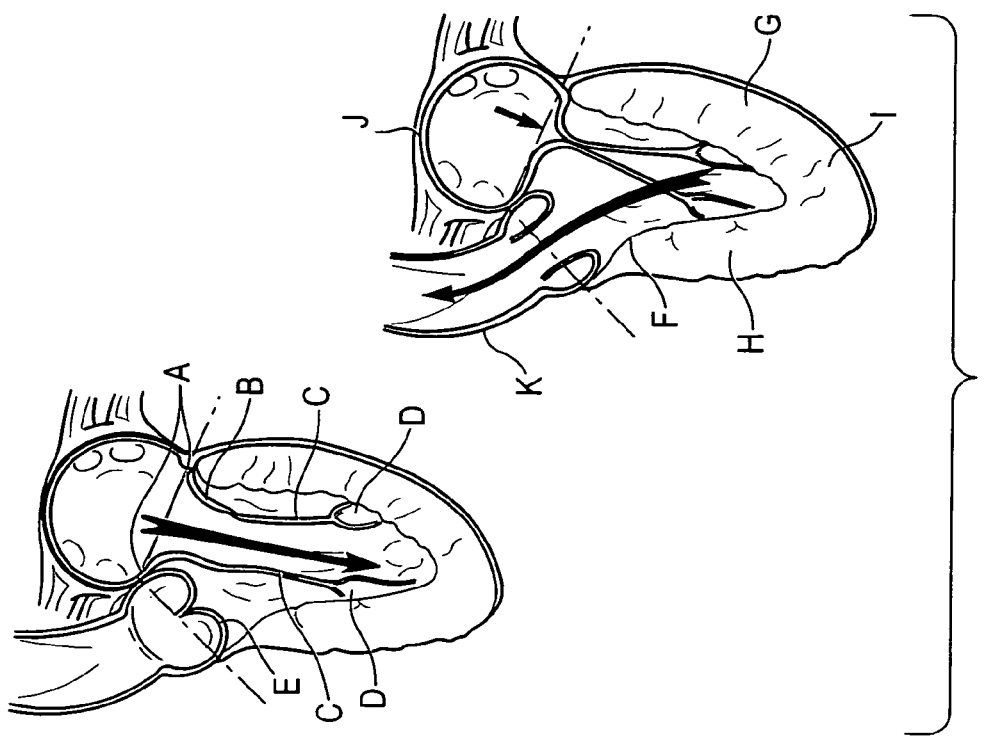
FIG. 14 depicts different features of a heart.

Once the multi dimensional object is defined, it may be converted to elements of a finite element model and a finite element mesh that represent the heart and its components to create a model 196 as depicted in FIG. 13. Some of the components of the heart that may be identified as different features of a finite element model are listed below (depicted in FIG. 14), but the apparatus and method is not limited to these components:

| | |
|---|---|
| a. Mitral valve annulus | A |
| b. Mitral valve leaflets | B |
| c. Chordae Tendinae | C |
| d. Papillary muscles | D |
| e. Aortic valve with cusps | E |
| f. Left ventricle outflow tract | F |
| g. Left ventricle walls | G |
| h. Septum | H |
| i. Myocardium of the heart | I |
| j. Left atrium | J |
| k. Ascending aorta | K. |

These elements may have different structural properties. The structural properties of myocardium and other cardiac structures may be obtained from various sources in literature. For example, properties of the ventricle myocardium may be found in, J. M. Guccione et. al., "Passive Material Properties of Intact Ventricular Myocardium Determined from a Cylindrical Model", Journal of Biomechanical Engineering Vol. 113, February 1991. Once all the structures are geometrically defined and structural properties are known, a finite element model may be created. The general creation of finite element models is well known in the art. A method of converting a defined object to a finite element mesh is described in U.S. Pat. No. 5,892,515, and is herein incorporated by reference. "Finite element analysis" is a mathematical approach to solving large (complex) problems. Generally, the subject is segmented into many pieces that have closed form solutions. That is, each piece is definable by a linear equation, and hence is a "finite element." Collectively, the linear equations of the pieces form a system of equations that are simultaneously solvable. Computer programs for simulating finite element analysis in various applications exist. For example, design engineers use finite modeling programs. Typically, many thousands of elements are created to model a subject object and in particular three-dimensional objects. For each element, there is geometric information such as an x-y-z coordinate at a point in the element, an element type, material property, stress value, displacement, thermal value, etc. Such information is definable by linear equations for the elements. To that end, finite analysis is employed to model the subject object. Examples of finite modeling programs include: ABAQUS by Hibbitt, Karlsson, and Sorensen, Inc. of Pawtucket, RI, ANSYS by Swanson Analysis Systems Inc. of Houston, Pa.; SUPERTAB by Structural Dynamics Research corp. of Ohio; and, PATRAN by PDA Engineering of Costa Mesa, Calif.

Once a finite element model of the heart has been created, an image of the heart and some of its features may appear on a monitor to allow the user to interact with the model. An image as illustrated in FIG. 13 may be displayed along with relevant data on the state of the heart (e.g., ventricle volume, blood pressure, ejection fraction, heart rate). In an embodiment, an image may be three-dimensional. In other embodiments, an image may be four-dimensional, where the fourth dimension is time. Multi-dimensional images may include "dimensions" other than geometric dimensions or time. Multi-dimensional images may include dimensions that are essentially characteristics or aspects of a particular feature of the heart.

In an embodiment, an image may be interactively connected to a model to allow the user to simulate the effects of the treatment before it is administered. For example, a pull down menu may be accessed to select the type of treatment desired (see FIG. 3, 144). Treatments for the correction of a cardiac valve may be listed. Examples of possible cardiac valve treatments include, but are not limited to inserting a synthetic valve (e.g., a St. Jude mechanical valve or a Baxter tissue valve), insertion of an annuloplasty ring, and/or performing a surgical repair (e.g., moving papillary muscle locations, surgical ventricular repair, bypass grafting, mitral valve repair, etc.). A user may select the mitral valve option to shorten the chordae tendinae or tighten the mitral annulus. In the case of the chordae tendinae, the model may separate the chordae elements from the entire model and present it to the user to allow the user to interact with the elements. Once the user has shortened the chordae tendinae, the model presents the image of the new shorter element and presents an image of the other elements with the effect that the shortening of the chordae tendinae has had on them along with clinical outcomes (152)(154).

Figure 15:
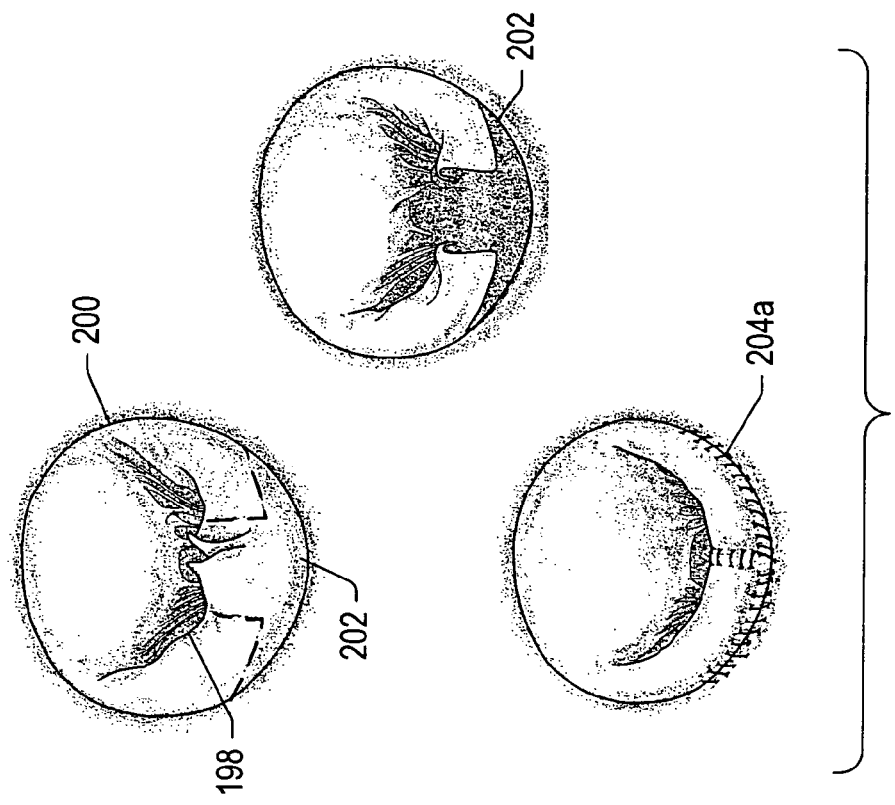
FIG. 15 depicts an embodiment of repairing a mitral valve by excising a portion of the valve and regrafting the leaflets.
Figure 16:
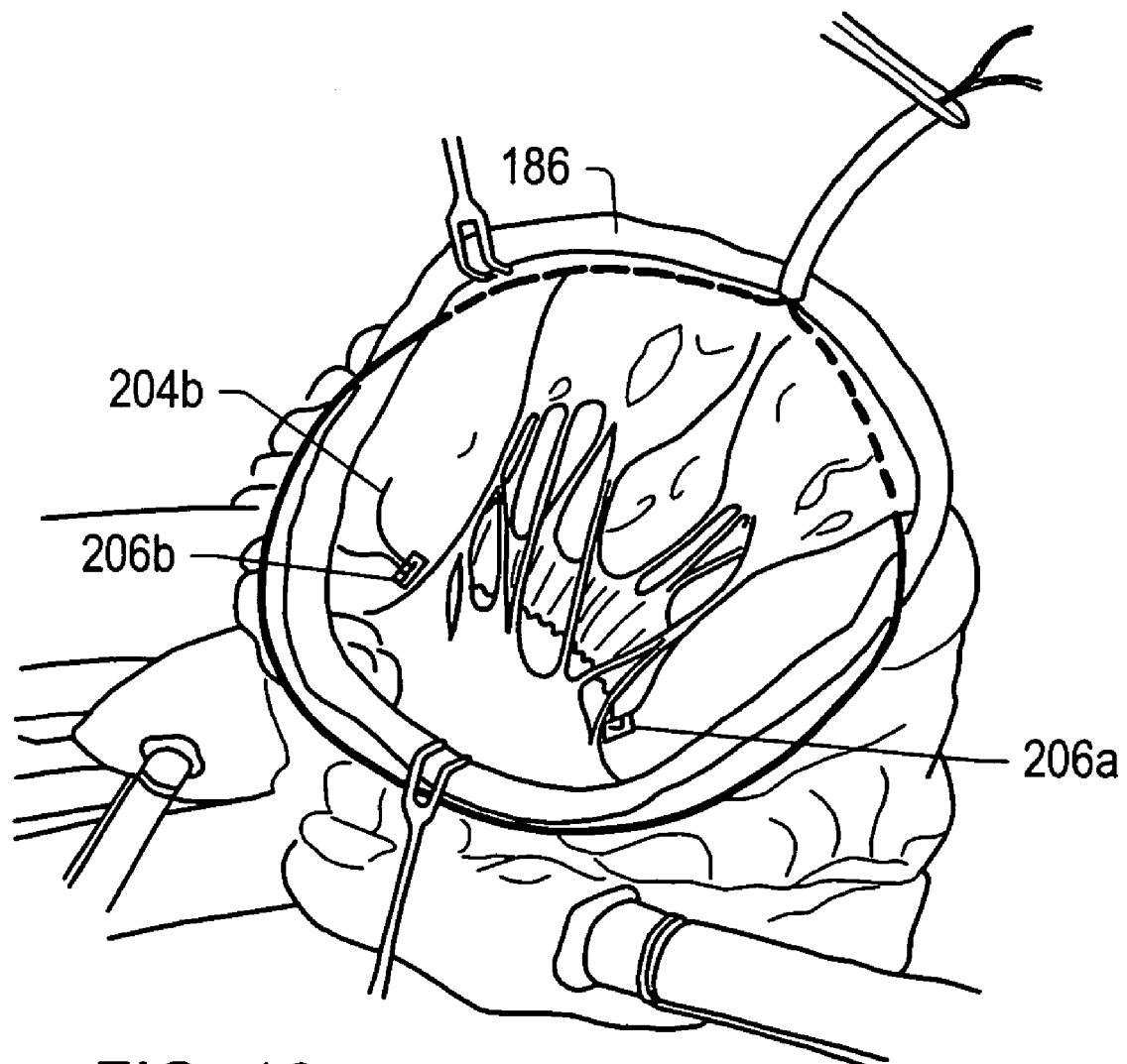
FIG. 16 depicts an embodiment of tightening a mitral annulus with a suture.

FIG. 15 depicts an embodiment of a surgical repair of a mitral valve by excising a portion of the valve and regrafting the leaflets. A mitral valve may require tightening during reconstruction of a portion of a heart. Typically, a mitral valve may need to be reconstructed when there exists mitral regurgitation in a diseased heart. A level of mitral regurgitation may be acceptable depending on the circumstances of the patient. A patient's doctor or surgeon typically determines an amount of acceptable mitral regurgitation. Mitral regurgitation may be generally described as a leaking of fluids (e.g., blood) back into an interior chamber of the heart. Mitral regurgitation leads to inefficient pumping of the heart. One solution to mitral regurgitation may be tightening of the annulus of the mitral valve. Tightening the annulus of the mitral valve may reduce or even eliminate mitral regurgitation. FIG. 15 depicts a tightening of annulus 198 of mitral valve 200. Portion 202 of mitral valve 200 may be excised from mitral valve 200. Ends of mitral valve 200 may be pulled in towards one another to tighten or restrict annulus 198. Sutures 204*a* may couple the ends of mitral valve 200 together to finish reconstruction of mitral valve 200. FIG. 16 depicts an embodiment of a surgical procedure in heart 186. The surgical procedure depicted is that of a tightening of a mitral annulus with suture 204*b*. Suture 204*b* may be inserted through openings 206*a* and 206*b*. Suture 204*b* may be tightened to restrict the annulus as opposed to excising a portion of the mitral valve.

The interaction between the user and the model may come in various forms. In some embodiments, a pull down menu standard to most software programs could present the user with a list of options, such as selecting the type of scalpel to use, the type of suture material, etc. The physical characteristics of these implements may be entered into a database (164) that a model may access. Once the user has selected the implement to use, a box or another pull down menu may appear asking for further information on how to use the implement. For example, with a scalpel the box will ask the user how long and how deep he wants to make the incision. The user will then be asked to identify by click with a mouse or stylus the start point and end point of the incision. In other examples, a surgeon or user may manipulate an instrument (e.g., a scalpel) by selecting the instrument with a mouse and manipulating the instrument by dragging it across the image with the mouse. In an embodiment, a user may manipulate an image with virtual instruments with some form of virtual interaction devices (e.g., gloves in electronic communication with a computer system).

In an embodiment, after a particular action or modification is complete, the modification may be displayed as part of an image. Referring back to the virtual surgery described in the preceding paragraph, an incision may appear on the model corresponding to the input of the user and sized appropriately for the heart according to the characteristics of myocardium, and/or other features of the heart that are built into the finite element model (148). Methods to model the physical properties of the heart may exist to create the manipulation portion of the model. A method to create a finite element model of the heart is written about by K.D. Costa et. al., "A Three-Dimensional Finite Element Method for Large Elastic Deformations of Ventricular Myocardium: I-Cylindrical and Spherical Polar Coordinates", Journal of Biomechanical Engineering, November 1996, Vol. 118 pp. 452-463, which is incorporated herein by reference. The physical properties of the elements of the heart on which to base the finite element equations for the features may be found in, Hunter P. J., et. al., "Modeling the mechanical properties of cardiac muscle", Progress in Biophysics & Molecular Biology 69 (1998) pp. 289-331, which is incorporated herein by reference. Modeling the diseased areas of the left ventricle has been described in Rez Mazhari, et. al., "Integrative Models for Understanding the Structural Basis of Regional Mechanical Dysfunction in Ischemic Myocardium", Annals of Biomedical Engineering, Vol. 28, pp. 979-2000, which is incorporated herein by reference. The properties of the ventricle myocardium may be found in, J. M. Guccione et. al., "Passive Material Properties of Intact Ventricular Myocardium Determined from a Cylindrical Model, Journal of Biomechanical Engineering Vol. 113, February 1991, which is incorporated herein by reference.

In an embodiment, a user may save the results from a particular modification of a feature. A user may desire to repeat a procedure modifying different features and/or modifying the previously modified feature in a different manner. A user (e.g., a physician or surgeon) may compare effects of different modifications and procedures to assist in determining an optimal procedure. A user may save the results of a first intervention described above and repeat the procedure in a different manner (158) to compare the outcomes of different interventions. The user may select the optimal outcomes (156) and perform the procedure in that manner. Optimal outcomes may be based on a variety of cardiac performance parameters including, but not limited to, ejection fraction, end systolic volume, stroke volume index, cardiac output, mitral regurgitation, pulmonary artery pressure, mean arterial pressure, percentage of asynergy. Optimal outcomes are very user dependent, some users may prefer higher ejection fraction and may be willing to tolerate slight mitral regurgitation. Other users will tolerate no mitral regurgitation and accept a lower ejection fraction to achieve no regurgitation through the mitral valve. When a user is satisfied that the intervention is the optimal possible for this patient, he may accept the intervention. A model may produce specifications to assist the user in performing a selected intervention (160). For example, a specification may be simply a display of the final length of the chordae. The specifications for more complicated procedures may result in the production of patient specific devices, which may assist the user with translating the virtual intervention to an actual intervention on the patient. The patient specific devices may be simple variations to the existing devices (e.g., a customized annuloplasty ring) or they may be more complex devices (e.g., a prosthetic mitral apparatus). With the information provided by the computer model the user may proceed with the intervention as defined by the specifications with some assurance that the result is optimized (162).

In an embodiment, a computer system may compare effects of different modifications of one feature and/or different features. A computer system may compare different affects of different selected procedures at the request of a user. A computer system may automatically compare different affects of different selected procedures for a user. This may assist in automating a determination of an optimal procedure for a cardiac intervention. In an embodiment, a computer system may compare effects of entered procedures to similar procedures stored in a database to assist in determining an optimal procedure.

In a cardiac treatment embodiment, not only may different cardiac virtual surgeries be compared, but also other cardiac interventions may be compared. Other cardiac interventions may not only be compared to a virtual cardiac surgery, but may as well be compared to one another. Other cardiac interventions may include such non-limiting examples as medicinal treatment with known pharmaceutical drugs or hormonal therapy. Cardiac interventions such as these may be part of a database accessible by a user. A user may simply select particular interventions (e.g., a pharmaceutical drug) from a pull down menu or any virtual selection tool commonly known in the art.

In an embodiment, a separate model or models may be used to determine the clinical outcomes of a proposed procedure. For example, the physiological and hemodynamic conditions of the heart may be modeled. The physiological properties of the heart are well understood and are written about in numerous publications including Hurst et. al., Hurst's The Heart, McGraw-Hill, 1998, which is incorporated herein by reference.

Figure 17:
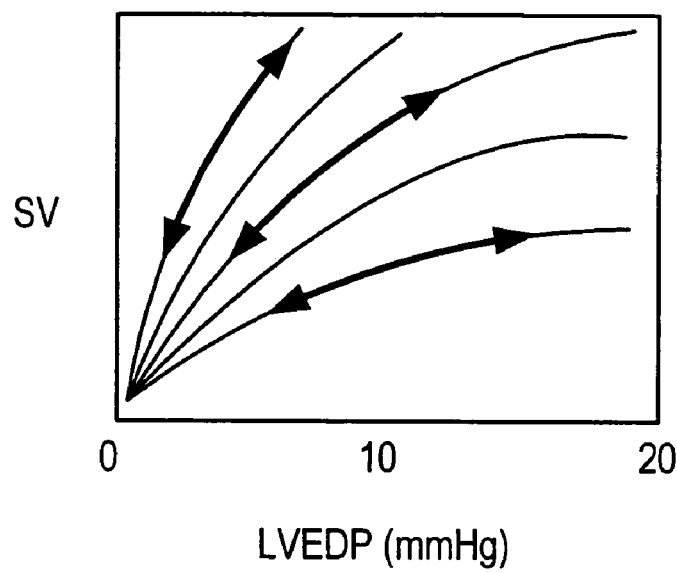
FIG. 17 depicts an embodiment of a Frank-Starling curve.
Figure 18:
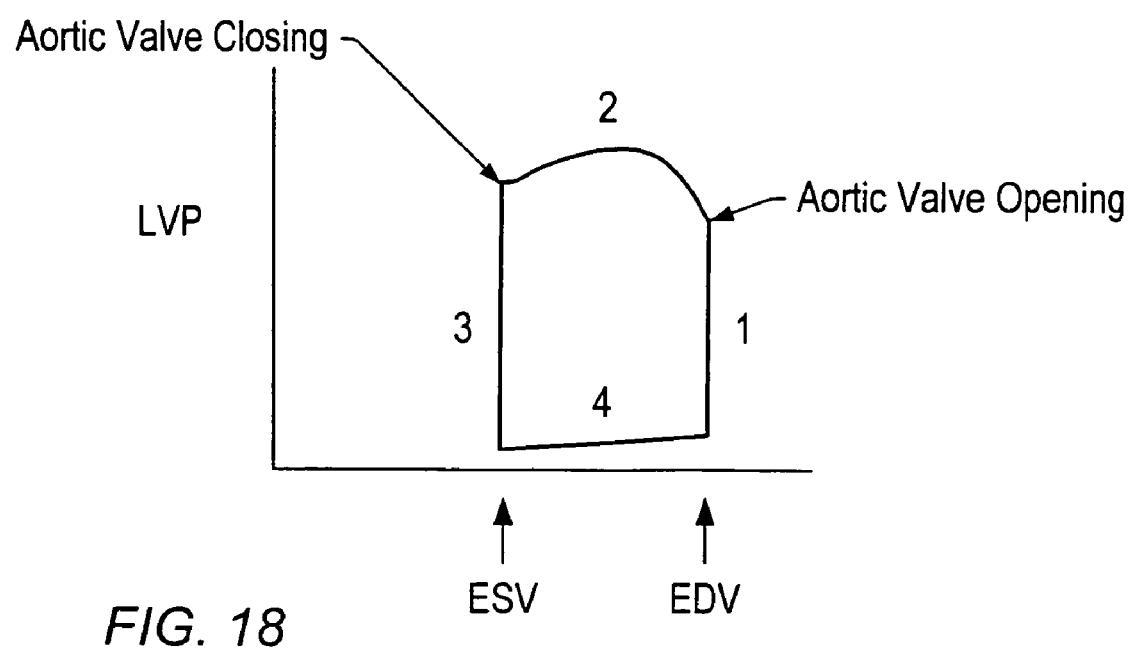
FIG. 18 depicts an embodiment of a graph of pressure volume loops during a cardiac cycle.

FIG. 17 depicts a Frank-Starling curve of a ventricle. The heart has the intrinsic capability of increasing its force of contraction when preload is increased. Preload may be defined as the initial stretching of the cardiac myocytes prior to contraction and is related to the sarcomere length. When venous return is increased to the heart, ventricular filling and hence preload (depicted in FIG. 17 as the left ventricular end-diastolic pressure (LVEDP)) increases. This stretching of the myocytes causes an increase in force generation which enables the heart to eject the additional venous return, thereby increasing the stoke volume (SV). Thus, increasing venous return and ventricular preload leads to an increase in stroke volume as shown in the FIG. 17. Frank Starling curves vary from heart to heart based on various factors, like contractility, wall stress, sphericity index, diseased state, etc. The curve that best matches a given patient may be obtained by comparing the patient specific characteristics to those of other patients in a database of other heart models (148, FIG. 3). FIG. 18 depicts an embodiment of a graph of pressure volume loops during a cardiac cycle.

Figure 19:
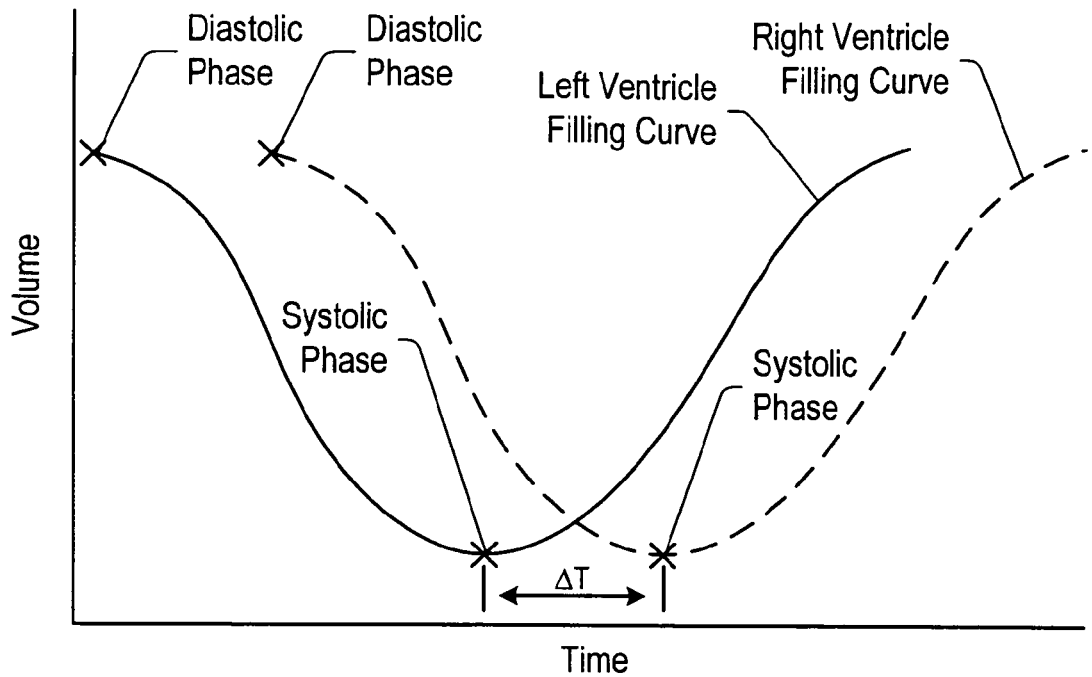
FIG. 19 depicts an embodiment of an example of a filling curve of a left ventricle and a right ventricle of a heart.

In an embodiment, a model or models may be used to assess a time gap between filling of a left ventricle and a right ventricle. EKG, currently used for this purpose, is an electrical measurement and may not accurately represent the mechanical function of the heart. In an embodiment, filling curves of the left ventricle and the right ventricle may be assessed using boundary images taken through a complete cardiac cycle (e.g., 10 shots of a heart). FIG. 19 depicts an embodiment of an example of a filling curve of a left ventricle and a right ventricle of a heart. The images may be used to assess a series of volumes for the left and right ventricles over at least one complete cardiac cycle. Time between systole (contraction) for the left ventricle and systole (contraction) for the right ventricle may be assessed. Measuring the time difference, $\Delta T$, between systole for the left ventricle and systole for the right ventricle using filling curves may measure the actual mechanical time between contractions of the ventricles. In a damaged heart, for example, the left ventricle may contract later than in a healthy heart and provide lower ejection power. If there is a difference in the timing between the contractions of the left and right ventricles, this may be an indication to a user that there is at least some akinetic or dyskinetic tissue. In an embodiment, accurately measuring the time gap may be used for better diagnosis of the need for biventricular pacing in a patient. Currently EKGs are used to assist users in diagnosing differences in the timing of left and right ventricular contractions, however EKGs have limitations. If a time lapse between ventricular contractions is relatively small (e.g., less than about 1 millisecond), an EKG may not be able to detect the time lapse while models created from image data may because the models are derived from mechanical data.

Figure 20:
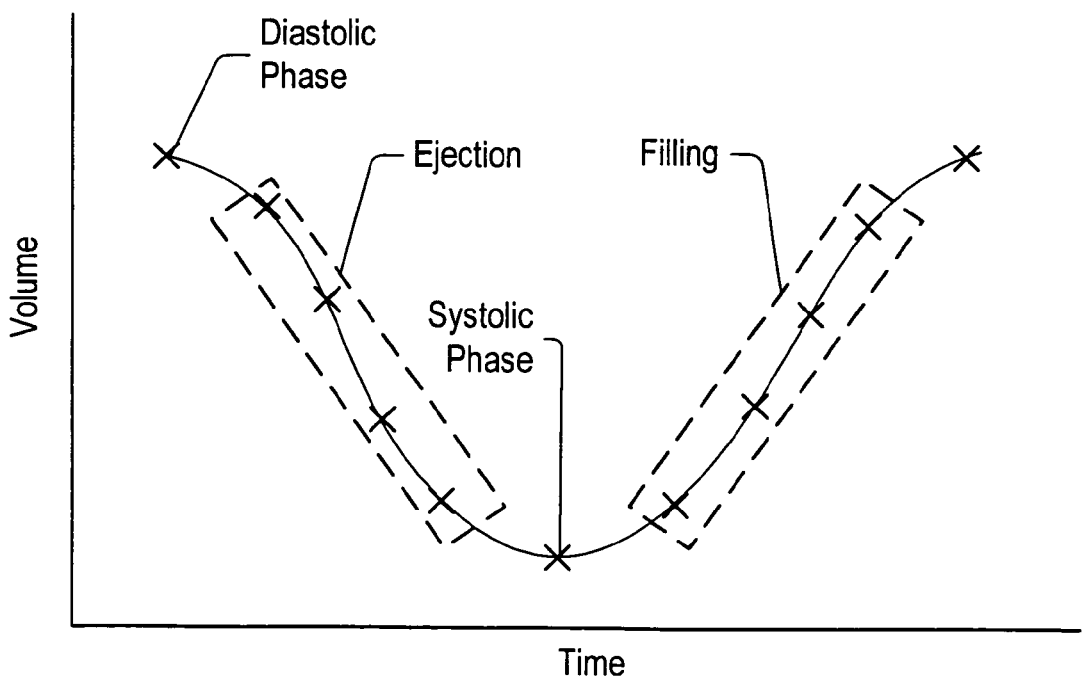
FIG. 20 depicts an embodiment of an example of a filling curve of a heart.

FIG. 20 depicts an embodiment of an example of a filling curve of a heart. Crosses represent data points from slices and/or images of the heart taken over a cardiac cycle. In some embodiments, a state of cardiac tissue may be assessed by determining a slope of a filling curve. The slope of the filling curve may be determined during diastole phase and may be used to assess a state of-the heart. For example, if the slope is relatively too small, then the heart may be having filling problems due to stiff muscle(s). In some embodiments, a slope of a filling curve may be used to evaluate how quickly a heart and/or a portion of the heart is ejecting fluids.

In some embodiments, a model or models may be used to assess a gap(s) in data associated with some medical imaging technology. Data missing from some medical imaging technologies may be extrapolated from the provided data to fill in gaps. For example, medical imaging technology (e.g., MRI) may gather data from at least one cardiac cycle of a heart. However, during the cycle the imaging device may include a trigger point at which no data is gathered. This trigger point may cause a lapse in gathered data of as much as 10% lost data. Using the data gathered by the imaging device, missing data from the cardiac cycle may be extrapolated. The missing data may be added to the model of the heart created. In an embodiment, missing data may be extrapolated by comparing and/or tracking the relationship between wall thickness of the heart and time. The relationship between time and wall thickness may not be linear; however, it may be used to extrapolate missing data.

Some medical imaging technologies (e.g., MRI) do not gather all of the images during the same heart beat or cardiac cycle. Images procured along a particular axis may not be taken at the same time as images along another axis are taken. For example, images of a two chamber view of the heart are not procured during the same cardiac cycle that images of a four chamber view of the heart are procured. Due to this factor, pictures along different axis of the heart may be misaligned relative to one another. This may be because of movement from the subject. Modeling software may make adjustments to compensate for this misalignment problem. In some embodiments, modeling software may fix an axis along which images were procured (e.g., a long-axis of the heart). Software may define points (e.g., the optimum points) along the images of the long axis images. Short axis images (which are not fixed) may be positionally adjusted relative to the fixed long axis images to minimize the cumulative distance between the theoretical (optimum) points on the planes and the actual points on the planes. Images may be continuously "jiggled" to minimize the cumulative distance (an optimum distance is zero but may not be obtainable).

Many times it may be helpful to combine data from various different medical monitoring technology. In some embodiments, heart models may be created by the superposition of various imagery data. For example, models of a ventricular structure (e.g., created from MRI) may be combined with models of blood vessel structure (e.g., from MRA (magnetic resonance angiography)). Combining these two models may allow for a more complete view of the state of a heart, allowing a user to view, for example, occlusions in vessels along with heart tissue problem. In some embodiments, there may be causal relationship between two occlusions in vessels and heart tissue problems. Data may also be combined from in other various medical technologies (e.g., CT scans and CT angio scans, and echo scans and angio scans).

A hemodynamic model, for example, has been developed and published by Professor Ying Sun, et. al., "A comprehensive model for right-left heart interaction under the influence of pericardium and baroreflex", The Amerimay Journal of Physiology, 1997, pp. H1499-H1514, which is incorporated herein by reference. The hemodynamic and physiological models may interact with the finite element model to show the user what effect his interaction has had on the other elements and/or the whole heart. Physiological models may vary from very simple, such as an equation of a curve of Stroke Volume vs. End Diastolic Volume as in the Frank-Starling curve (FIG. 17), to much more complicated computational biology models. Hemodynamic models may also vary from simple models of the pressure drop vs. flow relationship to complex computational flow dynamics like the one published by Makhijani et al. "Three-dimensional coupled fluid—Structure simulation of pericardial bioprosthetic aortic valve function", ASAIO Journal 1997; 43:M387-M392, which is incorporated herein by reference.

Figure 21:
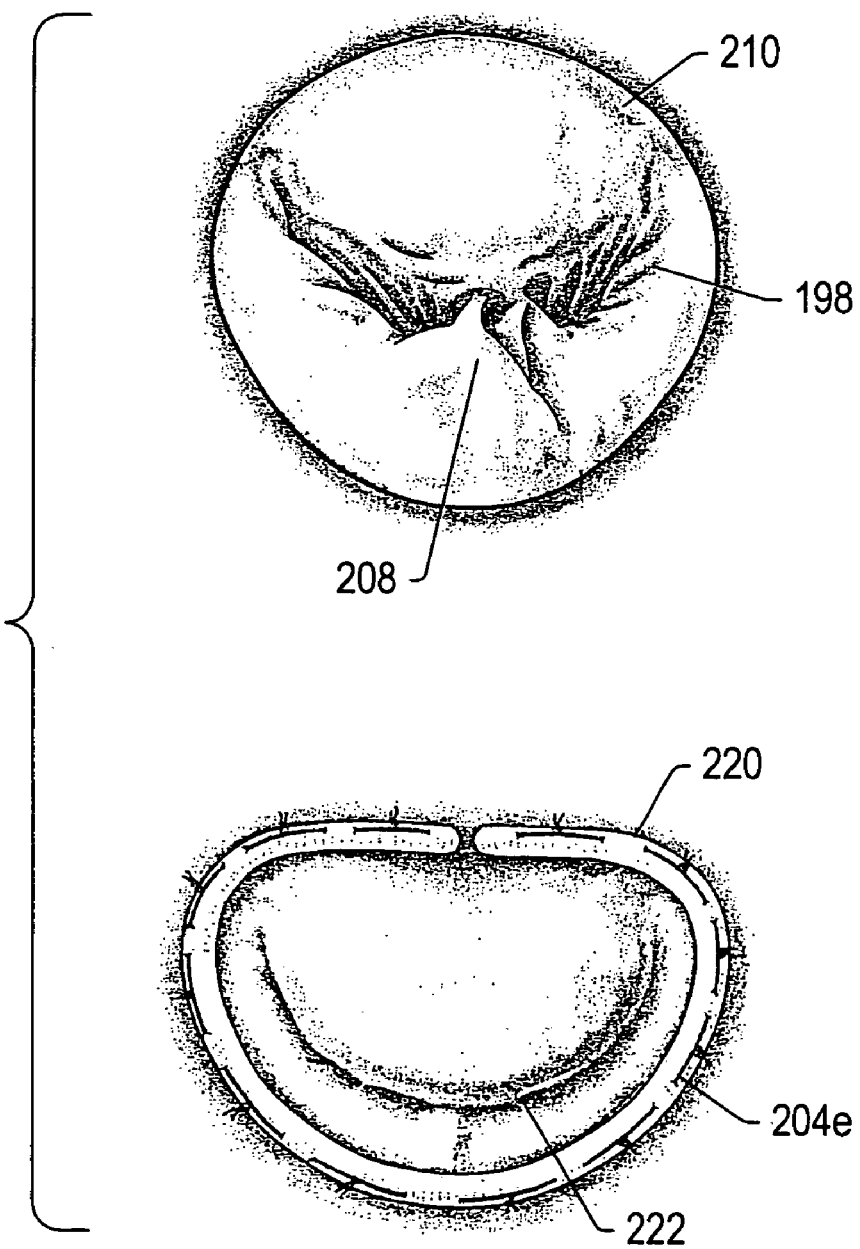
FIG. 21 depicts an embodiment of a mitral valve with an insufficiency and a valve after it is corrected with an annuloplasty ring.
Figure 22:
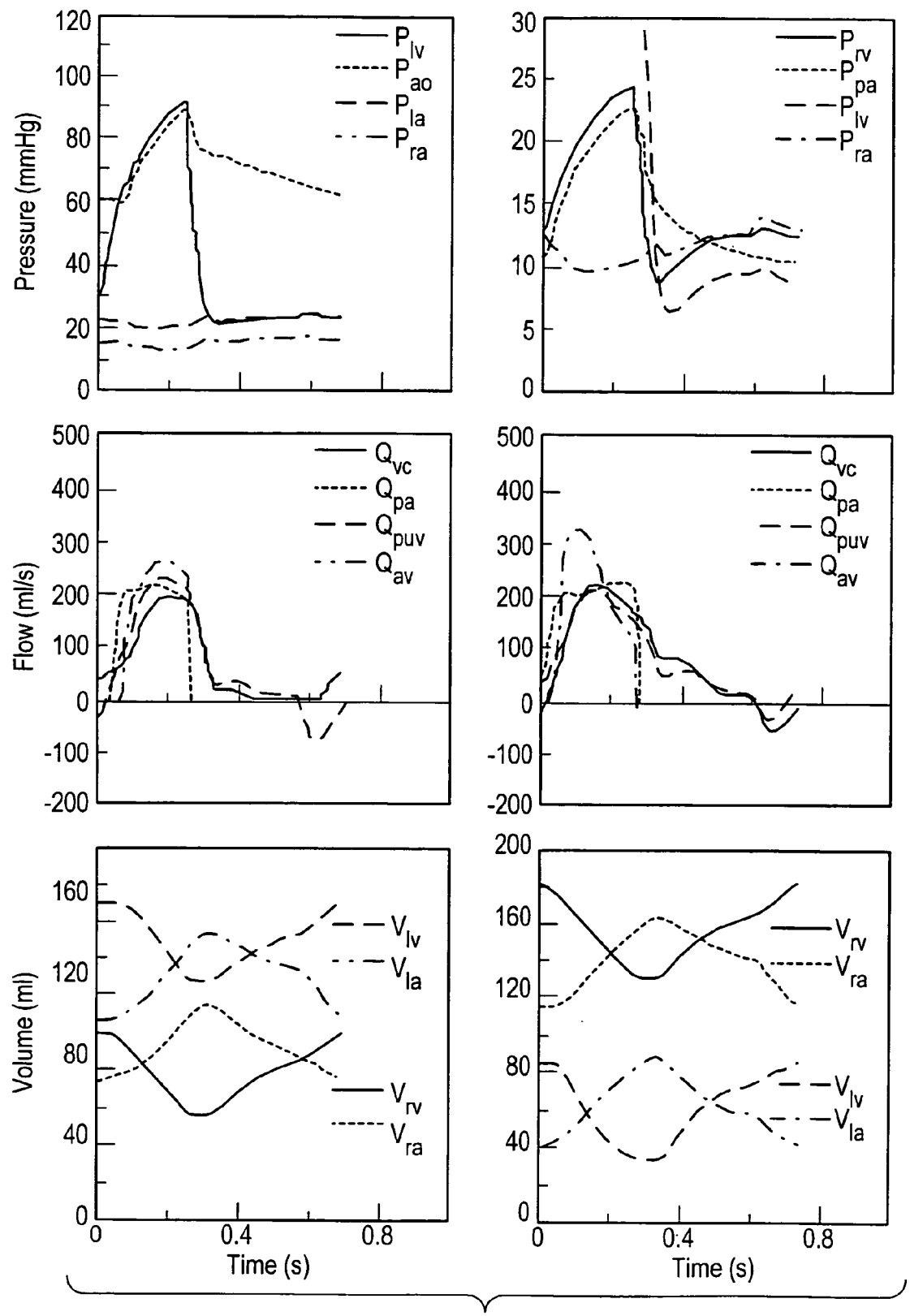
FIG. 22 depicts an embodiment of outputs from a hemodynamic model of a heart and circulatory system.

In an embodiment, a placement of an annuloplasty ring may be simulated to show its effect on annulus 198, connected tissue 208, and ventricle 210 (see FIG. 21). The patient's heart may be imaged (140). The image may be converted to a finite element model (142). Software may allow the user to select the type of treatment desired (144). The user may be able to access a database to select a device to be used (164). An annuloplasty ring would be an example of a device selected. The model may display to the user the mitral valve. The model may allow the user to instruct the model on where to position the ring. In some embodiments, a model may suggest where to position an annuloplasty ring based on a desired outcome of the procedure. The desired outcome may be indicated by the user. The model may assess which suture to use in securing the ring. The model may assess how much tension to put on the sutures. The model may assess a distance between each bite etc (146). The model may apply the intervention to the mitral valve annulus, the other elements of the mitral valve, the other components of the ventricle, and/or the heart as a whole (152). The software may recreate the image on the monitor to show the user the effects of his interaction (154). The potential clinical outcomes (156) may be assessed through use of the model and interaction with the physiological and hemodynamic models such as the graphs depicted in FIG. 22. In FIG. 22, hemodynamics for left heart failure are on the left and hemodynamics for right heart failure are on the right. $P_{lv}$—left ventricular pressure, $p_{ao}$—Aortic pressure, $p_{la}$—Left atrial pressure, $p_{ra}$—right atrial pressure, $p_{rv}$—right ventricular pressure, $p_{pa}$—pulmonary arterial pressure, $p_{ra}$—right atrial pressure, $q_{vc}$—flow through venacava, $q_{pa}$—flow through aortic valve, $v_{lv}$—volume of left ventricle, $v_{la}$—volume of left atrium, $v_{rv}$—volume of right ventricle, $v_{ra}$—Volume of right atrium. In an embodiment, a simulation may show an annuloplasty ring's effect on the size and/or orientation of the annulus. A simulation may show an effect the ring may have on the connected tissue, e.g., does it affect the length of the chordae tendinae, shape of the ventricle, etc. A model may be analyzed to show the surface area of the opening of the shortened annulus, how much flow may come through that opening, and/or how the change in flow may affect the ventricle. The model may predict if there is a mitral valve prolapse.

Figure 23:
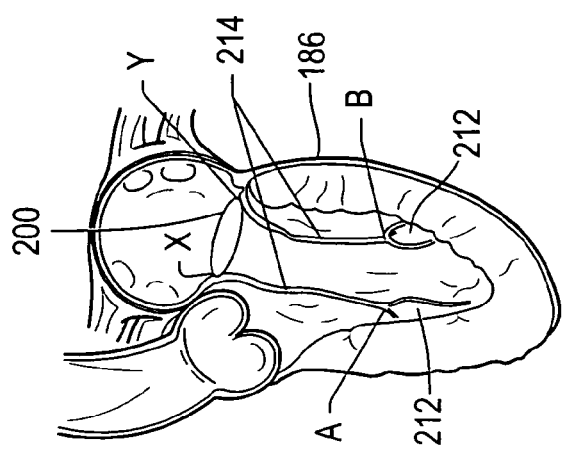
FIG. 23 depicts an embodiment of a cross-sectional view of a heart including papillary muscles and mitral valve.

FIG. 23 depicts an embodiment of a cross-sectional view of heart 186 including papillary muscles 212 and mitral valve 200. In an embodiment, a tether length of chordae 214 may be assessed using a computerized method based on, for example, MRI imaging. Chordae may not be typically visible using MRI methods, however, the mitral valve and papillary muscles typically are visible. In an embodiment, a model of a left ventricle may be created. A shortest distance between the tip of the posterior A or anterior papillary muscle B and the mitral annulus X and Y may be assessed. This shortest distance may be comparable to the tether length of the chordae. In some embodiments, these measurements may be performed in a 4-chamber or a 2-chamber view of the heart.

Figure 24:
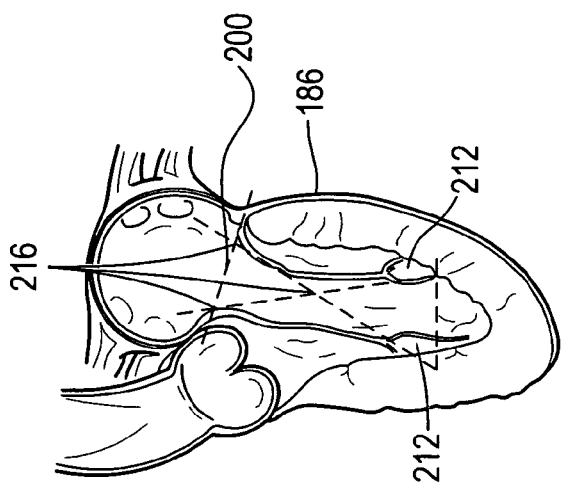
FIG. 24 depicts an embodiment of a cross-sectional view of a heart including papillary muscles and the mitral valve.

In an embodiment, a plurality of images (e.g., from an MI) may be provided to a computer system. At least a two-dimensional image along the y-axis may be extrapolated from the images provided to the computer system (depicted in FIG. 24). In certain embodiments, at least a three-dimensional image may be created from the plurality of images. A computer system may assess the position of one or both papillary muscles 212 in heart 186. The computer system may assess a point of intersection between one or both papillary muscles 212 and an endocardial wall using image enhancement and contrast identification as described herein. A computer system may assess points of intersection by comparing an image created by the computer system to a heart features database. A computer system may assess one or more angles 216 between one or more of papillary muscles 212 and mitral valve 200. In some embodiments, a user may virtually mark points of intersection on an image created by a computer system. The computer system may automatically calculate distances and angles from these reference points.

In an embodiment, a database of medical devices (for example, the devices depicted in FIGS. 21, 25, 26, 27, 28) may be created and accessed to allow the simulation of the devices. These devices may be tested for physical properties and the physical properties encoded into a finite element model, as has been done for elements of the heart described above. The finite element models for the devices may be stored in the database (164). The devices may be accessed by the user by selecting the object by its common name. For example, prosthetic valves and/or prosthetic valve apparatus (mechanical and bioprosthetic) may be called upon to place different artificial valves into the heart. The performance of the heart with the different valves may be assessed to select the correct valve for the patient. The model might also give estimated values of post-surgery performance of the heart. The model may display estimated ejection fraction, regurgitation, sphericity of ventricle, volume of the ventricle, percentage of shortening on the long and short axis, and maximum and minimum flows across the valves, and/or tension in chordae. In some instances, it is likely that off the shelf devices do not provide optimum results. For example, annuloplasty rings come in various sizes. It is likely that for a given patient, when a smaller size is used, the annuloplasty ring may end up creating more than acceptable tension in the chordae. Using the next size of the annuloplasty ring may lead to mitral insufficiency. In a situation where available sizes of the device are insufficient, the model may come up with a specification for the ring that falls between those two sizes. A patient specific designed device may offer the best possible outcome for the patient.

Figure 25:
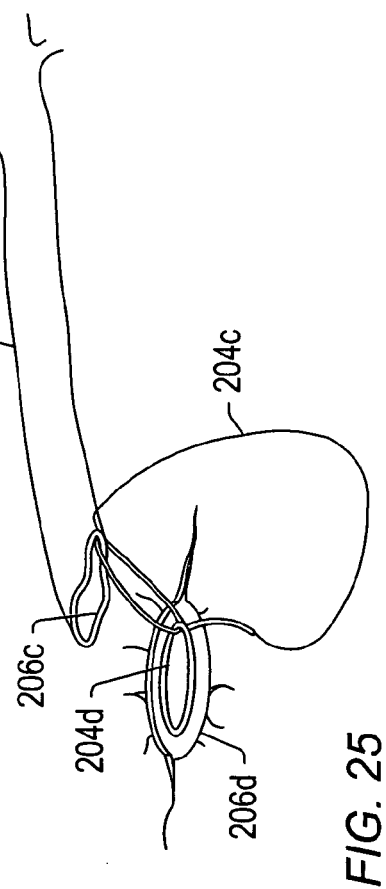
FIG. 25 depicts one embodiment of anastomosis.

FIG. 25 depicts one embodiment of a model of anastomosis in a heart. Anastomosis is generally defined as an opening created by surgical, traumatic, and/or pathological means between two normally separate spaces or organs. An anastomosis may be an artificially created connection between two structures, organs or spaces. It most commonly refers to a connection which is created surgically between two tubular structures, such as a transected blood vessel or loop of intestine. For example, when a segment of intestine is resected, the two remaining ends are sewn or stapled together (anastomosed), and the procedure is referred to as an intestinal anastomosis. Examples of surgical anastomoses are colostomy (an opening created between the bowel and the abdominal skin) and arterio-venous fistula (an opening created between an artery and vein) for hemodialysis. A pathological anastomosis may result from trauma or disease and may involve veins, arteries, or intestines. These are usually referred to as fistulas. In the cases of veins or arteries, traumatic fistulas usually occur between artery and vein. Traumatic intestinal fistulas usually occur between two loops of intestine (enetero-enteric fistula) or intestine and skin (enterocutaneous fistula). FIG. 25 depicts a virtual model wherein a tubular structure 218 (e.g., a vein) includes opening 206c. Openings 206d and 206c may be coupled with sutures 204c and 204d during an anastomosis.

FIG. 21 depicts one embodiment of a model of a mitral valve with an insufficiency and a virtual model of the valve after it is corrected with an annuloplasty ring. Annuloplasty may be generally defined as any of a variety of techniques that may be used to support or repair a valve after repair. The annulus is the outer border or limit of the valve structure. An annuloplasty supports that outer ring after repair. An annuloplasty ring is a particular embodiment of a support structure that may be used during an annuloplasty procedure. FIG. 21 depicts annulus 198, connected tissue 208, and ventricle 210. To correct the insufficiency, annuloplasty ring 220 may be coupled to ventricle 210 around the mitral valve. Annuloplasty ring 220 may be coupled to ventricle 210 using sutures 204e. Upon completion of the procedure, insufficiencies should be removed and result in corrected mitral valve 222.

Figure 26:
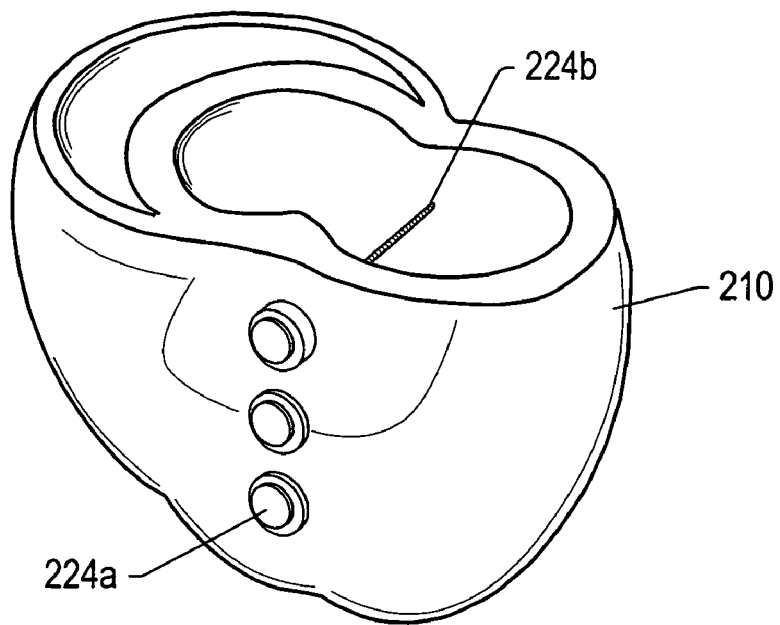
FIG. 26 depicts an embodiment of a placement of a Myocor splint.

FIG. 26 depicts one embodiment of a model with a Myocor splint. A Myocor splint essentially is a large suture that is used to create a Batista ventriculectomy-type exclusion of a portion of the left ventricle to improve left ventricular geometry and reduce wall tension. FIG. 26 depicts Myocor splints 224a and 224b positioned in ventricle 210.

Figure 27:
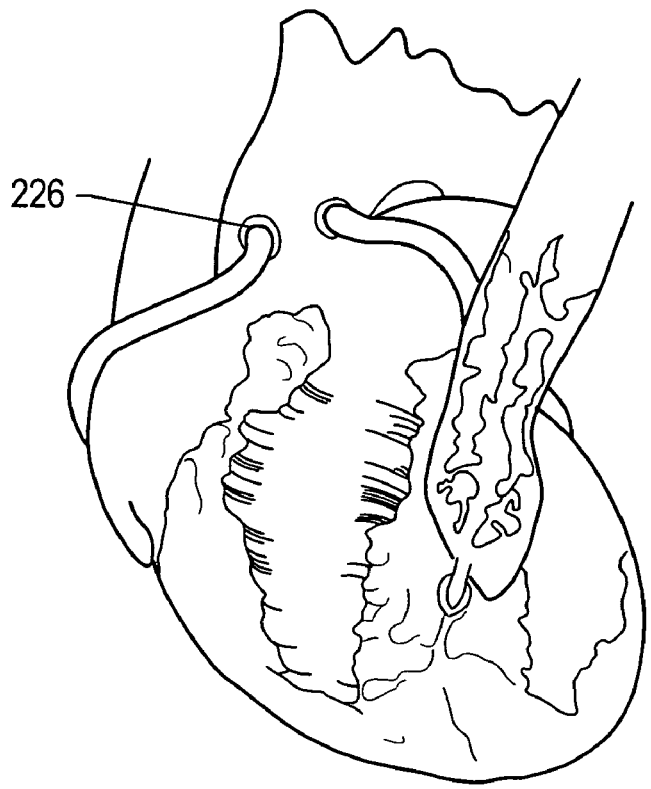
FIG. 27 depicts an embodiment of a mechanical heart valve.
Figure 28:
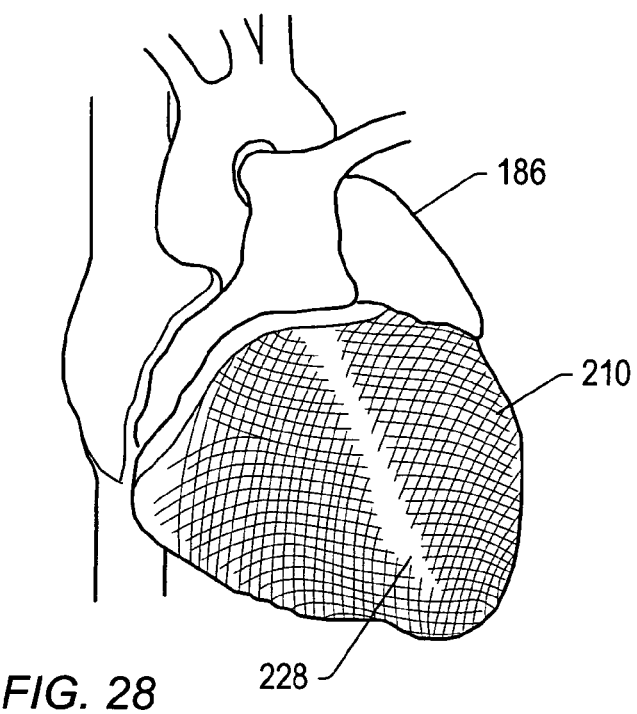
FIG. 28 depicts an embodiment of an acorn corcap.

FIG. 27 depicts a model of a mechanical heart valve 226. FIG. 28 depicts one embodiment of a model of an acorn corcap. Acorn corcap 228 may be positioned around ventricle 210 of heart 186 to prevent further dilatation and to reduce wall stress.

In an embodiment, a user may be able to enter specifications for a device in a database that is not quite appropriate for a specific patient. For example, a specification may call for a patch for a left ventricle. Patches for the left ventricle may exist in a database; however, an appropriate size may not be listed in the database. A user may enter specific specifications for a device (e.g., a patch) so that the device is closer to an appropriate size for a patient. In a situation where a device or instrument is already present in a database, a computer system may ask a user if the user desires to enter specifications different from specifications for the device currently in the database. If the user indicates a desire to enter in a new or different specification, the user may be prompted to enter data specifically tailored to that particular device. Although the computer system may be designed to automatically determine optimal specifications based on patient specific data entered, allowing a user to enter their own specification may allow for more flexibility. Advantages arising from this type of flexibility may include allowing a user to try different approaches to a procedure not outlined in an existing database. Other advantages may include assisting modeling software from becoming stuck in a local minimum of a modeling extrapolation. The flexibility of the software may be valuable as a training tool for cardiac interventions. The software may allow inexperienced surgeons to see effects virtually stemming from different approaches to conventional procedures.

In an embodiment, a method of assessing a surgical procedure on a human heart may include allowing a user to perform a modification to at least one feature of the heart using a computer system. The computer system may create an image of the modification. The created image may at least appear to be at least a three-dimensional image. A performance of the user may be assessed by comparing the user's modification to a database of modifications. The computer system may assess the performance of the user. The computer system may assign a score to the user's performance. The assigned score may be relative to other performances.

In an embodiment, a user may be able to enter specifications for an instrument or device not in the database. A computer system may allow a user to enter specifications for the device in a number of formats. In much the same way the system converts two-dimensional images into three-dimensional and higher images, the system may be able to convert two-dimensional images of devices into three-dimensional images and models of devices. A computer system may be able to extract the necessary data and specifications from two-dimensional images of a device to use in virtual modeling of a surgical procedure. Alternatively, a user may enter in a set of dimensions for the specific device.

Figure 29:
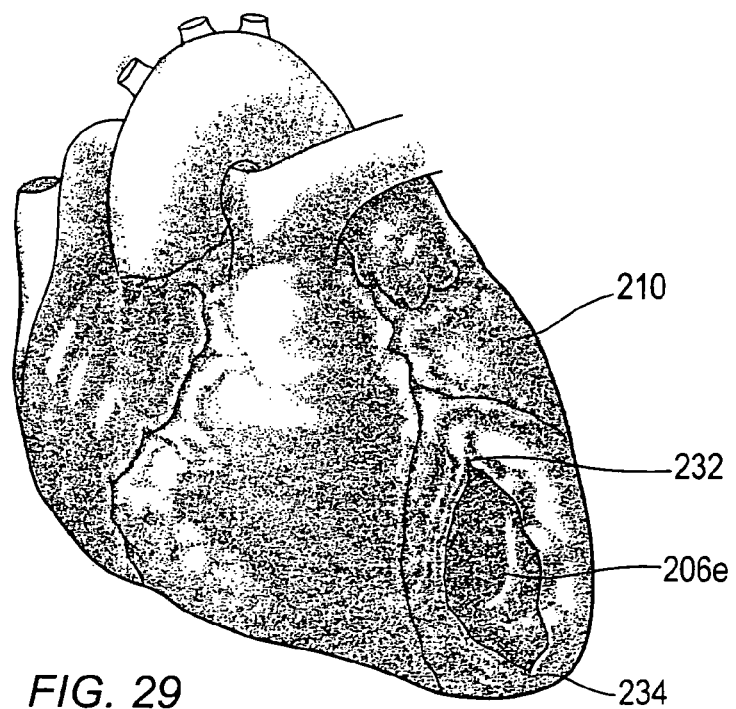
FIG. 29 depicts an embodiment of making an incision into a heart.
Figure 30:
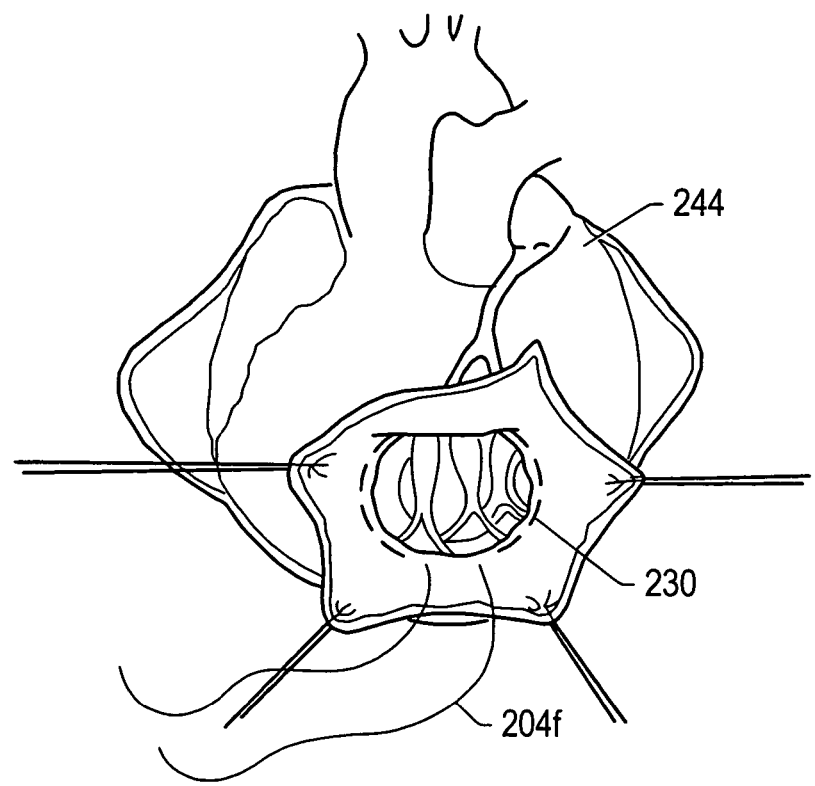
FIG. 30 depicts an embodiment of a Fontan Stitch—creation of neck for placement of a patch.
Figure 31:
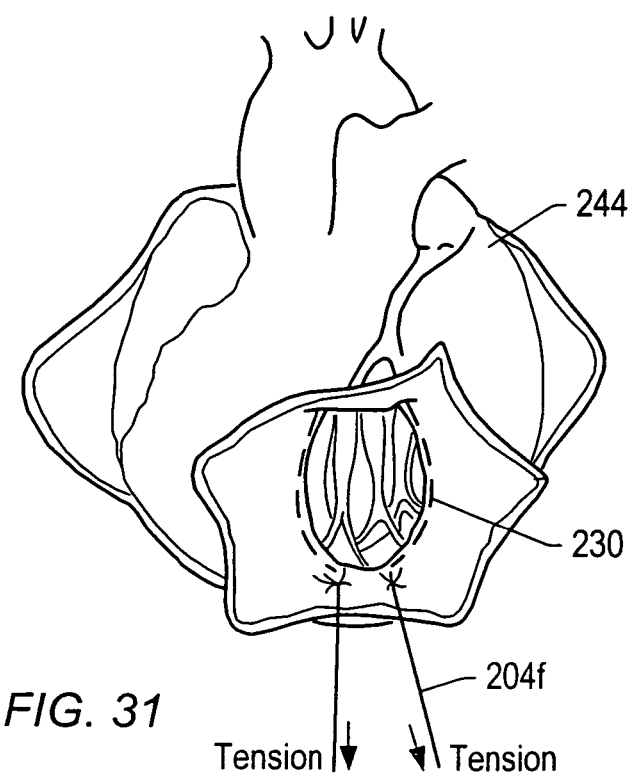
FIG. 31 depicts an embodiment of reforming a ventricle to give a new volume to the ventricle.

In some embodiments, the software method depicted in FIG. 3 may be used to model a surgical procedure. Images of a heart and specifically the ventricle are taken (140) and a finite element mesh model is created of the ventricle and of the features as described previously (142). A user chooses a treatment option (144) (e.g., surgical ventricular repair). The user, using pull down menus or another standard interactive means, chooses the implements that are needed to perform the surgical procedure (144). The user may perform the treatment by interacting with the image and the model (146). Interacting with the model, the user may, for example, select a scalpel. The surgeon may identify where and/or how to incise the ventricle with the selected scalpel (as depicted in FIG. 29). After a user makes an incision, the user then identifies the tissue he wants to exclude and may place a Fontan stitch 230 with suture 204*f*, as depicted in FIG. 30. When the user excludes tissue, the model eliminates the sections of the finite model that correspond to this area from the calculations of the ventricle parameters and outcomes. A model may keep these elements solely as graphical depictions. A model may try various degrees of volume reduction of the ventricle (FIG. 31) and/or changes in the shape of the ventricle. A computer system may attempt these types of reconstruction automatically and/or upon a request from a user. The finite element model may calculate this change in shape of the ventricle and calculate how this change has affected the other features of the ventricle and the heart.

Figure 32:
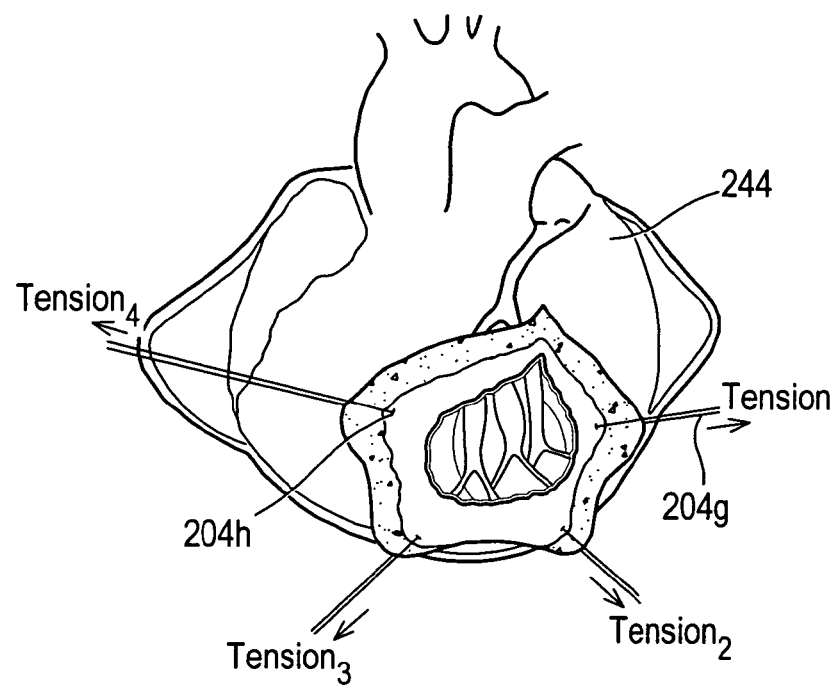
FIG. 32 depicts an embodiment of placing sutures and opening an incision in a ventricle.
Figure 33:
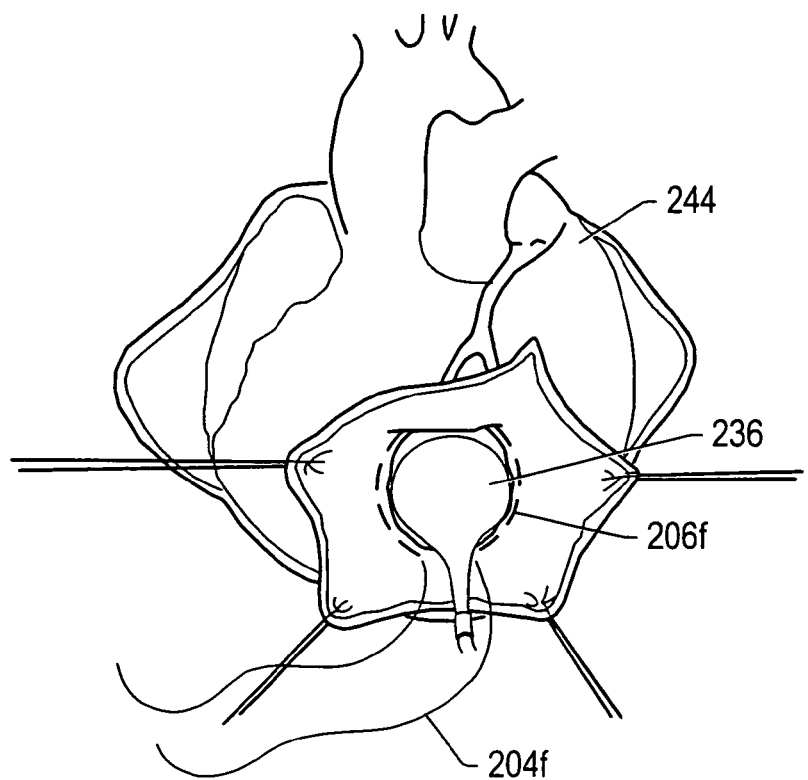
FIG. 33 depicts an embodiment of a sizing and shaping device placed into a ventricle.
Figure 34:
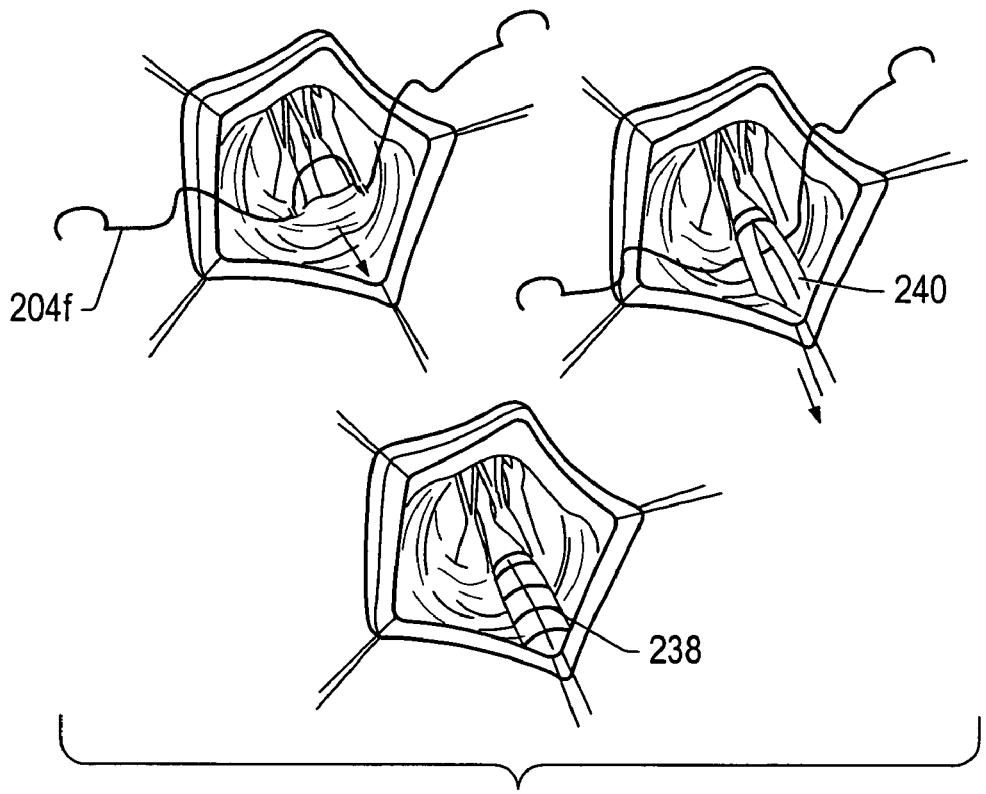
FIG. 34 depicts an embodiment of suture placement to imbricate stretched tissue.

FIGS. 29-34 depict embodiments of a sequence of a surgical procedure modeled on a virtual heart. The embodiment depicted is that of a left ventricle reconstruction. FIG. 29 depicts an embodiment of making an incision from point 232 to 234, thus forming opening 206*e* in ventricle 210. FIG. 32 depicts a placement of sutures 204*g* and 204*h* and opening up an incision in a ventricle during an actual surgical procedure. FIG. 33 depicts a representation of shaper 236 placed in opening 206*f* of ventricle 210. FIG. 33 depicts an example of how a ventricle is reconstructed during an actual surgical procedure. FIG. 30 depicts an embodiment of a Fontan Stitch. In one embodiment, during an actual surgical procedure, a surgeon may want to imbricate 238 stretched tissue 240 (as depicted in FIG. 34). During an assessment of a virtual procedure, a computer system may instruct a user what features of a heart could be modified to achieve the desired result including using such methods as depicted in FIGS. 29-34.

Figure 35:
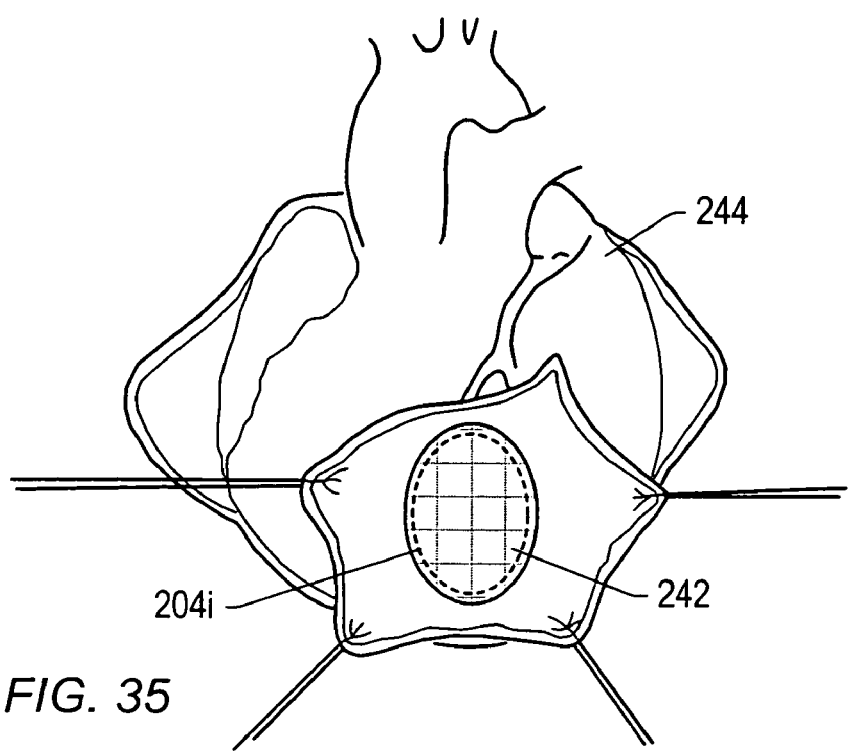
FIG. 35 depicts an embodiment of placement of a patch to close an opening in a ventricle.
Figure 36:
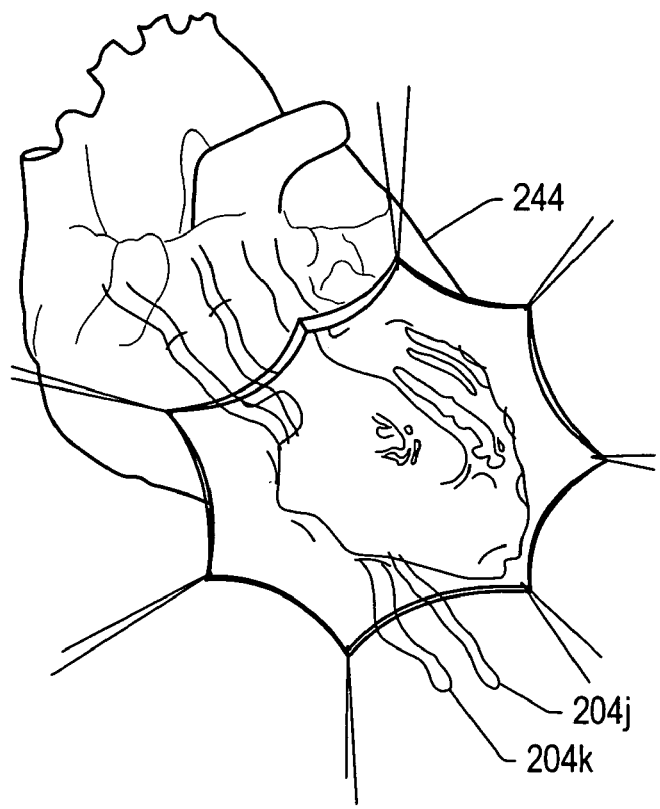
FIG. 36 depicts an embodiment of a buttress suture.

In an embodiment, as a model reshapes a ventricle to make it smaller, it may show the effect this has on other structures like the mitral apparatus. The model may show the new location of the papillary muscles, new angle of the chordae tendinae to the mitral annulus, etc. The finite element model may use known methods described herein to calculate the reaction of different features to changes in another element. For example, geometric alterations may in turn have effects on various other cardiac performance characteristics (e.g., smaller ventricles may have lower wall stress and may result in better contractility). A model may prompt a user to choose a patch to cover the opening that may be left in the ventricle and/or to reinforce the septum (see FIG. 35). FIG. 35 depicts an embodiment of a portion of a left ventricle reconstruction. FIG. 35 depicts patch 242 coupled with sutures 204*i* to left ventricle 244. If the opening in the ventricle is small (e.g., less than 3 centimeters), the model may tell the user to close the opening in the ventricle without a patch. The user may identify the suture placement locations as described previously and specify the amount of tension to be placed on the sutures. FIG. 36 depicts an embodiment of one type of suture: a buttress suture. Sutures 204*j* and 204*k* may be used to provide support to the heart. The model may depict the opening being closed with these sutures.

Figure 37:
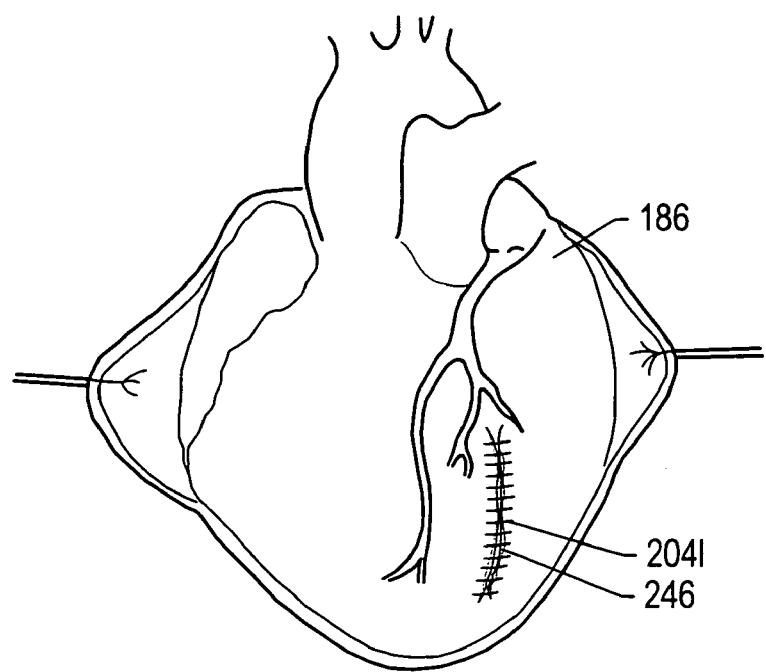
FIG. 37 depicts an embodiment of a linear closure of an opening in a heart.

In an embodiment, a model may accomplish a virtual closure of an opening by taking the boundary layers at the edge of the opening and moving them towards each other. When the boundary layers meet, the model recalculates the finite element model shapes that should depict the closure area. For example, if the finite element model is made of triangles, the triangles on the boundary layer may be smaller than the average triangle in the model. When the two smaller triangles on the boundary layers meet at the closure line, the smaller triangles may be combined into one average sized triangle. FIG. 37 depicts an embodiment of actual linear closure 246 of an opening in heart 186 using sutures 204*l*.

In an embodiment, a finite element model embodiment may interact with an outcome predictor (152). The outcome predictor may include a hemodynamic model, a physiological model, and other models for calculating features of the heart model. These models may interact until the physiological and hemodynamic models are within tolerances of known physiological and hemodynamic constraints and/or balanced in an acceptable manner. Known physiological and hemodynamic constraints may be part of a database (148). Known physiological and hemodynamic constraints may be based on an average gathered from different resources (e.g., cardiac surgery textbooks and journals). An acceptance criteria, in certain embodiments, may be a stroke volume index (SVI) selected to be between ~22 and ~50 ml/mt$^2$, a pulmonary artery pressure (PAP) selected to be within ~10 to ~25 mmhg, an ejection fraction selected to be above ~30%, and/or an end systolic volume index (ESVI) selected to be between ~25 and ~60 ml/mt$^2$. If after 50 attempts, for example, the models do not become balanced, the software may ask the user to alter his intervention. Once the models are balanced, the model may display the ventricle with the new shape and volume to the user. The computer system may display potential clinical outcomes such as ejection fraction, mitral regurgitation, etc. (154). The user may accept these clinical outcomes (156). If these outcomes are not acceptable, the user may return to the original model and image (158) to try a new treatment. The user may choose to modify the initial treatment with the model. The user may perform multiple iterations of the procedure. The user may compare clinical outcomes of multiple iterations of the procedure to determine which procedure is optimal for the patient. When the user accepts the intervention that is optimal for the patient, the model may create specifications (160) to help the user translate the simulated intervention to an actual procedure (162). The model may assess the size, shape and volume of the ventricle desired. The model may create a unique shaping and sizing device for the patient from this information to assist the user in performing the procedure.

Figure 38:
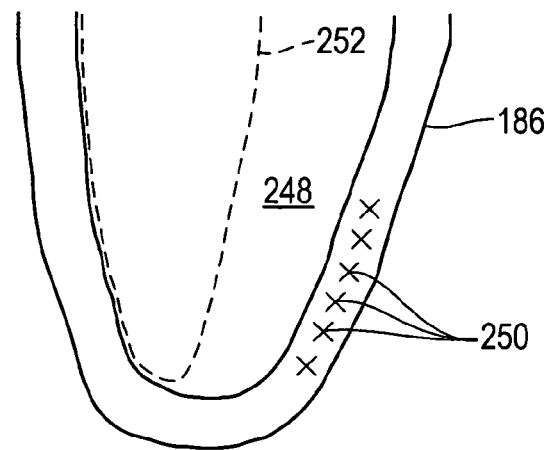
FIG. 38 depicts an embodiment of a proposed plication procedure.

In some embodiments, particular surgical procedures may be assessed by a computer system. One embodiment includes assessing a plication procedure (depicted in FIG. 38). At least one image may be provided to a computer system. A computer system may create at least a three-dimensional image of a heart. A user may modify interior chamber 248 (e.g., left ventricle) of the heart virtually. In an embodiment, a user may mark locations for proposed clips 250 on the image of heart 186. A computer system may assess a result of the proposed placement of clips 250. An image of a result of the plication procedure may be created by a computer system. For example, positioning clips 250 as depicted in FIG. 38 may result in interior chamber 248 of heart 186 being reconstructed into a shape indicated by demarcation line 252. In some embodiments, a user may virtually indicate on an image of a heart a final shape the user desires interior chamber 248 to take. A computer system may assess an optimal placement of clips 250 in heart 186 to achieve the user's desired goal.

In some embodiments, distances and angles between papillary muscles and other portions or features of a heart may be assessed using portions of an imaging method described herein. The positions and/or angles of papillary muscles to each other or to a mitral valve of a heart are useful indicators for assessing a condition of a heart. One problem with current imaging technology (e.g., MRI) is that it is difficult to determine the exact point of intersection of one or both papillary muscles. This difficulty arises from the problems of most imaging techniques in obtaining an image of the point of intersection of a beating heart.

In an embodiment, a plurality of images (e.g., from an MR) may be provided to a computer system. At least a two-dimensional image along the y-axis may be extrapolated from the images provided to the computer system (depicted in FIG. 24). In certain embodiments, at least a three-dimensional image may be created from the plurality of images. A computer system may assess the position of one or both papillary muscles 212 in heart 186. The computer system may assess a point of intersection between one or both papillary muscles 212 and an endocardial wall using image enhancement and contrast identification as described herein. A computer system may assess points of intersection by comparing an image created by the computer system to a heart features database. A computer system may assess one or more angles 216 between one or more of papillary muscles 212 and mitral valve 200. In some embodiments, a user may virtually mark points of intersection on an image created by a computer system. The computer system may automatically calculate distances and angles from these reference points.

Figure 39:
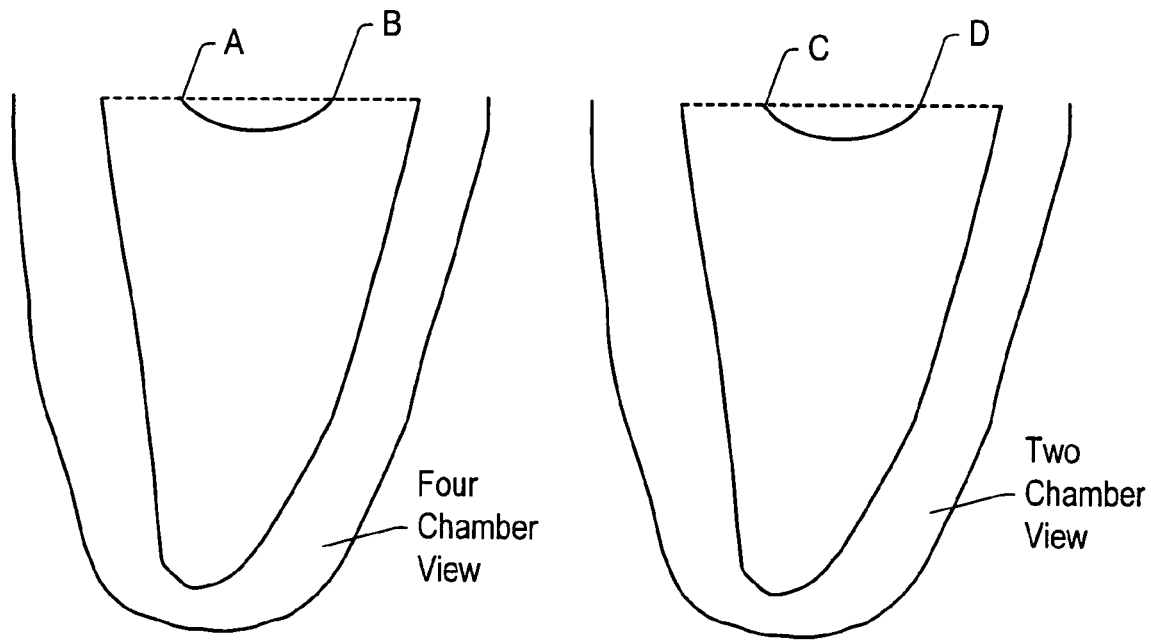
FIG. 39 depicts an embodiment of a pictorial representation of a cross-sectional view of a two chamber and a four chamber views of a heart including a mitral valve.

FIG. 39 depicts an embodiment of a pictorial representation of a cross-sectional view of a two chamber and a four chamber views of a heart including a mitral valve. In an embodiment, a plurality of images (e.g., from an MRI) may be provided to a computer system. From the provided images a model of a heart may be created. From the provided images and/or created model, a mitral valve orifice area may be determined. In an embodiment, two points C and D of ends of a mitral valve from a two-chamber view of the heart and two points A and B from a four-chamber view of the heart are obtained from the plurality of images. A splice may be run around the four points to get the mitral valve surface. From the mitral valve surface, the orifice area (e.g., the area of the saddle formed from the four points) may be determined. In an embodiment, a user may be able to use rotational MRI to get a better idea of a shape of the saddle (by using more points). A size of the orifice area may be calculated when mitral valve is open by determining the size of the orifice area during diastole.

Figure 40:
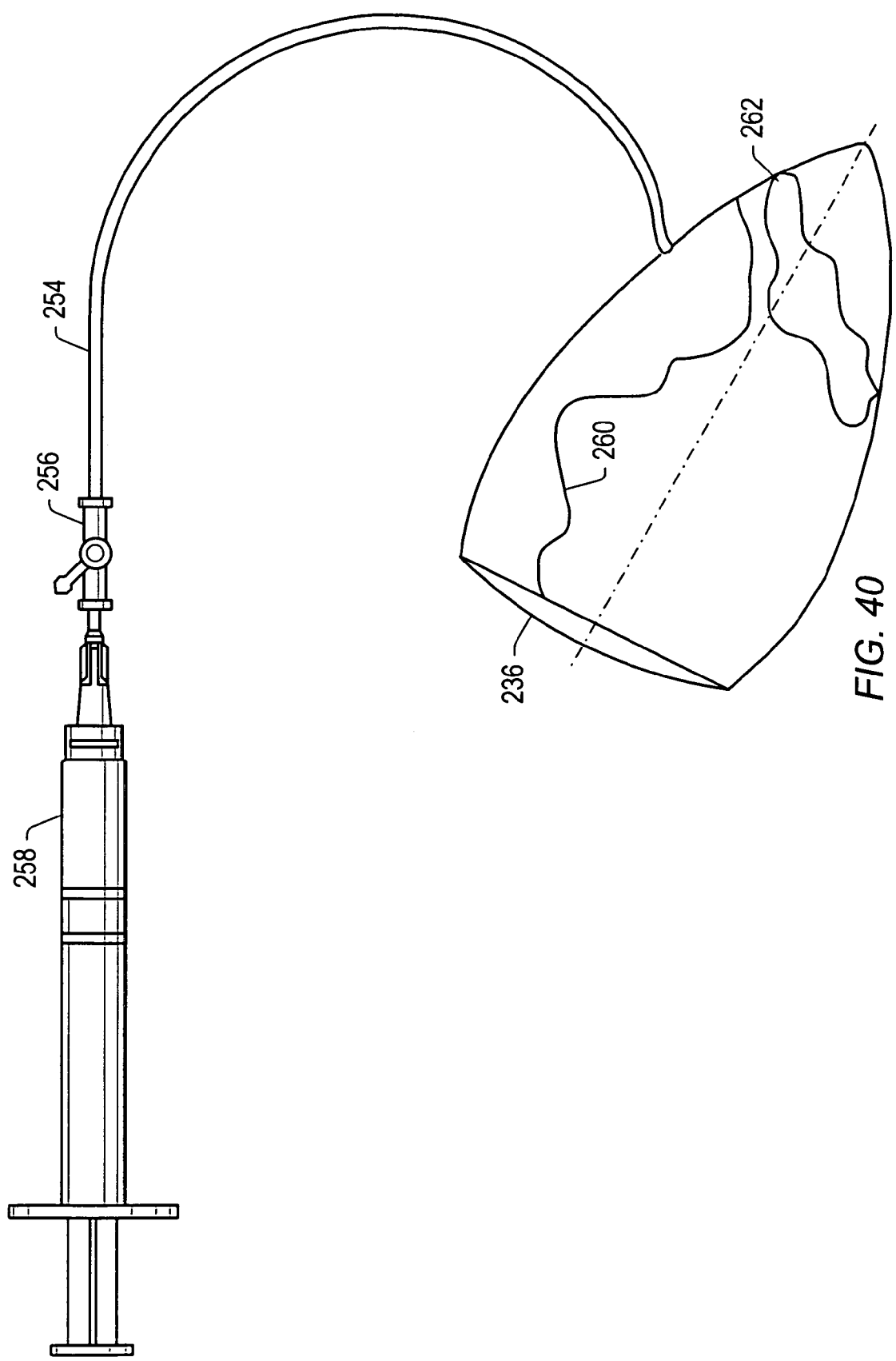
FIG. 40 depicts an embodiment of a sizing and shaping device with a location of a diseased area of a ventricle marked on its surface.

In an embodiment, a method to design surgical instruments and/or reconstruction devices based on a patient specific image of a heart may be accomplished by a computer system. For example, a method to make a custom sizing and shaping device may include generating a 3D CAD file (e.g., DXF or STL formats) that has the outline of the interior of the ventricle. A 3D CAD file may be loaded into a CNC milling machine. This machine may take the file and create a three-dimensional mandrel from the file. This mandrel may be dipped in a number of solutions such as plastisol and urethane to form a pliable balloon like object that may be taken off the mandrel. A cap of similar material may be added to the top of the shaping device. A tube for filling the shaping and sizing device with fluid may be added. FIG. 40 depicts an embodiment of a sizing and shaping device with a location of a diseased area of a ventricle marked on its surface. Shaping device 236 may be fluidly connected to elongated member 254. Elongated member 254 may be coupled to lock 256. Lock 256 may function to keep the pressure of a fluid injected into shaper 236 at a particular pressure. Fluid reservoir 258 (e.g., a syringe) may be coupled to lock 256. Fluid reservoir 258 may function to contain the fluid (e.g., a liquid or a gel). Fluid may be injected into shaping device 236 to expand shaping device 236 to a predetermined shape. Shaping device 236 may include demarcation lines 260 and 262. Demarcation lines 260 and 262 may indicate the location of a diseased area for use as a reference during an actual surgical procedure.

Figure 41:
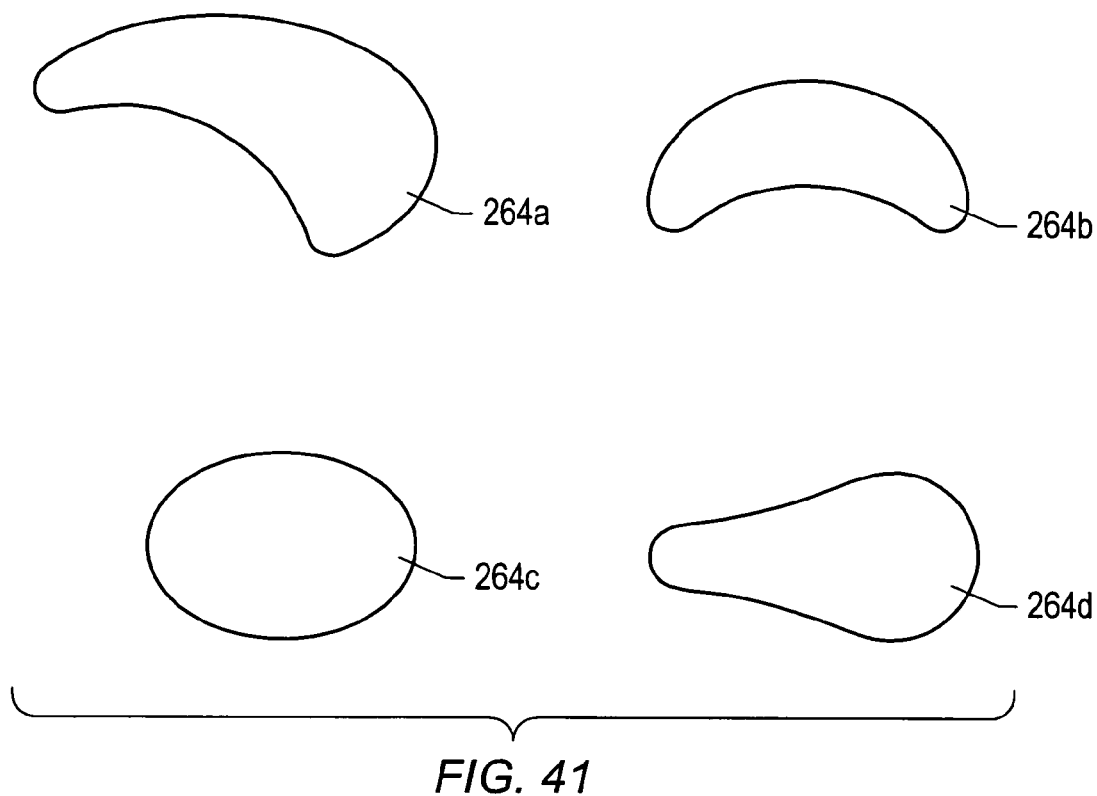
FIG. 41 depicts an embodiment of various potential patches of different sizes and shapes to seal an opening in a ventricle.

In an embodiment, an optimal solution to reconstruct a ventricle may require the use of a patch to reinforce a septum and/or close a hole remaining in the ventricle. A model may be able to show the user what shape patch may be needed to perform the ventricular reconstruction. A specially constructed patch may be made for a patient. A method to manufacture a patient specific patch could be to purchase cardiovascular patches sold by, for example, Boston Scientific/ Meadox, or W. L. Gore and Assoc. The model may generate a CAD file defining the shape of the opening in the ventricle. The shape of the opening may be printed and used as a template. The template could be placed on a patch and the patch cut to the patient specific shape and then sterilized. FIG. 41 depicts embodiments of various potential patches 264a-264d of different sizes and shapes to seal an opening in a ventricle. The model may lead to other tools that help the user implement the solution that the model has created (e.g., a patch with an apex).

Figure 42:
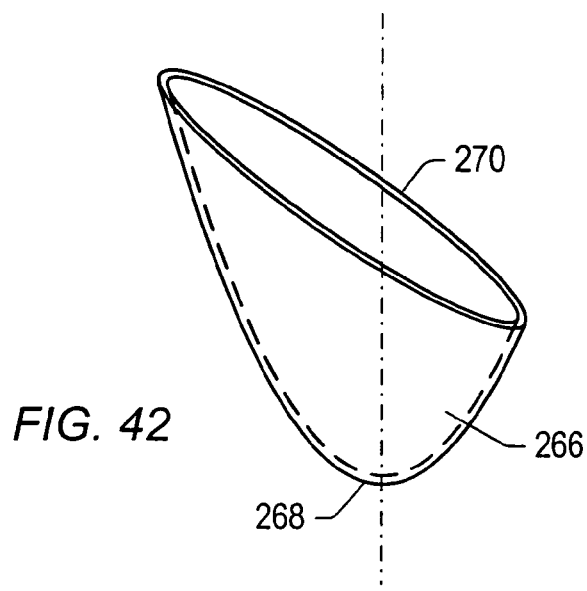
FIG. 42 depicts an embodiment of a patch that has an apical shape.

FIG. 42 depicts an embodiment of a patch that has an apical shape. Apical patch 266 may include tip 268 (e.g., an apex) and base 270. Apical patch 266 may include a concave interior surface that may function as at least a portion of the interior surface of a reconstructed ventricle. Apex 268 may function as the new apex of a reconstructed ventricle.

In an embodiment, an alternate or concurrent method may be to assess a cardiac treatment. A cardiac treatment may be assessed by constructing a patient specific model using a computer system. Specific goals may be entered by the user such as a particular size and/or shape of a left ventricle or a value for an ejection fraction. A computerized method may assess different strategies and/or procedures for achieving entered goals. The computer system may make recommendations for an optimal treatment of a diseased heart to achieve the desired goals or entered parameters. As an example of this strategy, a way of doing an SVR procedure is to start with a desired volume of the ventricle and selecting a ventricle sizer. The model may interact with the computational model of the ventricle sizer. These operations are similar to those mentioned earlier, except that the ventricle is formed over the ventricle sizer. The output of the model may be a patient specific, unique shaped patch needed to perform the intervention.

In certain embodiments, a model may interact with finite element models of many currently marketed devices such as, but not limited to: the Myocor Inc. Myosplint, depicted in FIG. 26; the Acorn Inc Corcap, depicted in FIG. 28; or a biventricular pacing device from either Medtronic or Guidant. These devices and other commercially available devices may be converted into a computer model and added to a database. In each case, the model may produce outcomes of interventions using these devices. If the user likes the outcomes, then specifications may be produced in order to transfer the results of virtual surgery to real surgery. In some instances, specific tools or devices may be generated. The user takes these tools, devices, and or specifications and conducts the procedure. In some embodiments, templates may be printed (in two-dimensional embodiments) or manufactured (in, for example, three-dimensional embodiments). Templates may assist a user by guiding the user through a specific procedure or cardiac intervention. A template may be "life size" (i.e., having the same dimensions as the model) or image constructed from data for a specific patient provided to a computer system.

Figure 43:
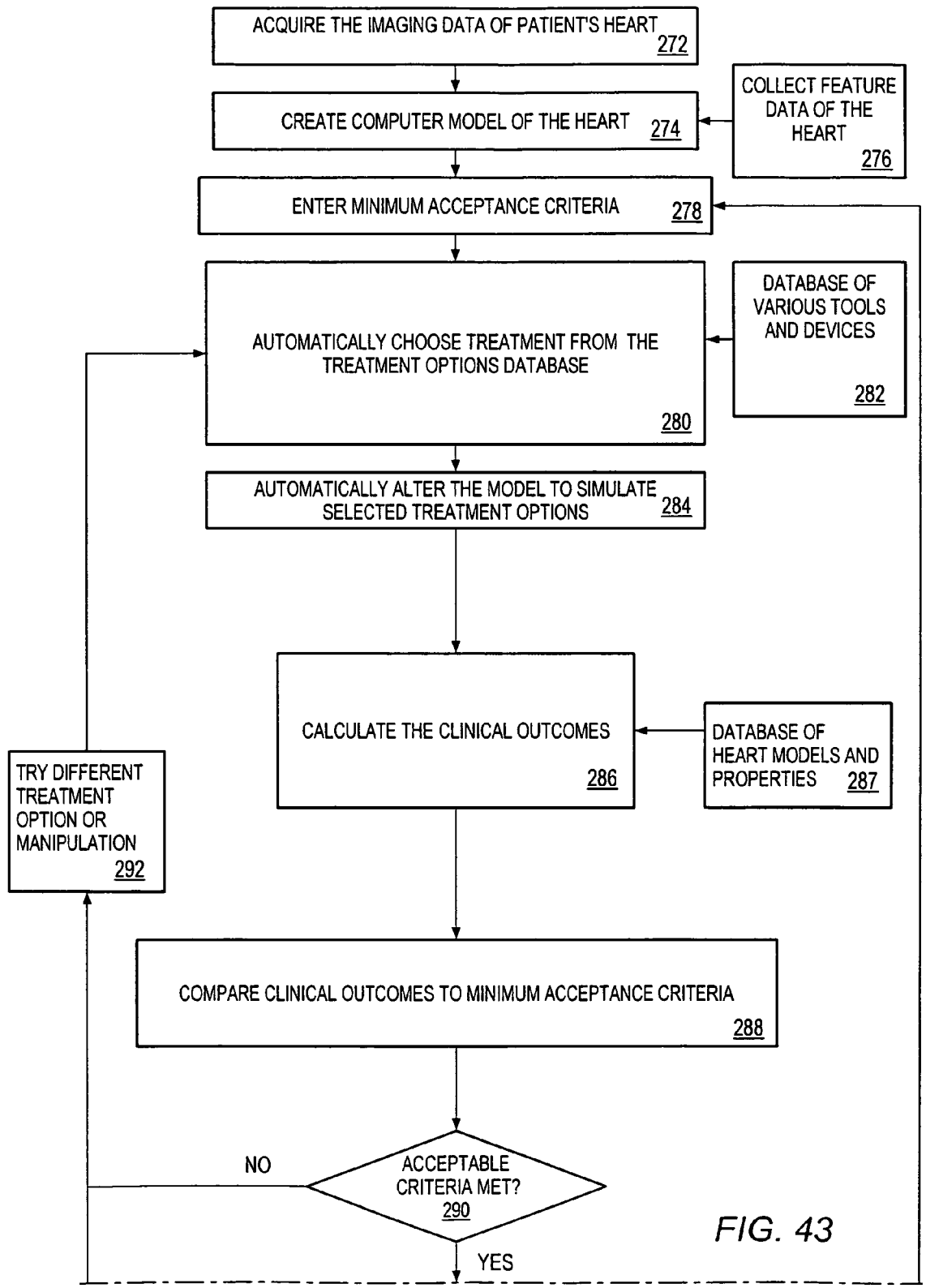
FIG. 43 depicts a flowchart illustrating an alternate embodiment of a method of a cardiac intervention.
Figure 43:
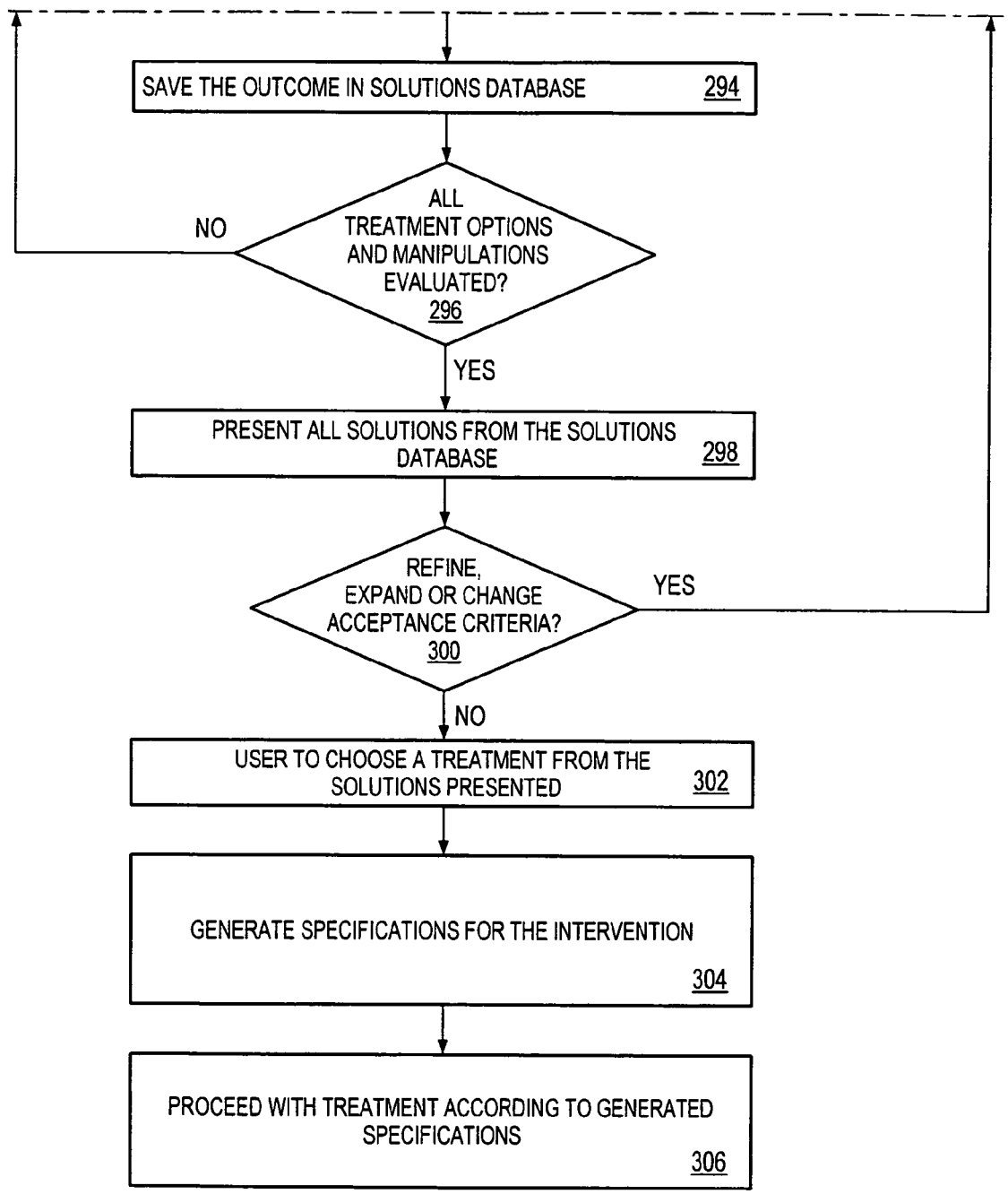

A method of modeling an intervention procedure may be performed in an automatic mode, as shown in FIG. 43. A user could simply input a desired outcome or outcomes such as a defined ejection fraction range, ventricle volume range, etc. Software may run numerous iterations of all the different types of treatments to produce expected treatment options that meet defined criteria for that particular patient. The results may be ranked to allow the user to select the best treatment with the best outcome. In some embodiments, software may run and supply the best possible outcome without any input from a user besides the required data to run the software. In some embodiments, software may report to the user that the desired outcome from a specific treatment is not possible and thereby force the user to reconsider his selection criteria options.

FIG. 43 depicts a flowchart of an automated method for determining a treatment for a cardiac condition. The method begins with acquiring image data of the heart (272). Image data may be collected using a variety of imaging technologies that include, but are not limited to, MRI imaging, echocardiography, or PET. These imaging systems are common in most hospitals and the leading manufacturers of these systems are General Electric, Siemens, and Phillips. Additional features of the patient's heart may also be collected (276) as has been described previously.

Some or all of these features may be used to create a computer model of the patient's heart (274). In some embodiments, a computer model of the heart is a multi-dimensional finite element computer model, as described previously. Software producing the model may run on a personal computer or at a central location accessible by one or more personal computers. The computer model may be produced using a computer at one location and delivered to a different computer at another location.

A set of acceptable physiological and hemodynamic criteria may be entered in a computer model (278). Acceptable criteria include, but are not limited to, a stroke volume index, a pulmonary artery pressure, an ejection fraction and/or an end systolic volume index. The acceptable criteria may be entered by a user or may be selected by the software based on information collected about a patient.

Software may perform an analysis of the functioning of a heart and the properties of the various components of the heart to make a diagnosis of the heart condition. Based on the diagnosis of the heart the software may choose one or more treatment options (280).

After the software has selected a treatment option, the software may automatically adjust the computer model of the patient's heart (284) to simulate the proposed treatment of the heart. The computer software, in one embodiment, may include a database (282) that includes computer models of a variety of tools and devices that may be used for a variety of treatments. Adjusting the computer model of the patient's heart may involve importing one or more of these tools or devices into the computer model from the database (282).

The computer model may be used to analyze what effects a selected virtual treatment may have on a patient's heart. The insertion of cardiac devices or the performance of a surgical technique may alter the geometry of a patient's heart. The modeling software may alter the model of the patient's heart (284) in response to the selected treatment. Additionally, the computer software may automatically determine the effect of the treatment on various features of the patient's heart (286). For example, the software may calculate physiological properties of the heart based on known properties of hearts. The results of these calculations may be used to create a new model of the patient's heart.

After the modifications have been performed on the heart, the software may assess if the modified heart meets the selected or entered minimum acceptable criteria (288). If the modified heart model does not meet these criteria, the software may alter the proposed treatment or select a different treatment (292). The altered or new treatment may be used to create a new model. This process may be repeated until the properties of the heart as modified by the selected treatment meet the minimum acceptable criteria (290).

After the minimum acceptable criteria have been met, the treatment and model of the heart after performing the treatment may be saved in an outcomes database (294). The outcomes database may include one or more potential treatments to remedy the diagnosed heart condition. An advantage of using an automated system is that all treatment options may be evaluated. Thus, after a treatment has been saved into the outcomes database, the software may assess if all treatment options have been evaluated (296). If alternate viable treatments have not been evaluated, the software may select one of the alternate treatments for evaluation. Evaluation of this alternate treatment may use the same iteration process described above to determine if any useful outcomes may be developed by alternate treatment. Any acceptable outcomes may also be stored in the outcome database. In an embodiment, the process may be repeated until all viable treatment options have been evaluated.

After at least a portion of the automated analysis has been completed, software may indicate to the user that treatment options have been determined (298). The user may access these treatment options and use the displayed information to diagnose the outcome of the proposed treatment on a patient's heart (298). Diagnosing the effect of the procedure on a cardiac irregularity (including, but not limited to, structural, chemical, and/or electrical irregularities) may include comparing the simulated computer model of the outcome of the treatment to what is generally accepted to one skilled in the art as a healthy/normal heart. Cardiac treatments may be assessed/determined by analysis of a model of each procedure (procedure not being limited merely to a surgical procedure). Treatments may also be assessed relative to a database of heart models 287. The database of heart models may include, but is not limited to, data from prior cardiac surgical procedures and/or treatments, expert opinions (e.g., cardiac surgeon specialist's opinion), and/or data derived or extrapolated from prior cardiac surgical procedures/treatments or expert opinions.

In some embodiments, software may not be able to find outcomes that meet the minimum acceptable criteria set forth by the user or the software. In some embodiments, the proposed treatments and the outcomes selected by the software may be unacceptable to the user. In either case, the user may decide to alter the minimum acceptance criteria (300). Altering the criteria may include expanding the range of acceptable parameters. Altering the minimum acceptable criteria may restart the automatic iterative process of determining a potential treatment.

After one or more outcomes have been generated, the user may access the outcomes database to determine if the outcomes are acceptable (302). When the user accepts one of the potential clinical outcomes, the model may produce specifications for the selected treatment (304). These specifications may lead to the development of a template for or tools or devices to guide the user in translating the virtual intervention on the model to the actual intervention on the heart (306). Tools and devices may include cardiac instruments such as ventricle patches, ventricle shapers, and sizers. A computer system may assist in designing cardiac instruments using the images as a model to produce patient specific devices. In some cases, templates, tools, or devices may not be needed to perform the intervention and specifications. Additional devices may be generated from the models to help the user implement the surgical procedure that the model has predicted to provide the best outcome.

Figure 44:
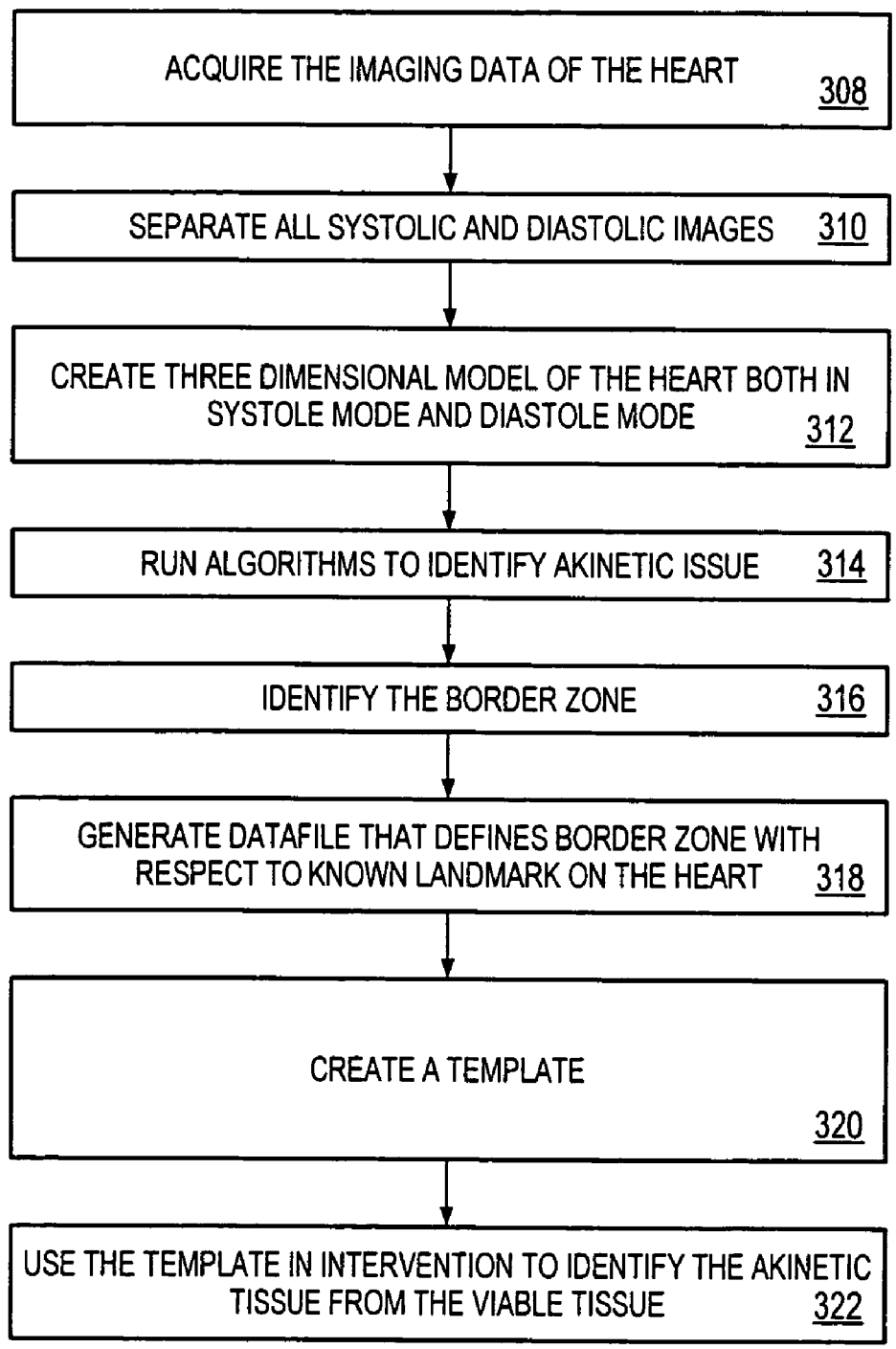
FIG. 44 depicts a flowchart illustrating an alternate embodiment of a method of a cardiac intervention.

A process for determining the akinetic segments of a patient's heart is depicted in FIG. 44. Before treatment, in order to assess which areas of the heart may need to be repaired or replaced, the patient may undergo an imaging procedure such as an MRI scan, PET scan, or an Echocardiography scan to determine the location and condition of the components of the heart. Initially, imaging data is collected of the patient's heart (308). Since the images are captured of the patient's heart while it is beating, the stage of beating that the heart is in is taken into account when creating a model of the heart. In one embodiment, the systolic and the diastolic images of the patient's heart are separated (310). These separated images may be used to create separate, three-dimensional models of the heart in systole mode and diastole mode (312). In an embodiment, a variety of different algorithms may be used to identify akinetic tissue (314). Borders of the akinetic tissue may be identified (316). The borders may be identified within a multi-dimensional model of the heart.

In an embodiment, the patient's current ventricular anatomical landmarks may be determined by manually tracing the epicardium and endocardium. In certain embodiments, the patient's current ventricular anatomical landmarks may be determined by automated border detection software, which may quickly outline the location of different structures within the ventricle from the imaging data (318). This information may be converted into a multi-dimensional picture of the heart that may include all valves, arterial and venous structures of the heart (320). Parts of the valve apparatus, which may not fully appear with the automated border detection software (e.g., chordae tendinae) for example, may be quickly hand traced to complete the four-dimensional dataset. The multi-dimensional image may show regurgitation across the valves using different color gradients to show severity, as is currently done with echocardiography.

One of the problems surgeons confront while doing an SVR procedure is how to determine the demarcation line between viable and akinetic tissue. For this purpose, a non-interactive model, which may show the location of a diseased area of the ventricle (322), may be developed using a method as shown in FIG. 44. The model may show on the image areas of the ventricle that are akinetic or dyskinetic to determine areas that might be excluded during an SVR procedure. A variety of different algorithms may be used to identify akinetic tissue (314).

Figure 45:
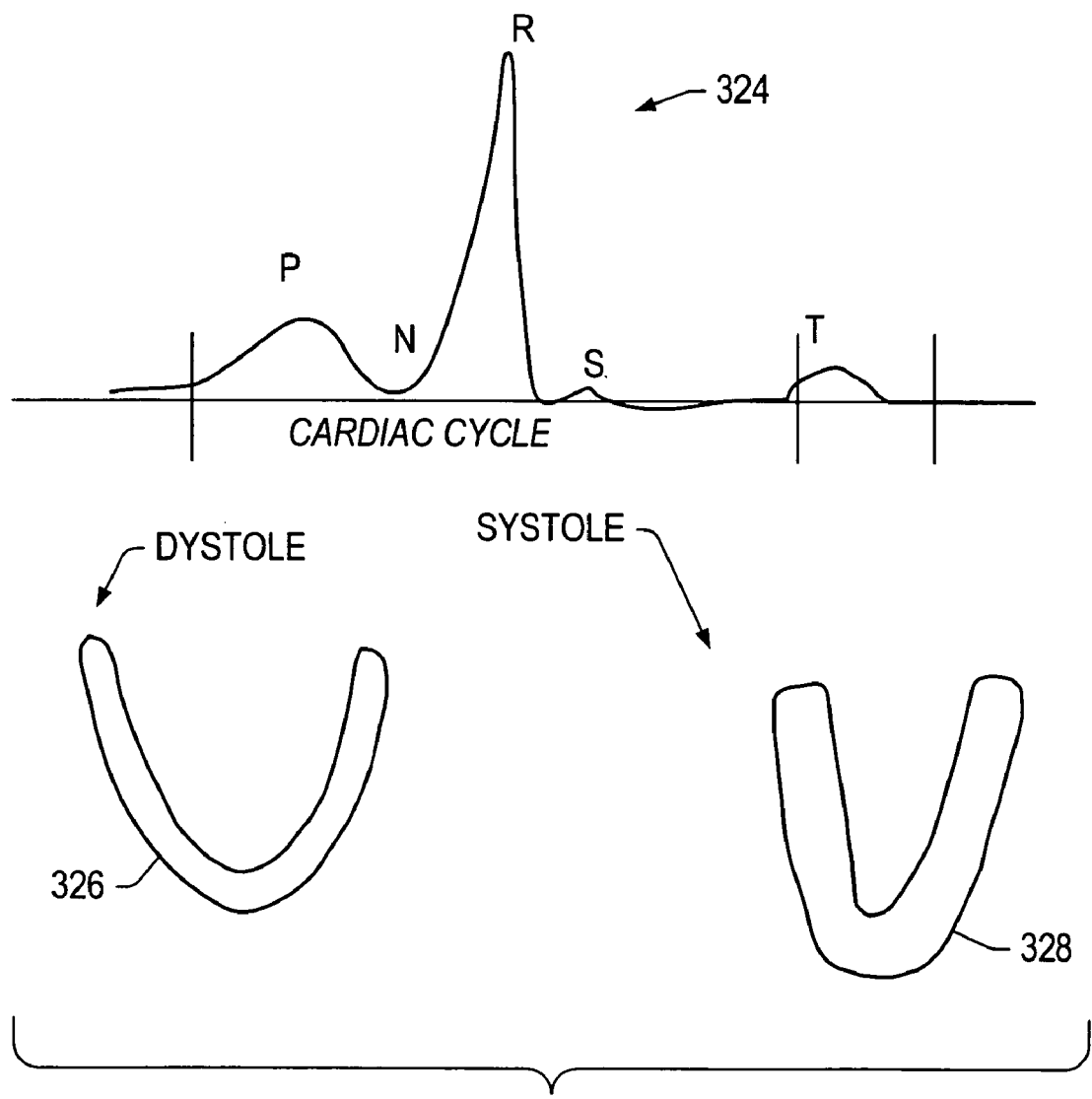
FIG. 45 depicts an electrocardiogram and images of a ventricle during various stages of a cardiac cycle.

One method of identifying akinetic tissue is to use images from an MRI or echocardiography. These images may include a combination of sections of the heart imaged during one cardiac cycle, so that each section contains a complete cycle. These sections may be combined to create one composite image. FIG. 45 depicts electrocardiogram 324 displaying a full cardiac cycle from diastole 326 to systole 328 of a heart as an example of a measured cardiac cycle. The images at the end of systole and the end of diastole are identified, shown in FIG. 46. These images are overlaid by aligning markers that do not move (e.g., the aortic valve annulus) and a grid pattern is superimposed on these images, as shown in FIG. 47. Each intersection of the grid that intersects the epicardium and endocardium may be identified.

Figure 46:
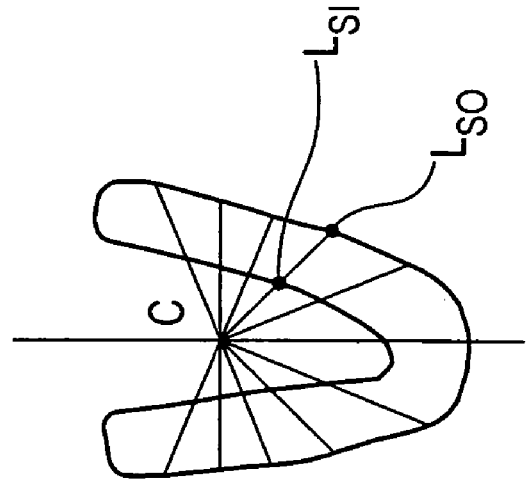
FIG. 46 depicts an embodiment of a comparison of systole and diastole images of a ventricle to show effect of wall thickening.
Figure 46:
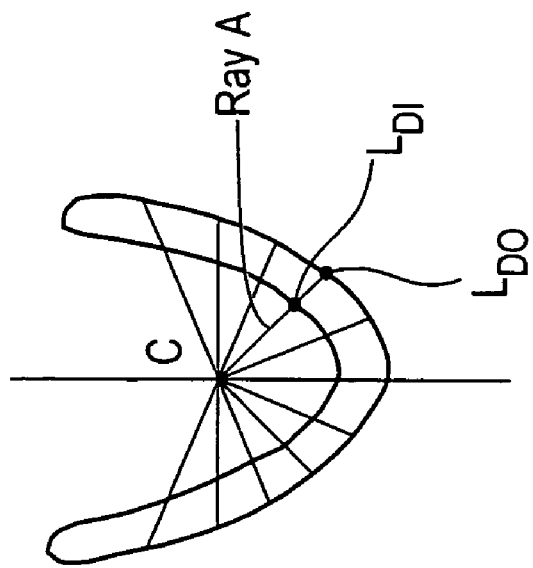

In an embodiment, a geometric center of the heart is calculated and imaginary lines (rays) 330 are drawn from the geometric center (shown in FIG. 47). Two points on each ray may be recorded. A point is defined as a point of intersection of a ray to the endocardium and/or epicardial boundary. For instance, $X_A$ 332 and $Y_A$ 334 are points on the border zone in this plane. The distance between these two points gives the wall thickness (d). Wall thickness is calculated on the diastole image $d_d$ and on the systole image $d_s$. As shown in FIG. 46, the wall thickness at the diastole is $d_d = CL_{DO} - CL_{DI}$. Similarly, the wall thickness at the systole is $d_s = CL_{SO} - CL_{SI}$. Typically, $d_s > d_d$ when the heart functions normally, because the myocardial wall thickens during systole to create pumping action. If a section of the heart muscle is diseased then $d_s \approx d_d$, which means that a portion of the wall is not thickening. The portion not thickening is referred to as akinetic tissue, which could be either dead or non-contributing tissue. All the rays that correspond to akinetic tissue are identified (all rays where $d_s \approx d_d$) by analysis of the collected images. A boundary layer of the akinetic area is established by comparing each of the akinetic rays to its neighboring rays. It is generally accepted that if a wall thickness of a portion of a heart is less than 5 mm, then that portion is effectively akinetic. For any given akinetic ray, if at least one of its neighboring rays is kinetic ($d_s > d_d$) then that akinetic ray is the boundary layer ray. Once all rays on the boundary layer are identified, the point of intersection of the boundary layer rays on the endocardial boundary defines the border zone between the viable and akinetic tissue. In an embodiment, a computer system may create an image of an assessed wall thickness. An image may include progressive coloring to differentiate an extent of wall thinning and/or dead tissue (e.g., when the wall thickness is less than 5 mm).

In an embodiment, a degree of transmurality of a scar (e.g., diseased or nonviable tissue) may be assessed using a computerized method based on, for example, enhanced MRI imaging. Transmurality of a scar in a portion of a heart is generally defined as the extent or depth of scar tissue through a wall of a heart. Generally, scar tissue may be found starting on the interior (i.e., endocardial) wall of a chamber of the heart. As scar tissue worsens, the scar tissue generally spreads outward to an exterior wall of the heart. Scar tissue typically begins forming on the interior of the heart because vessels deliver blood to the exterior tissue first and the interior tissue last. Therefore, if there is an interruption of blood flow, interior cardiac tissue may be the first to suffer stress and/or disease. Using imaging (e.g., enhanced MRI imaging) viable tissue may be assessed using a computer system to assess a contrast between different portions of an image of a heart. In an embodiment, an image may be created of an assessed transmurality. Progressive coloring may be used to display an extent of transmurality. In some embodiments, a length of a scar may be measured. The scar may be measured as a percentage of the perimeter of the endocardial boundary. The scar may be measured automatically by a computer system. A result of the measurement of the scar may be used as one factor in assessing a condition of a left ventricle. In an embodiment, a length of a scar may be measured by taking a predetermined slice from a model of a left ventricle (e.g., a slice from a four chamber view of the heart) and measuring a perimeter length, P, of the ventricle and a length of a scar, Q. The scar may be assessed by dividing Q by P. If Q/P is, for example, greater than about 50%, then the left ventricle is potentially suitable for reconstruction. FIG. 48 depicts an embodiment of a pictorial representation of a cross-sectional view of ventricle 210 and a method of measuring a scar as a percentage of an endocardial boundary. In an embodiment, a length of a scar may be measured by a computer system without significant user input beyond the provided images of the subject's heart.

In an embodiment, similar methodology described above for creating a three-dimensional image and identifying a border of a portion of a heart may be employed to assess the volume of a portion of a heart. Once a three-dimensional image has been created, standard methodologies may be employed to assess the volume of a portion of a heart in the three-dimensional image. Specific examples of volumes that may be assessed include, but are not limited to, the end diastolic volume and the end systolic volume of a heart. A computer system may assess a volume of a portion of a heart in an automated fashion. Potential advantages over current technology may include increasing the accuracy of an assessed value for a volume.

In certain embodiments, viable and nonviable tissue may be assessed by creating multi-dimensional images from one image or a plurality of images. Images from enhanced MRI may be used. Images may be enhanced by using dyes ingested by the patient. These dyes dramatically increase the contrast of two-dimensional images collected by an MRI. Many dyes specifically work to increase the contrast in images between viable and nonviable tissue. The contrast increase is due at least in part to the fact that blood does not adequately circulate through nonviable tissue, which inhibits permeation of any dye into nonviable tissue. An example of an enhanced MRI imagining technique is gadolinium enhanced MRI. An increased contrast may allow a computer system to assess viable and nonviable tissue by analyzing the dye enhanced areas of the MRI images.

In an embodiment, a computer system may be provided at least two images. At least one image may include an unenhanced low contrast MRI image. At least one additional image may include a contrast-enhanced image (e.g., gadolinium contrast enhanced). A computer system may employ contrast-enhanced images to assist in assigning features of a normal or low contrast MRI image. Commonly identified features of the enhanced and unenhanced images may be used as reference points by the computer system to align the two images. Once the two images are aligned, the enhanced image may be used to identify borders and features of the unenhanced image.

Typically, enhanced images (e.g., MRI) are procured only for one phase of a cardiac cycle (systole or diastole). Enhanced images may, however, be used to demonstrate strain on a ventricular wall. In an embodiment, enhanced images may be provided of a heart in both the systole and diastole. Capturing enhanced images in both phases may demonstrate which muscle fibers are stretching. Enhanced images may demonstrate how much certain areas stretch relative to other areas of the heart. In some embodiments, Gadolinium may be used as an image enhancing dye to provide enhanced images. In certain embodiments, wall thicknesses may be assessed during systole and diastole using the enhanced images.

In an embodiment, a computer system may take portions of provided images and divide the portions into sections. Sections may be regular or irregular. Divided sections may not necessarily be divided evenly with regard to size and/or shape. Sections may be two-dimensional or three-dimensional. A computerized method may assign a value to a section based upon a feature of that section. In an embodiment, a feature may include a color of that section. It should be noted that the term "color" may include grayscale images. A feature may include a color due to the use of enhanced MRI imaging. A color value may be used to determine a viability of that section or an adjoining section. A computer system may determine the viability of the portion of a heart by determining which sections, within the analyzed portion, are assigned a certain color value. A color value used as a standard for assessing the viability of tissue in a section may be provided by a user and/or be preprogrammed in the computer system.

Figure 50:
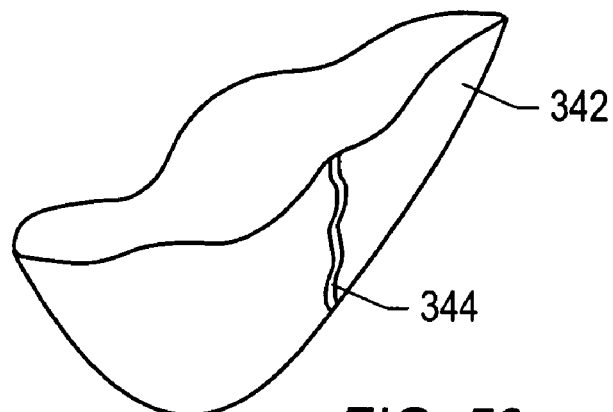
FIG. 50 depicts an embodiment of a pre-cut shape to allow a user to identify, on a heart, a diseased tissue.

In an embodiment, once a location of a diseased section is identified with respect to other cardiac structures, a 3D CAD file (DXF or STL files) may be generated that shows the location of the border area with respect to a known landmark on the heart. Referring to FIG. 44, a template may be created that identifies the location of the akinetic tissue. FIG. 49 depicts an embodiment of mesh structure template 336 that may be generated from a 3D CAD file with border areas 338, 340 indicated on the mesh. Mesh structure 336 may be used to assist a user in locating a diseased portion of an actual heart during a surgical procedure. FIG. 50 depicts an embodiment of an alternative template 342. A pre-cut shape is formed based on the modeling program to assist a user to identify, on a heart, a diseased tissue 344 during an actual surgical procedure.

In an embodiment, an at least three-dimensional image may be created demonstrating a diseased section. A diseased section may include "progressive coloring." Progressive coloring-may assist a user in visualizing and understanding an extent of the diseased section. Progressive coloring may in general be defined as displaying an extent to which a condition exists by relating a relative extent of the condition to a relative gradient in color. For example, the greater an irregularity of a portion of heart tissue, the greater the contrast in a color of the portion is relative to another portion of heart tissue in an image. Color may include grayscale as well. A template may be created that matches the diseased area. The template may include anatomical landmarks from the heart such as left anterior descending artery or the atrial ventricular groove. The anatomical landmarks may help to align the template to the diseased area. In certain embodiments, the template may be in a form of a balloon that is patient specific with the same shape and/or size as the interior of the ventricle. The template may include a border zone marked on the template. The template may be like a glove that fits on the outside of the heart with border zone and landmark points marked on it. Such tools may be very helpful in order to execute an SVR procedure with greater precision.

In an embodiment, a method to assess the diseased area of the ventricle includes measuring the motion of the endocardium towards a centerline of the ventricle. This "centerline method" determines the region of no motion by evaluation of how motion at various points of the ventricle differs from the standard motion. In the centerline method, any tissue that moves less than 2 standard deviations from a typical movement level of a normal heart may be considered diseased. This algorithm could be applied in the above-mentioned model to identify the border zone. The model may generate an image using different color gradients (e.g., progressive coloring) to depict the range of lack of motion from the standard. Color grading may give the user a precise location for tissue to exclude and allow the user to not exclude any viable tissue. Another advantage of progressive coloring may be that it allows a user to make a more informed decision when it comes to, for example, excluding nonviable tissue. In some cases, a user may choose not to exclude some tissue that is potentially nonviable in order to use that tissue to assist in a reconstruction of a left ventricle. A template showing the status of the myocardium stated above may be provided to the user to use as an aid in excluding the tissue. The gradient image may be used for both idiopathic and ischemic cardiomyopathy patient assessment. In addition, percent asynergy may be assessed by dividing a number of diseased sections, as assessed by, for example, the centerline method, by a total number of sections and multiplying by one hundred.

Analyzing ventricular performance based on wall motion is a common practice in cardiology. Traditionally, analysis is done on two-dimensional images such as angiographic or echo images. An analysis technique typically used by a clinician is the centerline method. The centerline method has been a popular tool for cardiologists all over the world for a long period of time. Descriptions of the centerline method are presented by F. H. Sheehan et. al., in "Advantages and applications of the centreline method for characterizing regional ventricular function", Circulation 1986; 74, No. 2, pp. 293-305; and by M. Imamaki et. al., in "Prediction of improvement in regional left ventricular function after coronary artery bypass grafting", J. Cardiovascular Surg. 2002; 43: pp. 603-7, each of which is incorporated by reference as if fully set forth herein.

Centerline methods may use projections like RAO view (Right Anterior Oblique). Centerline methods may be used to calculate the kinetic properties of the anterior wall, inferior wall, and/or apical region of the left ventricle and compare the kinetic properties to a predetermined normal range. The centerline method may, however, be applied to any view, or to other forms of images such as MRI images. Descriptions of the centerline method being applied to MRI images are presented by E. R. Holman et. al., in "Detection and Quantification of Dysfunctional Myocardium by Magnetic Resonance Imaging Circulation" 1997; 95; pp. 924-931; and F. P. van Rugge et. al., in "Magnetic Resonance Imaging during dobutamine Stress for detection and localization of coronary artery disease" Circulation 1994; 90, No 1, pp. 127-138, each of which is incorporated by reference as if fully set forth herein.

Examples of commercial software packages that perform wall motion analysis based on the centerline method include those available from Sanders Data Systems, Medis, and GE Medical Systems.

In some embodiments, the centerline method may be employed along various planes to identify akinetic tissue segments. Akinetic areas may be represented on multi-dimensional ventricular models. The development of a three-dimensional analysis system requires that traditional two-dimensional analysis methods be extended to function equally as successfully in three or more dimensions.

Figure 51:
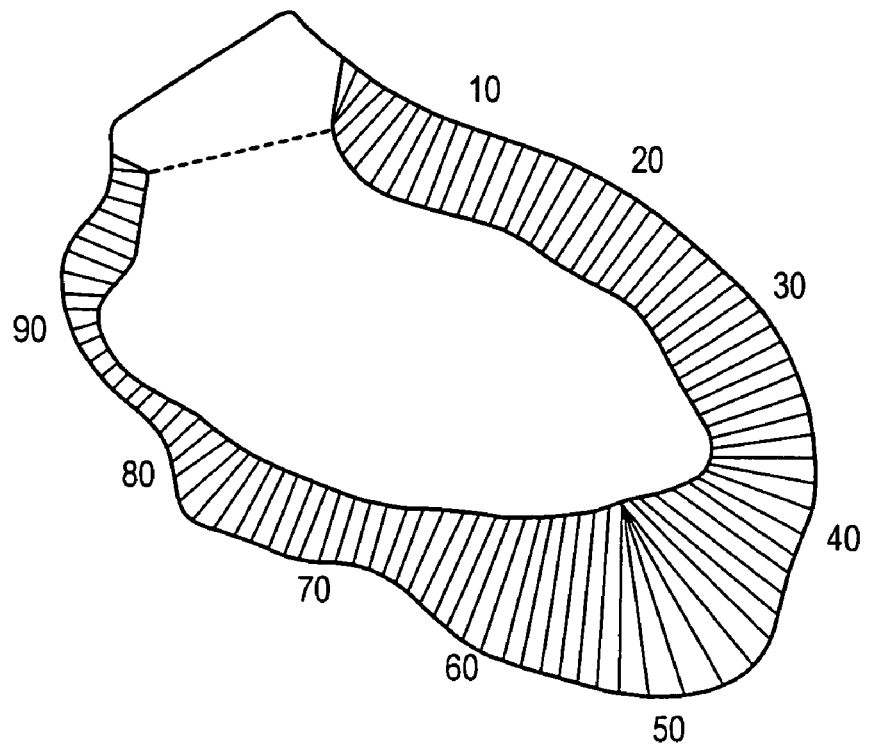
FIG. 51 depicts an embodiment of an example of an RAO view tracing the endocardial boundary in both the diastolic and systolic images with 90 subdivisions of the distances allowing regional quantification of wall motion.

The centerline method may utilize a two-dimensional view of the heart (e.g., the right anterior oblique or RAO view). The RAO view represents a two-dimensional slice through the ventricle in which the anterior and inferior walls are visualized. By tracing the endocardial boundary in both the diastolic and systolic images and then superimposing the two, it is possible to measure the distance the wall has moved from the ventricle's maximum size to the ventricle's minimum size. FIG. 51 depicts an embodiment of an example of an RAO view tracing the endocardial boundary in both the diastolic and systolic images with 90 subdivisions of the distances allowing regional quantification of wall motion. The distances may be divided into any number of subdivisions, and are not limited to 90 subdivisions; however, 90 subdivisions is currently a standard number of subdivisions used.

Figure 52:
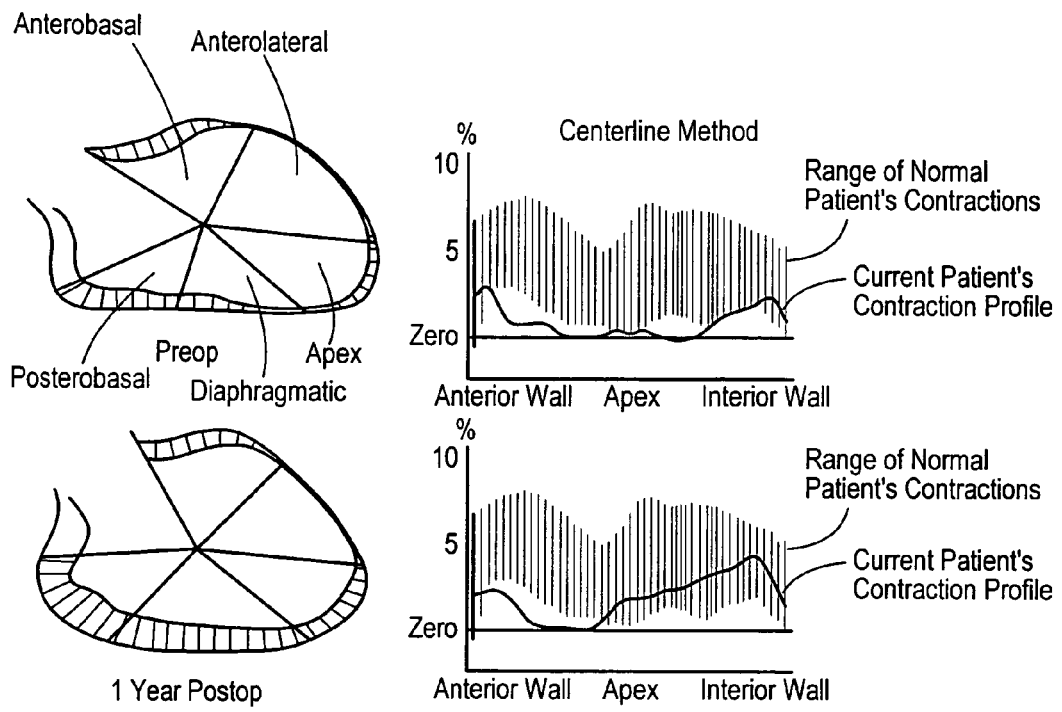
FIG. 52 depicts an embodiment of an example of a pre and postoperative case with two graphs showing patient wall motion plotted against a normal contraction distribution.

After producing and measuring the individual distance 'chords', a graph may be created highlighting the regional motion analysis of the anterior wall, inferior wall, and/or apex of the left ventricle. FIG. 52 depicts an embodiment of an example of a pre- and post-operative case with two graphs showing patient wall motion plotted against a normal contraction distribution. Normal contraction is established based on "chord" distances in normal hearts (to be more specific normal contraction is mean "chord" distance of the population of normal hearts +/−2 standard deviations). FIG. 52 shows the RAO view segmented into five distinct regions. These regions are as follows (from clockwise):

1. Anterobasal;
2. Anterolateral;
3. Apex;
4. Diaphragmatic; and
5. Posterobasal.

Because the RAO view is segmented consecutively the graphs on the right of FIG. 52 can be read left to right as points 1 through 5. The length of the chords may determine if the wall is hyper-kinetic, normal, akinetic, andlor diskinetic. A tissue segment may be considered hyper-kinetic if the corresponding chord length exceeds mean +2 standard deviations of normal heart data for that chord. A tissue segment may be considered akinetic if the corresponding chord length exceeds mean −2 standard deviations of normal heart data for that chord. A tissue segment may be considered normal if the corresponding chord length fall within mean +/−2 standard deviations of normal heart data for that chord. A tissue segment may be considered diskinetic if the corresponding chord length is negative. The numbers given for defining the different types of tissue within the context of the centerline method are merely given as guidelines and may be adjusted (e.g., adjusted as new data becomes available).

In some embodiments, the centerline method may be extended from two-dimensional images/models to three-dimensional images/models. A three-dimensional extension of the centerline method may be based on two point sets that represent the endocardial wall in end-systolic and end-diastolic state. This may be accomplished by the creation of an equally distributed three-dimensional model. It is similar to dividing the RAO view into 90 segments.

Figure 53:
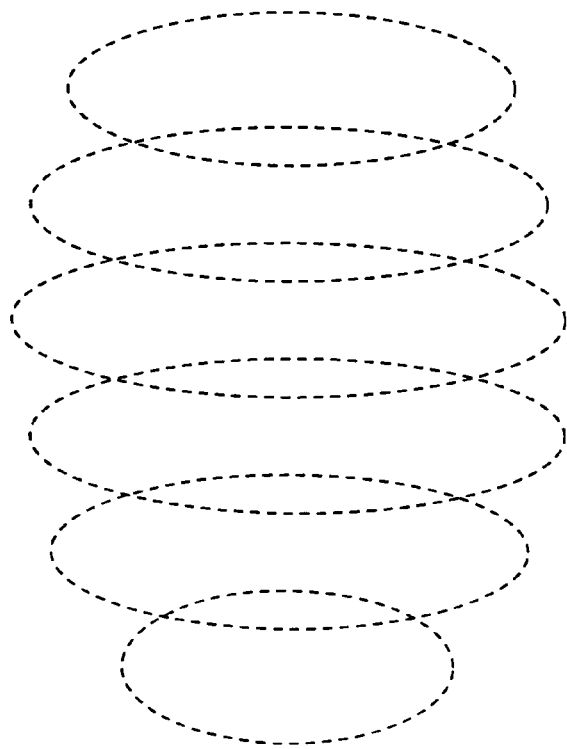
FIG. 53 depicts an embodiment of an example of a wire frame model of a left ventricle constructed from point sets representing the endocardial contours.

In some embodiments, point sets representing the endocardial contours may be used as the vertices necessary to reconstruct a wire frame model of the left ventricle. FIG. 53 depicts an embodiment of an example of a wire frame model of a left ventricle constructed from point sets representing the endocardial contours.

Figure 54:
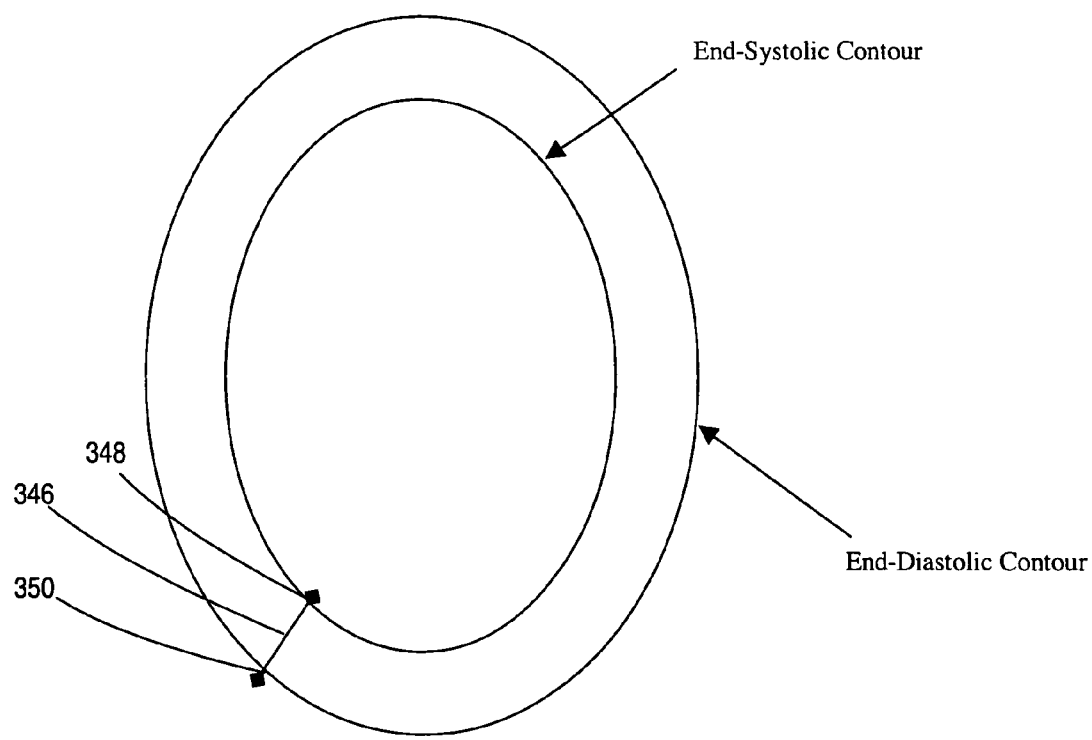
FIG. 54 depicts an embodiment of an example of a cross section through an ellipsoid highlighting the normal matched points on the surface.

The wire frame model may be triangulated. Once the model has been triangulated, each individual triangular facet may have a normal associated with it. These normals may be used to match triangles on the end-systolic model with those on the end-diastolic model. FIG. 54 depicts an embodiment of an example of a cross section through an ellipsoid highlighting the normal matched points on the surface. FIG. 54 depicts normal 346 matched points 348 and 350 on end-systolic and end-diastolic ellipsoid approximation of the left ventricle respectively.

Once every triangular facet on the end-systolic and end-diastolic model has been 'paired' according to the end-systolic normals, the chord lengths may be measured (the Euclidian distance) between each triangle facet pair. This chord length may be a three-dimensional line that is analogous to the two-dimensional chords in the traditional centerline method.

Upon assessment of the chord lengths, the wall motion for each triangular facet of the left ventricular three-dimensional model may be calculated. The kinetic properties of the ventricle may be quantified according to the chord lengths. The same criteria may be applied in identifying hyper-kinetic, akinetic, normal, and/or diskinetic segments.

A bullseye plot is currently a popular way of depicting 3D information of the ventricle in 2D projection. This is common practice in cardiology in general and nuclear Cardiology in particular. Many commercial SPECT analysis software (e.g., QGS (from Cedar-Sinai Software)) includes bullseye plots as a standard feature.

Figure 55:
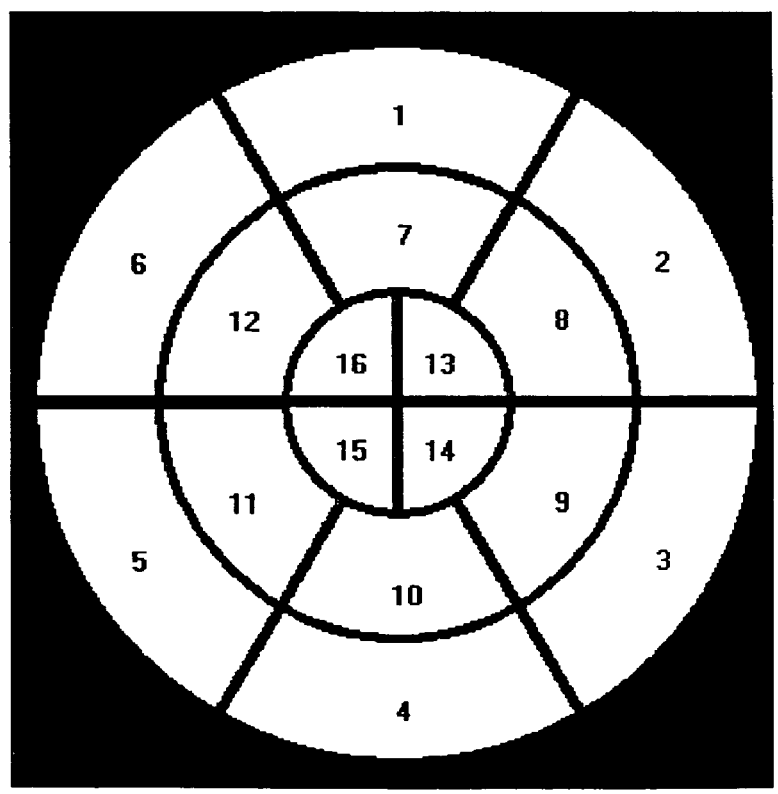
FIG. 55 depicts an embodiment of an example of bullseye plot of ventricular regions.

FIG. 55 depicts an embodiment of an example of a bullseye plot of ventricular regions. A typical bullseye model is displayed in FIG. 55 with each region described. The bullseye plot is a two-dimensional representation of the left ventricle with the outside being the basal region and the center being the apex. The regions on the bullseye are as follows:
1. Basal Anterior Septal Wall;
2. Basal Anterior Wall;
3. Basal Lateral Wall;
4. Basal Posterior Wall;
5. Basal Inferior Wall;
6. Basal Inferior Septal Wall;
7. Mid Anterior Septal Wall;
8. Mid Anterior Wall;
9. Mid Lateral Wall;
10. Mid Posterior Wall;
11. Mid Inferior Wall;
12. Mid Inferior Septal Wall;
13. Apical Anterior Wall;
14. Apical Lateral Wall;
15. Apical Posterior Wall; and
16. Apical Septal Wall Each of the triangles on the ventricular surface may fall into one of these anatomical regions based on the location of the triangle. The triangles may be color coded and presented on the bullseye plot based on which sections are hyper kinetic, normal, and/or akinetic.

Figure 57:
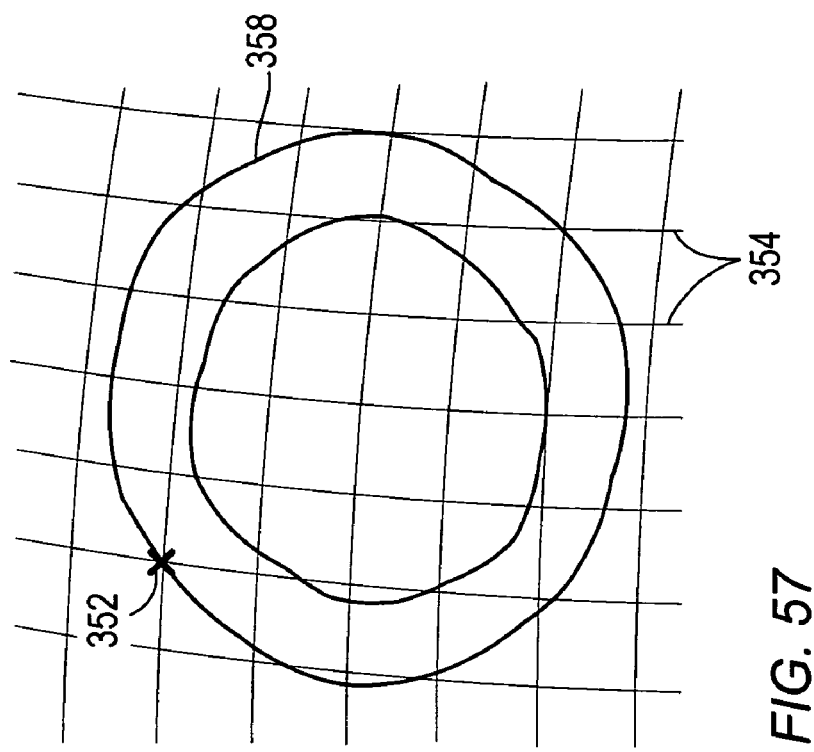
FIG. 57 depicts an embodiment of an image of a portion of a heart in a substantially contracted condition.
Figure 56:
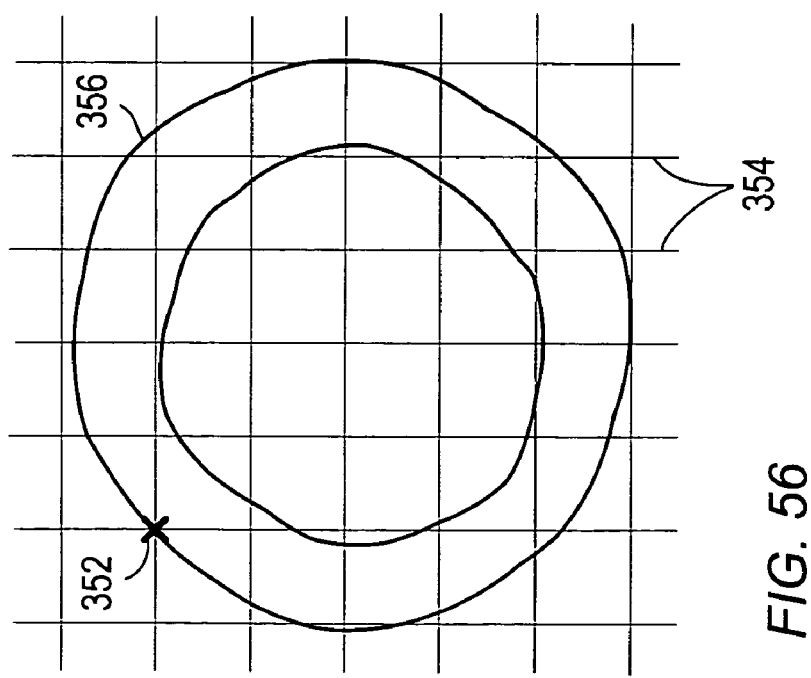
FIG. 56 depicts an embodiment of an image of a portion of a heart in a substantially expanded condition.

In some embodiments, a method to assess a viability of a portion of a heart may employ "tagging" portions of an image of a heart. Tagging may include assigning points of reference to an image of a heart. In an embodiment, point of reference 352 may be part of a larger grid 354 overlayed on image 356 (depicted in FIGS. 56 and 57). Image 356 may be provided to a computer system alone or in combination with a plurality of images. The computer system may assign points of reference 352 and/or grid 354 to a created image 356 of a heart. FIG. 56 depicts image 356 of a portion of a heart in a substantially expanded condition with grid 354 and reference point 352. FIG. 57 depicts image 358 of an equivalent portion of the heart in a substantially contracted condition with grid 354 and reference point 352. By following or tracking the movement of reference point 352 and/or the distortion of grid 354, a user may assess the activity of (e.g., viable) a particular section of a portion of a heart. The computer system may track reference points 352 and automatically calculate the movement distance of the points. The computer system may assess the viability of human heart tissue using movement data. In an embodiment, a computer system may create a multi-dimensional image of the assessed motion or viability of the heart. The model may include progressive coloring to display the extent of damage of the heart.

In an embodiment, a method to assess a shape of a portion of a heart may be employed. Shape analysis is an important feature of a heart for assessing a condition of a heart before and/or after a cardiac intervention. Shape of a heart and/or portion of a heart may be assessed, in one embodiment, by employing a similar method as described for assessing a motion of a portion of a heart. For example, a computer-automated version of the "centerline method" may be used to assess a shape of a heart. An image of a heart may be created by a computer system from at least one of a plurality of images. A portion of the image may be divided into sections. Curvature of one or more sections may be assessed by the computer system. A computer system may sum the curvatures of all or a portion of the sections to assess a shape of a portion of a heart. In an embodiment, an image of the assessed shape may be created using a computer system. The image may be at least two-dimensional and may be three or four-dimensional.

In an embodiment, a method to assess a shape of a portion of a heart may be employed. A shape of a heart may be assessed by determining the "effective height" of the heart. Effective height may be the ventricular volume divided by the ventricular surface area. Effective height may be calculated from a model of a ventricle. For example, for a sphere, the effective height ratio would be at its lowest, while becoming higher for more elliptical shapes. A measurement of effective height may give an idea of a dilation of a heart (e.g., the closer to a sphere shape the heart is, the more dilated the heart typically is). Effective height may give a user a way of measuring how far a patient's heart has deviated from a "normal" shape. Typically, the more distorted a heart becomes, the closer to the shape of a sphere the heart shape approaches.

Figure 58:
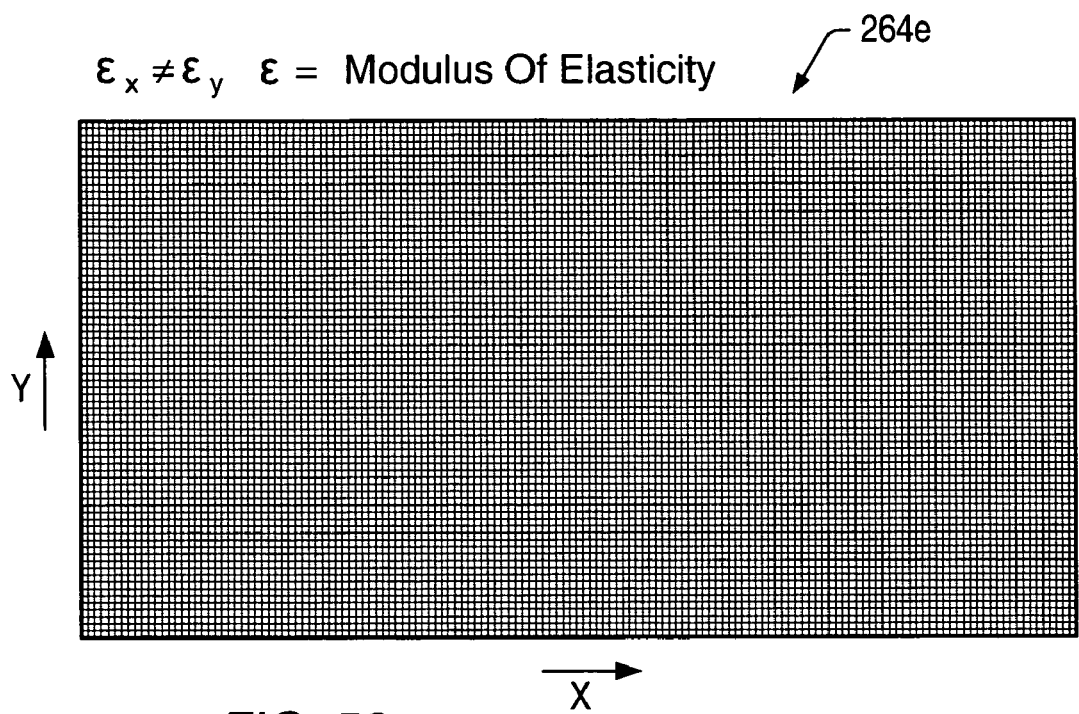
FIG. 58 depicts an embodiment of a patch with fibers that have strength in one axis different from a strength in another axis.

In an embodiment, when tissue is excluded as described herein, there may be a hole left in the ventricle that a surgeon will fill. One device that might fill or cover the hole is a patch that could aid in the contraction of the left ventricle. One form of a patch may be made of a fabric that is pretensioned and stretched to fill a hole left in a ventricle. The pretensioning places stress on the fibers, that assist the ventricle in contraction when going back to the relaxed state during systole. In some embodiments, short axis fibers are of a different strength than long axis fibers. Different strength fibers in the short and long axes may provide greater contraction along the short axis, as shown in FIG. 58. FIG. 58 depicts an embodiment of a patch 264e with fibers that have strength in one axis different from a strength in another axis. The patch could have pretensioned fibers only in the center of the patch, decreasing the tension exerted by the patch on the ventricle walls, while still providing some assistance to the ventricle during contraction.

Figure 59:
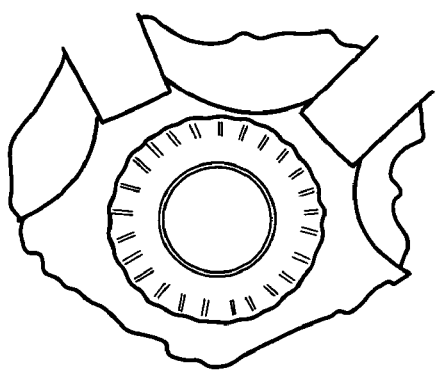
FIG. 59 depicts an embodiment of completed bypass graft.

In an embodiment, an apparatus and/or method described herein may be used to plan for bypass or stent interventions. Bypass or stent interventions may be planned by showing the location and condition of the arterial system of the heart. Imaging of the arterial system with identification of lesions and blockage has been performed using ventriculograms. This process injects a dye into the aortic root, which supplies the cardiac arterial system with blood. The dye flows through the arterial system with the blood and may be imaged with X-rays to identify where the constricted points of the arterial vessels are located. The arterial system may be mapped using the flow of dye. A finite element model may be applied to the system to determine the width of the vessels, location of constrictions, etc. The model may predict how much blood is flowing to each portion of the heart. This prediction may be correlated to displays of viable tissue so that if the patient has had a myocardial infarction and has dead tissue, the user does not use the best graftable conduits (FIG. 59) to graft to vessels feeding these areas or place stents on these vessels. In some embodiments, the user may choose to not graft or stent at all in these locations. A model may give the user the opportunity to place different grafts or stents on different vessels to analyze the perfusion effect on the heart for different combinations. The grafts or stent models may come from a database of surgical equipment and devices. The model may be run to show a user the effect that grafts or stents may likely have on an entire cardiac and circulatory system so that the best combination of locations for that particular patient may be selected.

In some embodiments, a model a subject's heart may be used to assess "underperfused" areas of cardiac tissue (e.g., ischemic tissue) that has not scarred yet. A model may be used to more effectively display underperfused tissue. Assessing underperfused areas of the subject's heart may better allow the user to more effectively determine ways of preventing further damage.

In an embodiment, an apparatus and method may also be used to show the effects that interventions performed on the left ventricle outflow tract and aortic valve (i.e., flow across the aorta (FAC)) may have on other elements or the entire heart. The outflow tract changes position as people age and an acute angle in the left ventricle outflow tract may contribute to poor performance of the ventricle and/or the aortic valve. The model may show the positioning of the left ventricle outflow tract and may show the user turbulence or restrictions in blood flow through this area. One model for analysis of flow dynamics is available from CDFRC (Huntsville, Ala.) and published by Makhijani et al. "Three-dimensional coupled fluid—Structure simulation of pericardial bioprosthetic aortic valve function", ASAIO Journal 1997; 43:M387-M392, which is incorporated herein by reference. If desired, a user may virtually manipulate the left ventricle outflow tract into different positions and run one or more models to see which position of the tract provides the best flow dynamics. The system may tell the user to adjust the positioning of the left ventricle outflow tract, if needed, and may show the effects that a new position will have on the performance of the heart.

Figure 60:
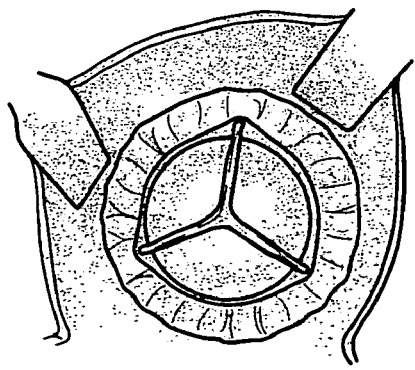
FIG. 60 depicts an embodiment of replacing an aortic valve.

In an embodiment, at least one or a plurality of images may be provided to a computer system. A velocity of a blood flow may be provided to the computer system. A time over which a valve (e.g., the aortic valve) may be open for one cycle may be provided to a computer system. A computer system may then assess the area of an open aortic valve. A computer system may use the assessed area, blood flow velocity, and time for which the valve was open to assess blood flow across a valve. Poor performance of the aortic valve may limit the amount of blood that the ventricle may eject. The model may display the aortic valve and allow a user to virtually manipulate the valve and assess if the manipulations have increased the performance of the valve and/or increased the performance of the cardiac system as a whole. A user may take the desired results and perform those manipulations on the actual valve. FIG. 60 depicts a representation of an actual replacement of an aortic valve.

In an embodiment, a method and apparatus may be used to simulate the effects of drugs on the heart and its components. A database of drugs and their effects may be developed and the user may interact with the model by selecting a type of drug and dosage amount. A model may give the user the results of the treatment (e.g., whether the drug has resulted in a change in the geometry of the heart and its components and/or if the performance of the heart has improved). For example, the model may simulate the effects of vasodilators that diminish the afterload of the heart. In some embodiments, the effect of norepinephrine, which increases the contractility of the heart, may be assessed using the model. In an embodiment, a user may adjust the parameters of a particular drug already stored in the database. For example, a user may choose to adjust the percent of a particular chemical making up a particular chemical composition. In certain embodiments, it may be possible for a user to input parameters into a database for a new pharmaceutical composition. A user may compare known data about the new composition to data for compositions currently in the database, allowing the user to enter reasonably accurate parameters for a pharmaceutical composition not in the database.

In an embodiment, a method and apparatus may be used to simulate the placement of mechanical devices in or on the heart to determine the benefits of the devices. The physical and functional characteristics of these devices may be determined through testing and reduced to a finite element model. These finite element models may be placed in a database. The user may interact with the model by choosing the device by its common name or product name (e.g., Myosplint or Corecap). The user may direct placement of a device by methods described above (e.g., methods for specifying location, attachment means etc.). Left ventricular assist devices may also be added to the database. All these mechanical devices may be simulated to show their effects on the whole heart and its components. These effects may be compared to other less invasive treatments to determine if the increased invasiveness and cost of these devices is warranted by any increase in the heart's performance.

In an embodiment, a method and apparatus may be used to assess results or effects other than structural effects resulting from proposed procedures and/or treatments. One example may be assessing effects of procedures and/or treatments on an electrical system of a heart. The method may assess an electrical effect, for example, of reconstructing a left ventricle of a human heart. For example, the method may determine if arrhythmia results from a reconstruction of a particular patient's heart. In an embodiment, an electrical result from a modification of a feature of a heart may be assessed by comparing the modification to a database containing similar procedures. A computer system may create an image of assessed electrical effects from a proposed procedure.

In some embodiments, a method may quantify mechanical dysynchrony of the left ventricle. In order to quantify such a parameter, the method may establish a system of comparison to a normal range of values. By using such a comparison coupled with deviation from a set range, the method may produce a dysynchrony index for any left ventricle.

Figure 61:
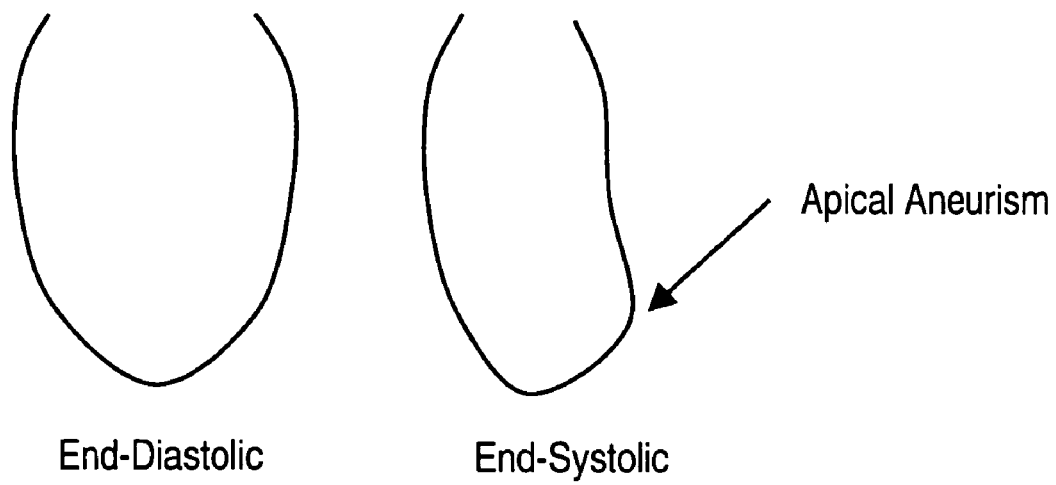
FIG. 61 depicts an embodiment of an example of an aneurism of the apex seen only in end-systolic phases.

Dysynchrony is an abnormality in the temporal behaviour of a system. Regional mechanical dysynchrony of the left-ventricle involves a specific portion of the myocardium that is not adhering to the correct progression of contraction during the cardiac cycle. Such symptoms may be observed, for example, in cases of hypertrophy, dilated-cardiomyopathy, bundle branch block (BBB), and aneurisms. In the case of ventricles with aneurismal characteristics, a systolic bulge exemplifies mechanical dysynchrony where the aneurismal tissue is not contracting with the rest of the ventricle. FIG. 61 depicts an embodiment of an example of an aneurism of the apex seen only in end-systolic phases. Dysynchrony, however, may be less obvious than in the aforementioned example. Therefore, it may be necessary to provide a means of analyzing the temporal characteristics of the left ventricle in greater detail.

The left ventricle is commonly split into 16 regions for analytical purposes; these regions are often displayed flattened into a two-dimensional circular graph called a bullseye plot. A typical bullseye model is displayed in FIG. 55. FIG. 55 shows a bullseye plot split into these 16 regions with an explanation in the accompanying key described herein.

The regions shown in the bullseye plot roughly correspond to anatomical regions of the left ventricle. Because the bullseye plot is uniformly spaced and in reality the left-ventricle is non-uniform, the regions are only approximations. When looking at the left-ventricle with the purpose of measuring dysynchrony, the bullseye plot is a good starting point as the plot creates a standard division of the ventricle as a means of comparing measured regional parameters. In order to measure dysynchrony and compare it to a normal range of ventricular values, it may be necessary to split the ventricle into a multitude of regions, evenly spaced and created in the same manner for each ventricle. In some embodiments, a uniform creation of a mesh of points across any ventricular surface may provide a means for comparison of small enough elements of the ventricle to obtain an accurate representation of dysynchronous zones.

In order to arrive at the successful creation of a left-ventricular dysynchrony index, the behavior of normal left ventricles may be examined as a means for comparison.

In a healthy left ventricle, the epicardial boundary may be observed to have little transverse motion associated with it while the endocardial boundary changes from an ellipsoid shape in end-diastole to almost a conical shape in end-systole. Motion analysis of the heart may look at the change in position of the endocardial boundary from end-diastole to end systole in reference to a fixed line or point in space. This method of analysis is more commonly called the centerline method. The centerline method is generally successful in regionally quantifying the endocardial motion across the cardiac cycle, but may not be appropriate for dysynchrony analysis as it does not take the left ventricular wall into consideration.

Temporal analysis of left-ventricular wall thickness is a good basis for creating a dysynchrony index as the epicardial and endocardial boundaries are both incorporated. In the healthy ventricle the epicardial boundary has little motion associated with it so thickness measurements tend to be similar to motion analysis. When the abnormal ventricle is analyzed, it may be possible to observe areas that do not conform to normal temporal behavior by observing the change of thickness over time. Myocardium that is still thin as the cardiac cycle approaches end-systole may indicate regions of poor contraction. In such areas of poor contraction, it may be possible for the endocardial boundary to move uniformly with the epicardial boundary and maintain constant wall thickness across the cardiac cycle. This is a primary reason for analyzing wall thickness when determining dysynchrony. The left-ventricular endocardial boundary may move but have no associated wall thickening in the same region. However, the dysynchrony index can be based either on left ventricle wall motion and/or left ventricle wall thickening. In either case a normal range may first be established (e.g., normal +/−2 standard deviations)

In certain embodiments, left ventricular point meshes may be created uniformly (i.e., wire frame creation with equal number of triangles in the wireframe). Once the triangulated ventricle is created in various phases, the beginning of contraction for a given triangle in the ventricle may be noted as a percentage of a cardiac cycle (e.g., time in milliseconds when contraction begins/total cardiac cycle). Similar calculations may be made for all the triangles of the ventricle. These calculations may be repeated on "n" number of normal (e.g., healthy hearts, where n=statistically significant number based on required accuracy). From the data obtained, a mean and standard deviation number may be calculated for each triangle. Thus a range may be established (mean +/−2 standard deviation) for each triangle.

It is to be noted that the normal range may be established either based on wall motion (in which case, when a triangle begins to move towards the centerline is noted) and/or based on wall thickness (in which case, when a wall thickness starts to increase is noted).

In some embodiments, as with many measured parameters, it may useful to have a single figure for comparison between left-ventricles. Ejection fraction, for example, is a simple number that allows immediate comparison of basic cardiac function. In creating a dysynchrony index, a percentage of abnormal values may be compared to the normal. In certain embodiments, for example:

A left-ventricular point mesh may consist of 500 points
90 points may be outside the normal range by ±2 standard deviations
The resultant dysynchrony index would be (90/500) 18%

Bio-ventricular pacing involves administering a timed electric pulse to a specific region of the left ventricle in order to maintain normal synchronous behavior. Currently lead placement is typically guesswork. Placement of pacing leads based on knowledge of the most dysynchronous regions of the left-ventricle may improve the success of bio-ventricular pacing therapy. A ventricle may be dysynchronous in multiple regions. Thus, it can be important when analyzing the ventricle to maintain the position of the most dysynchronous regions in order of magnitude.

With this method, the deviation of each dysynchronous triangle from the normal may be used to identify the most dysynchronous area, followed by the next most dysynchronous area, and so on. Identifying these areas may allow for the best lead placement location, followed by next best lead placement location, etc.

In some embodiments, a method may create a left-ventricular mechanical dysynchrony index. A database of normal patient data may be established that can be reconstructed in four dimensions and temporally analyze the wall thickness/wall motion at each mesh point. This data may represent the normal range of synchronous behavior of the left ventricle at any given point across the ventricular surface. Once this data has been collected, data from patients may be compared with dysynchronous ventricular behavior.

Dysynchronous ventricles in comparison to the normal range may be divided into subsets based on the dysynchrony index described herein. Further analysis of patients with poor dysynchrony indices may provide an insight into the most dysynchronous zones of the left-ventricle and may provide a more intelligent approach to bio-ventricular pacing lead placement.

In an embodiment, a method and apparatus may be used to assess results or effects other than structural effects resulting from proposed procedures and/or treatments. A model created of a heart may be used to assess where the last muscle contraction is occurring. A muscle may be contracting last because the particular muscle or portion of a muscle is receiving electrical signals later relative to other portions of the heart. Order of contractions of portions of a heart may be determined from a model of the heart. The order of contractions may be determined mechanically from the model of the heart. Contractions may be determined from wall thickness, assessed motion, etc. Currently, leads from a pacemaker are placed on the outer surface of the heart muscle wall to assist in mediating muscle contractions. With a more accurate determination of the order of muscle contractions by determining the order mechanically, leads from a pacemaker may be more accurately placed on specific portions of the heart. Leads may be positioned endoscopically, for example, through a vein to an inner portion of a heart. In some embodiments, multiple leads may be positioned adjacent areas that require electrical assistance in the heart. Multiple leads may be positioned throughout the heart and programmed with a distinctive activation pattern to compensate for patient specific multiple delayed contractions. In certain embodiments, a phase delay may be provided between multiple leads based on the timing between contractions of the portions of the heart at which the leads are located.

In an embodiment, mitral regurgitation may be assessed using an imaging method and/or system described herein. One image or a plurality of images may be provided to a computer system. A computer system may use at least some of the images to assess mitral regurgitation for a human heart. A system may use images to generate an end diastolic volume (EDV), an end systolic volume (ESV), and a FAC (i.e., flow across the aorta). A value for a mitral regurgitation may be assessed from this data using EQN. 1:

$$\text{Mitral Regurgitation} = (EDV - ESV) - FAC \tag{1}$$

Methods of assessing EDV, ESV, and/or FAC are disclosed herein. The computer system may be provided two or more images. The computer system may assess an area of an interior chamber of the heart when a provided image of the heart depicts the chamber in a substantially expanded condition (i.e., EDV). The computer system may assess an area of an interior chamber of the heart when a provided image of the heart depicts the chamber in a substantially contracted condition (i.e., ESV). FAC may be assessed by providing at least one or a plurality of images to a computer system. In certain embodiments, a velocity of a blood flow may be provided to the computer system. A time over which a valve may be open for one cycle may be provided to a computer system. A computer system may assess the area of an open aortic valve. A computer system may use the assessed area, blood flow velocity, and time for which the valve was open to assess blood flow across a valve. Mitral regurgitation may be used by a user or a computer system to assess a condition of a heart before or after a procedure.

In an embodiment, the user may design procedures and/or treatments using mitral regurgitation as a standard for a computer system to assess a proposed procedure or treatment. The user may enter data for a diseased heart as well as set a desired mitral regurgitation to a value that the user wishes a proposed procedure to achieve. The computer system, using the patient specific model, may modify one or more features of a heart during a virtual procedure. The computer system may repeatedly modify one or more features until the assessed effect of the procedure achieves the mitral regurgitation value desired by the user.

In an embodiment, an ejection fraction may be assessed using parts of the system and method described herein. An ejection fraction is a useful parameter for a computer system and/or a user to assess a condition of a heart. It is therefore a useful value to assess viability of using the methods described herein. Ejection fraction (EF) is typically calculated by EQN. 2:

$$EF = (100) \times [(EDV - ESV)/(EDV)]. \tag{2}$$

EQN. 2 calculates EF as a percentage from EDV and ESV. Therefore, using the methods and/or systems described herein for assessing EDV and ESV, a computer system may then calculate percent EF.

Figure 62:
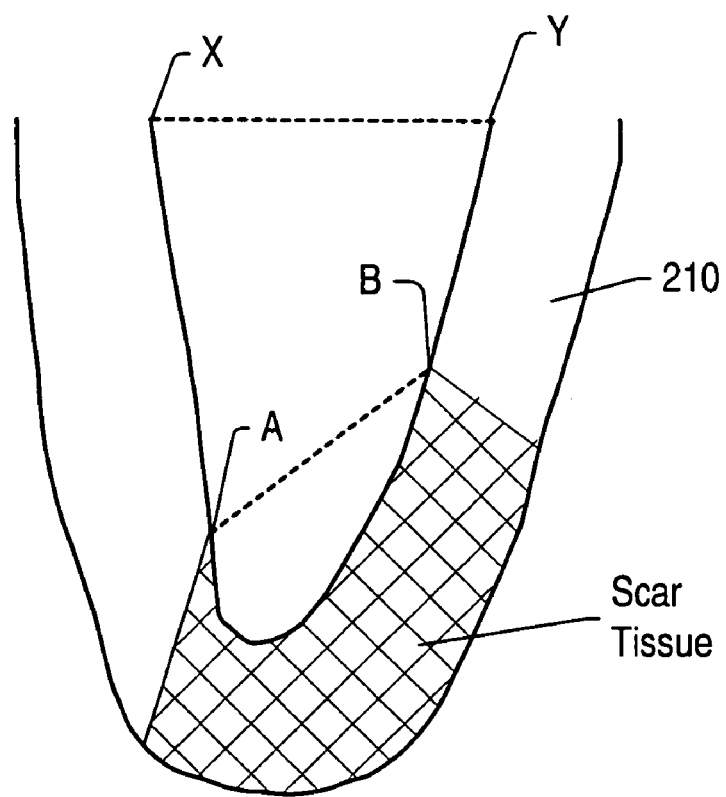
FIG. 62 depicts an embodiment of a pictorial representation of a cross-sectional view of a ventricle and a method of measuring a contractile ejection fraction.

FIG. 62 depicts an embodiment of a pictorial representation of a cross-sectional view of a ventricle and a method of measuring a contractile ejection fraction. In some embodiments, a contractile ejection fraction may be assessed using a model of a heart or a left ventricle. The contractile ejection fraction may be assessed automatically by a system. The contractile ejection fraction is typically a measurement of an ejection fraction of only the viable tissue in a heart. In an embodiment, a model of a ventricle 210 may be created. Scar tissue and/or akinetic tissue may be modeled. A hypothetical plane or curve (depicted by points A and B) on the model may be created to define the contractile portion (e.g., "selected portion of heart") and non-contractile portions based on the scar tissue and/or akinetic tissue. Based on the hypothetical planes/curves AB and XY, end diastole ("$EDV_2$") and end systole ("$ESV_2$") volumes of the selected portion of heart may be calculated. These volumes may be used to assess the contractile ejection fraction ("CEF") of the selected portion of the heart. The contractile ejection fraction may be assessed according to EQN. 3.

$$CEF = [(EDV_2 - ESV_2)/EDV_2] \tag{3}$$

In some embodiments, a contractile ejection fraction may be calculated by excluding either scar tissue and/or akinetic tissue using theoretical plane AB. Although FIG. 62 depicts AB as a plane, AB may also include a curved and/or irregular surface.

In an embodiment, a computer system may be provided a plurality of images of human heart tissue. At least a three-dimensional image of the heart may be created by the computer system from the plurality of images. Features of the heart may be derived directly from the images. In some embodiments, features of the heart may be extrapolated from the images. Extrapolated features may used by the computer system to fill in missing data not found directly in provided images. Features may be identified by the computer system by comparing varying contrasts of portions of the provided images. An image of the assessed ejection fraction percentage may be created by the computer system. In one embodiment, a four-dimensional image representing the ejection fraction percentage of the heart may be created. The four-dimensional image may display the heart going through an entire cardiac cycle, from systolic to diastolic.

In an embodiment, a user may design procedures and/or treatments using an ejection fraction as a standard for a computer system to assess a proposed procedure or treatment. The user may enter data for a diseased heart as well as set a desired ejection fraction percentage for a proposed procedure to achieve. The computer system, using the patient specific model, may modify one or more features of a heart during a virtual procedure. The computer system may repeatedly modify one or more features until the assessed effect of the procedure includes the desired ejection fraction percentage.

In some embodiments, an automated method for assessing whether a subject is a good potential candidate for a specific cardiac procedure and/or treatment may be provided. Specific parameters may be input into a system by which to classify whether a patient is a good potential candidate for a specific cardiac procedure and/or treatment. In an embodiment, a system may automatically refine and update input parameters based on new data. For example, whether a subject is a good candidate for a revascularization procedure may be based up certain selection criteria (e.g., akinetic area>X, non-viable area<Y). Selection criteria for left ventricle reconstruction may be based on a predetermined amount of non-viable tissue and/or a predetermined ejection fraction (e.g., EF<35%). Selection criteria for mitral valve repair may be based on relative papillary muscle distances, relative papillary muscle angles, and/or mitral regurgitation. Selection criteria for defibrillator therapy may be based on ejection fraction (e.g., EF<30%). Selection criteria for biventricular pacing may be based on QRS (e.g., QRS>150 ms) and/or EDV. Detection/diagnosis of hypertrophic heart failure may be based on EDV and/or existence and/or extent of non-viable heart tissue. Effectiveness of drug regiments (i.e., treatments) may be based on predetermined criteria such as ventricular contraction and/or peak ejection velocity relative to pre-treatment levels.

In an embodiment, a model may be accessed at a central location and the images of pre- and post-treatment images may be stored and categorized by disease type, surgical procedure, outcome, etc. at the central location. A database may be used in performing retrospective studies on the efficacy of different procedures and approaches for different disease states and/or patients. A database and analysis may contribute to the advancement and refinement of models and help improve their viability. A database may be used to analyze treatments to compare and empirically demonstrate which are the better treatments for certain patients. A database may allow users to compare results with the database population. A user may see if his selection of and performance of treatment options are better, equal to, or worse than a group as a whole. If he is worse than the group, the surgeon may use a database to help improve his treatment selection process and/or his technique. In an embodiment, a database may include data and/or parameters based on "expert opinion." Expert opinion may include data (e.g., parameters and features) extrapolated and/or derived from personal knowledge and/or experience of specialists within a particular field. The database may be constantly updated and refined as needed or desired.

In some embodiments, a method as described herein may include assessing a cost to be charged to a user for using the method based on a number of times the user applies the method. In an embodiment, a client/user may be charged a fee for use of a method and/or system based on an amount purchased. A consistent pricing system may be set up. Different pricing systems may be used for different clients and/or different types of clients. For example, private industry may be assessed a different fee scale as opposed to academic institutions.

In response to these and other problems, an improved apparatus and method is provided for capturing the geometry of a heart and its components using imaging technologies such as, but not limited to, MRI imaging, echocardiography, or PET. Using imaging information, along with other factors, may be used to create a multi-dimensional finite element computer model of a heart. A model may display not only the three dimensions of the geometry of the heart but may also depict the geometry as it changes over time. A model may run on a personal computer, may run at a central location or the model may be processed at one location and delivered to another location to be run. A multi dimensional model may allow a user to visually inspect the status of all the elements of the heart. A method and system may be used to determine a variety of information, either pre-treatment, during the treatment, or post-treatment, including, but not limited to:

a. The areas of the mitral apparatus, aortic, tricuspid or pulmonary valves that may need to be repaired or replaced and what affect each repair may have on the other components;

b. What vessels are blocked and may need to be grafted, where to graft, and what affect the revascularized muscle may have on the other components;

c. What areas of the ventricle are akinetic, dyskinetic, or hibernating, to show what areas may be excluded during ventricular restoration and what effect the exclusion may have on the other components and aspects of the ventricle and heart;

d. How this patient's heart may respond to medication treatment;

e. The effects of placement of an Acorn, Myocor, or other device on the outside of the ventricle and how such placement may affect the heart;

f. The effects of chordae length adjustment or papillary base relocation and how such changes may affect the heart;

g. The effects of placement of any ventricular assist device and the affect such devices may have on the heart;

h. What vessels are blocked and may need to be stented, where to stent, and what affect the revascularized muscle may have on the other components of the heart;

i. A volume of a portion of a heart including, but not limited to, an interior chamber of a heart (e.g., end diastolic volume or end systolic volume);

j. An ejection fraction of a heart;

k. Percentage and position of viable and nonviable human heart tissue;

l. An assessment of motion of a portion of a heart (assessed motion may allow a system or user to assess a viability of human heart tissue);

m. A degree of transmurality of scar tissue in a heart (the method may also assess a wall thickness of a heart);

n. Distance and angle between papillary muscles, which may assist in assessing a condition of a mitral valve in a heart;

o. A shape of a heart;

p. Results of virtual plication procedures may be assessed to find an optimal procedure; and q. Cardiac electrical activity may be assessed after a virtual procedure has been carried out.

A method and/or apparatus may allow a user to select a treatment option and allow the user to manipulate the image and model. A model may analyze what effects the virtual treatment likely has on the cardiac system and display the potential clinical outcomes to a user. The potential outcomes displayed may be, but are not limited to, the following:

a. An estimated performance of the valves and ventricle after the procedure (e.g., regurgitation, reduced flow across the valves, ejection fraction, etc.);

b. A volume and contractile state of the ventricle after excluding tissue;

c. A positioning and performance of the valve apparatuses after reconstruction of the ventricle;

d. A diagnosis of possible diseases and/or irregularities associated with a portion of a heart modeled;

e. Treatment suggestions for an irregularity or disease; and f. Outcomes for proposed cardiac surgery procedures.

The user may select a displayed intervention. In some embodiments, the user may choose to try another treatment. In certain embodiments, the user may choose to modify the current intervention and the cycle may repeat itself. When the user accepts the potential clinical outcomes, the model may produce specifications for the intervention. The specifications may lead to the development of templates, tools, and/or devices to guide the user in translating the virtual intervention on the model to the actual intervention on the heart. In some embodiments, no template, tools, or devices may be needed to perform an interventions. For example, the specification for some surgical procedures (e.g., altering the length of a chordae tendinae) may be sufficient output from the model to allow the user to perform the intervention. In some embodiments, devices may be generated from the models to help the user implement the procedure that the model may have predicted to provide the desired outcome. Furthermore, the use of some or all of above listed factors may be used to evaluate the post-treatment condition of the patient. A database of surgical pathologies, treatments, and outcomes may be gathered, maintained, and analyzed to further refine the treatment of cardiac diseases and disorders.

In an embodiment, a database may assist in determining, before the treatment, what likely effects the treatment may have on one or more elements of the heart. The database may help to optimize the treatment of each component relative to other components in order to achieve the desired performance of the entire cardiac and/or circulatory system. The method and apparatus may allow the user to simulate numerous interventions and allow him to compare the different simulations so that he may perform the option that provides the desired outcome. Some of these interventions include, but are not limited to, placement of a Myosplint (Myocor Inc., Maple Groove, Minn.), placement of Corcap restraining device (Acorn cardiovascular Inc, St. Paul, Minn.), valve replacement (St. Jude Medical, St. Paul, Minn.), annuloplasty (Edward Lifesciences, Irvine, Calif.), surgical ventricular restoration (Chase Medical, Richardson, Tex.) stent placement (Medtronic, Minneapolis, Minn.), valve repair (Edward Lifesciences, Irvine, Calif.), bypass grafting, pacing, Biventricular pacing (Medtronic, Minneapolis, Minn.), and ventricle assist device (Abiomed, Danvers, Mass.). Surgical Ventricular Restoration (SVR) may be improved by providing a method and apparatus where a user may take an image of a patient's heart or ventricle and create an interactive multi-dimensional model with features. The user may manipulate the model by deleting, adding, or rearranging features to simulate the SVR procedure. The model may integrate all the manipulations relative to each other and interact with other models such as, but not limited to, physiological and hemodynamic models. The interactive multidimensional model may recreate the patient's heart or ventricle based on the manipulations conducted by the user. The model may depict the new ventricle or heart and display cardiac performance characteristics and parameters. The user may perform this simulation numerous times and compare the performance characteristics and select the optimal or desired procedure. The model may produce specifications for the selected procedure from which templates or tools may be created to aid the user in translating the virtual procedure to the real procedure.

As discussed herein, after several or all the structures are geometrically defined and structural properties are known, a finite element model may be created. The general creation of finite element models is well known in the art. Generally, the subject is segmented into many pieces that have closed form solutions. That is, each piece is definable by a linear equation, and hence is a "finite element." Collectively, the linear equations of the pieces form a system of equations that are simultaneously solvable. Computer programs exist for simulating finite element analysis in various applications. For example, design engineers use finite modeling programs. Typically, many thousands of elements are created to model a subject object and in particular three-dimensional objects. For each element, there is geometric information such as an x-y-z coordinate at a point in the element, an element type, material property, stress value, displacement value, thermal value, etc. Such information is definable by linear equations for each of the elements. Finite analysis may be employed to model a subject object.

Problems may arise due to the fact that there are many different methods to create finite element models. Each of these known methods have their own strengths and weaknesses when employed to create finite element models. Some methods may be better at one aspect of creating finite element models, while being relatively poor at performing other aspects of creating finite element models. Examples of methods to create finite element models may include, but are not limited to, correlation method, Fuzzy Region Growing (i.e., FRG) method, various forms of edge detection methods, Hough transform method, and active edge method (i.e., "snakes").

In some embodiments, a method or system for creating images and/or models of human heart tissue that appear multi-dimensional may employ one or more known methods for creating finite element models. In some embodiments, a system for creating multi-dimensional appearing images of human heart tissue may compare one or more results from a first method for creating a finite element model to one or more results from a second method for creating finite element models. In certain embodiments, a system for creating multi-dimensional appearing images of human heart tissue may use the results from several methods for creating a finite element model to complement one another and/or in combination with one another.

Of the different methods available to assist in creating finite element models, several of the methods may be divided into several categories. For example, methods may differ in what aspect of provided data (e.g., images) the methods operate on. For example, in some embodiments, a method may operate on the density and/or intensity of an image. In certain embodiments, a method for creating finite element models may operate on the boundaries and/or the gradient of an image.

In some embodiments, methods of creating finite element models may differ in their initialization. For example, some methods may require an initial solution. An initial solution may take the form of user input. User input may include, for example, a user assessing and/or identifying a particular heart feature and/or portion of a heart feature within an image of human heart tissue. In some embodiments, a method of creating finite element models may not require an initial solution and therefore may be considered self-initialized (i.e., fully automated). In some embodiments, a self-initialized method may provide a required initial solution for a method that is not fully automated (e.g., a method which typically requires user input).

In certain embodiments, methods for creating finite element models and/or segmenting data (e.g., an image) may include methods that operate on the boundaries and/or gradient of an image (i.e., boundary based methods). Boundary based methods estimate the boundaries in an image. Boundary based methods may estimate the boundaries in an image based on the contrast between adjacent pixels of a digitized image. Based on this contrast between adjacent pixels, a border of a structural feature to be assessed may be extracted from among all of the borders detected by the boundary based method. General descriptions of some examples of known boundary based methods are described herein; however, the examples and their descriptions should not be viewed as limiting. Many of the same output products may be arrived at by a variety of mathematical operators known to one skilled in the art and those provided here are merely illustrative examples.

In some embodiments, detection of the border may be accomplished using gradients. A gradient for each point in an image may provide several pieces of information. For example, the gradient may provide the "strength" of the border. The strength of the border may be represented by a magnitude of a vector. The gradient may provide a direction to a maximum brightness. The direction to the maximum brightness may be represented by the direction of the vector.

In some embodiments, gradients may be assessed using the Sobel operation, otherwise known as the Sobel Edge Detector. In brief, the Sobel operation performs a 2-D spatial gradient measurement on an image and thus emphasizes regions of high spatial gradient that correspond to edges. Typically the Sobel operation is used to find the approximate absolute gradient magnitude at each point in an input grayscale image. In theory at least, the operator includes a pair of 3×3 convolution masks, as shown in FIG. 63. One mask is simply the other rotated by 90°. This operation is very similar to the Roberts Cross operator.

Convolution is a simple mathematical operation that is fundamental to many common image processing operators. Convolution provides a way of "multiplying together" two arrays of numbers, generally of different sizes, but of the same dimensionality, to produce a third array of numbers of the same dimensionality. This can be used in image processing to implement operators whose output pixel values are simple linear combinations of certain input pixel values. In an image processing context, one of the input arrays is normally just a gray level image. The second array is usually much smaller, and is also two dimensional (although it may be just a single pixel thick), and is known as the kernel. FIG. 64 shows an example image and kernel used to illustrate convolution. The convolution is performed by sliding the kernel over the image, generally starting at the top left corner, to move the kernel through all the positions where the kernel fits entirely within the boundaries of the image. (Note that implementations may differ in what they do at the edges of images as explained below.) Each kernel position corresponds to a single output pixel, the value of which is calculated by multiplying together the kernel value and the underlying image pixel value for each of the cells in the kernel, and then adding all these numbers together.

So in the example depicted in FIG. 64, the value of the bottom right pixel in the output image is given by EQN. 4:

$$O_{57}=I_{57}K_{11}+I_{58}K_{12}+I_{59}K_{13}+I_{67}K_{21}+I_{68}K_{22}+I_{69}K_{23} \quad (4)$$

If the image has M rows and N columns, and the kernel has m rows and n columns, then the size of the output image will have M−m+1 rows, and N−n+1 columns. Mathematically the convolution can be written as EQN. 5:

$$O(i,j) = \sum_{k=1}^{m}\sum_{l=1}^{n} I(i+k-1, j+l-1)K(k,l) \quad (5)$$

where i runs from 1 to M−m+1 and j runs from 1 to N−n+1. Note that many implementations of convolution produce a larger output image than this because they relax the constraint that the kernel can only be moved to positions where it fits entirely within the image. Instead, these implementations typically slide the kernel to all positions where just the top left corner of the kernel is within the image. Therefore, the kernel "overlaps" the image on the bottom and right edges. One advantage of this approach is that the output image is the same size as the input image. Unfortunately, in order to calculate the output pixel values for the bottom and right edges of the image, it is necessary to invent input pixel values for places where the kernel extends off the end of the image. Typically, pixel values of zero are chosen for regions outside the true image, but this can often distort the output image at these places. Thus, if you are using a convolution implementation that does this, it is better to clip the image to remove these spurious regions. Removing n−1 pixels from the right hand side and m−1 pixels from the bottom may fix the image. Convolution can be used to implement many different operators, particularly spatial filters and feature detectors. Examples, besides the previously mentioned Sobel edge detector, include Gaussian smoothing.

The Sobel convolution masks (as depicted in the examples in FIG. 63) are designed to respond maximally to edges running vertically and horizontally relative to the pixel grid (e.g., one mask for each of the two perpendicular orientations). The masks can be applied separately to the input image to produce separate measurements of the gradient component in each orientation (these can be called Gx and Gy). These gradient components can be combined together to find the absolute magnitude of the gradient at each point and the orientation of that gradient. The gradient magnitude is given by EQN. 6:

$$|G|=\sqrt{Gx^2+Gy^2} \quad (6)$$

Although typically, an approximate magnitude is computed using EQN. 7:

$$|G|=|Gx|+|Gy| \quad (7)$$

which is typically faster to compute. The angle of orientation of the edge (relative to the pixel grid) giving rise to the spatial gradient is given by EQN. 8:

$$\theta=\arctan(Gy/Gx)-3\pi/4 \quad (8)$$

In this case, orientation Θ is taken to mean that the direction of maximum contrast from black to white runs from left to right on the image, and other angles are measured counter-clockwise from this. Often, this absolute magnitude is the only output the user sees—the two components of the gradient are conveniently computed and added in a single pass over the input image using the pseudo-convolution operator shown in FIG. 65. Using this mask, the approximate magnitude is given by EQN. 9:

$$||G|=|(P_1+2\times P_2+P_3)-(P_7+2\times P_8+P_9)|+|(P_3+2\times P_6+P_9)-(P_1+2\times P_4+P_7)| \quad (9)$$

The Sobel operator is typically slower to compute than the Roberts Cross operator, but the Sobel operator's larger convolution mask smooths the input image to a greater extent and so makes the operator less sensitive to noise. The Sobel operator also generally produces considerably higher output values for similar edges compared with the Roberts Cross. As with the Roberts Cross operator, output values from the Sobel operator can easily overflow the maximum allowed pixel value for image types that only support smaller integer pixel values (e.g., 8-bit integer images). When this happens, the standard practice is to simply set overflowing output pixels to the maximum allowed value. The problem may be avoided by using an image type that supports pixel values with a larger range. Natural edges in images often lead to lines in the output image that are several pixels wide due to the smoothing effect of the Sobel operator. Some thinning (i.e., a morphological operation that is used to remove selected foreground pixels from binary images) may be desirable to counter the smoothing effect. Failing that, some sort of hysteresis ridge tracking may be used such as the Canny operator.

In certain embodiments, methods for creating finite element models and/or segmenting data (e.g., an image) may include methods that operate on the density of an image. Density based methods typically consider the intensity of each pixel independent of the intensity of the surrounding pixels. Structures are generated by grouping together "similar" contiguous pixels. General descriptions of some examples of known density based methods are described herein; however, the examples and their descriptions should not be viewed as limiting. Many of the same output products may be arrived at by a variety of mathematical operators known to one skilled in the art and those provided here are merely illustrative examples.

Figure 66:
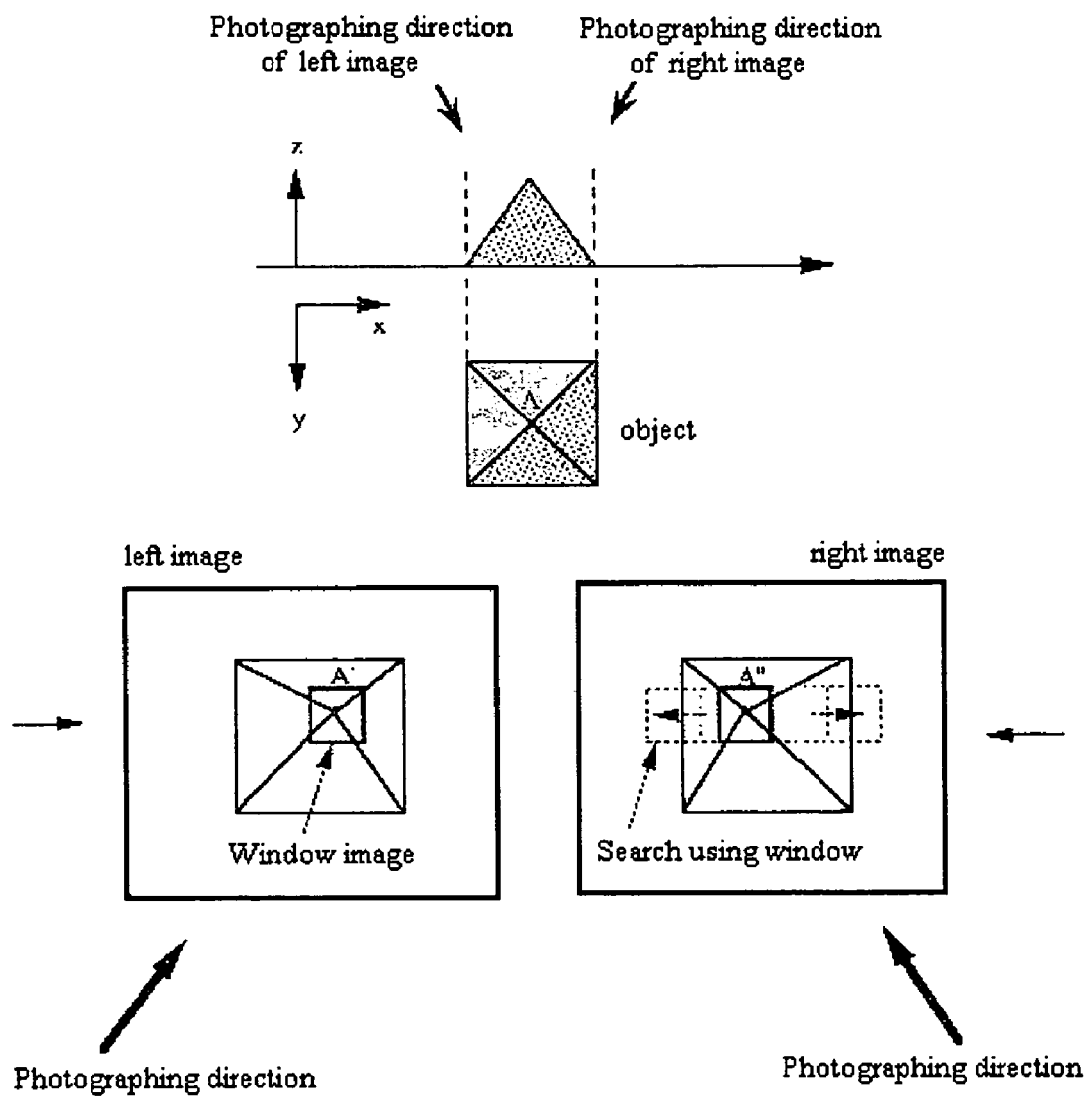
FIG. 66 depicts an embodiment of an example of a conjugate point search (A' and A")on stereo images.

In some embodiments, a density based method used for assessing data (e.g., images) may include a technique commonly referred to as correlation. Correlation is a technique used in pattern matching (i.e., the field of image processing which deals with locating an object inside a picture). Image correlation is a technique by which the conjugate point of a slave image (right in FIG. 66) corresponding to the master image (left in FIG. 66) will be searched for the maximum correlation coefficient. Image correlation is applied to stereo images for DEM (digital elevation model) generation or multi-date images for automated recognition of ground control points. As depicted in FIG. 66, the master window in the left image is fixed, while the slave window in the right image is moved to search for the maximum image correlation as computed from EQN. 10 and/or EQN. 11.

$$r = \frac{(\sum a_i b_i)^2}{\sum a_i^2 \sum b_i^2} \quad (10)$$

$$r = \frac{n\sum a_i b_i - \sum a_i \sum b_i}{\{n\sum a_i^2 - (\sum a_i)^2\}\{n\sum b_i^2 - (\sum b_i)^2\}} \quad (11)$$

where, ai is image data of the master window;
bi is image data of the slave window; and
n is total number of image data.

Because the above two correlations sometimes show almost no difference, the first correlation may be used to save computing time. The size of the window may be selected depending on the image resolution and feature size. For example, 5×5 to 9×9 windows might be selected for SPOT stereo images, while 9×9 to 21×21 may be better used for digitized aerial photographs. When the conjugate points of stereo images are determined, the corresponding digital elevation may be computed using collinearity equations based on photogrammetric theory.

In some embodiments, a method for creating finite element models and/or segmenting data may be used for a specific purpose. In a non-limiting example, correlation may be used to assess a point in the left ventricle of an image of a human heart. Correlation may not be used for the entire segmentation. Correlation may be used as a facilitator for a different segmentation method, for example, providing an initial solution for a method that is, by itself, not fully automated.

Figure 67:
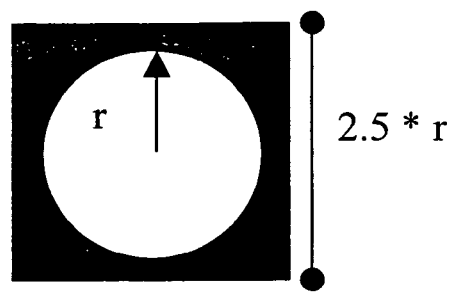
FIG. 67 depicts an embodiment of an example of a template.

For example, typically the left ventricle of a human heart appears as a bright object relative to surrounding tissue with a substantially circular shape in images of human heart tissue. Assuming the left ventricle is a bright substantially circular object, a template, as depicted in FIG. 67, may be used to assist in locating the left ventricle in images of human heart tissue. In some embodiments, several kernels with different values for r may be employed. Using different kernels with different values for r may be advantageous due, in part, to variations in the size of the left ventricle. The size of the left ventricle may be affected by several different factors, some of which may include: field of view included in the image; the patient; and/or the location of the image taken relative to the rest of the heart.

For each point or pixel in an image of human heart tissue, a method based on correlation may center all available templates. Once all of the templates are centered, a correlation value may be computed for each template. All of the correlation values calculated may be assessed and a maximum selected. Correlation values measure how close the portion of the image considered is to the template chosen. In this particular instance, the correlation measures how likely is the pixel considered to be a center of a bright circle surrounded by a darker area as in the example template depicted in FIG. 67. In assessing the location of the left ventricle of a human heart, typically the center of the left ventricle has one of the higher correlation values relative to surrounding tissue. There may be instances when several correlation values are relatively high. Upon computing the correlation value for each pixel, a correlation map or correlation image may be generated. The brightest spots may be chosen from the correlation map and their positions and/or size evaluated. By evaluating the position and/or size of the brightest spots in the correlation map, candidates for the center of the left ventricle may be assessed.

In certain embodiments, methods for creating finite element models and/or segmenting data (e.g., an image) may include methods that operate on the boundaries and/or gradient of an image (i.e., boundary based methods). In some embodiments, a boundary based method may include the Hough transform. The Hough transform is a method used in pattern recognition. The Hough transform is typically used for target identification. The Hough transform is used in computerized image processing and may detect arbitrary shapes in images given a parameterized description of the arbitrary shape sought.

A line in image space with coordinates x and y can be written as EQN. 12:

$$y = y_0 + m*x \quad (12)$$

The Hough method transforms this line into the parameter space generated by m and $y_0$. For each pixel (x,y) in the original image there is a corresponding "line" in parameter space written as EQN. 13:

$$y_0 = y - x*m \quad (13)$$

The Hough transform creates a discrete parameter space, called accumulator, initialized with zeros and transforms every pixel in the original image according to EQN. 13. All accumulator cells found are incremented. In the end, the highest valued accumulator cell is sought as its parameters represent the most probable line in the original image.

In some embodiments, a method for creating finite element models and/or segmenting data may be used for a specific purpose. In certain embodiments, the Hough transform may be used to assess a point in the left ventricle of an image of a human heart and/or segmenting the left ventricle.

In certain embodiments, a modified version of the Hough transform may be implemented to locate a center of the left ventricle. Due to the fact that the left ventricle is not a perfect circle, it may be necessary to use the modified Hough transform to locate the left ventricle and/or the center of the left ventricle. For each pixel in an image a line may be traced along the direction of the gradient. If the pixel under consideration is part of the border for the left ventricle the line will go through the center of the left ventricle. The center of the left ventricle will be the point in which several of the traced lines intersect. The number of lines passing through each pixel are counted. Bright spots in the Hough transform applied to an image may represent the center of a circular shape in the image.

In some embodiments, the position of a septum wall of a human heart may be assessed. The septum wall separates the left and right ventricles of the heart. Upon identifying the centers of the left and right ventricles, the septum wall may be located based upon the position of the centers of the left and right ventricles. In an embodiment, the Hough transform may be used to locate the positions of the centers of the left and right ventricles and display them as bright spots. The septum wall may be identified as a relatively dark region between the two bright spots.

In some embodiments of septal segmentation, pre-contrast TrueFISP images and segment septal contours from septal segmentation images may be used. The septal contours may be constrained by existing endocardial and/or epicardial contours. These contours may be placed onto a two-dimensional bullseye plot. The contours on the bullseye plot may be wrapped using spline interpolation to smooth the septum.

Segmentation of the septal wall can become increasingly difficult as the images approach the end-systolic phase. This may be due to heavy concentration of right ventricular apical trabeculation causing indistinct border regions in this area. In the images around the end-diastolic phases the apical trabeculation of the right ventricle is more spread out and potentially allows the boundary of the right ventricle to be more easily visualized.

The septum may be used for at least two reasons. For location information, if the user knows the location of the septal wall within the left ventricular reconstruction, the three-dimensional model may be moved to known anatomical orientations. Secondly, the septum may be used in at least one important calculation (e.g., 'Percentage of septal involvement'). This calculation may tell the user how much of the septal wall is non-viable tissue. The primary use of septal segmentation may not rely on accurate segmentation and may only require that the septal region be highlighted. The second use of septal segmentation may require relatively accurate segmentation so that the septal involvement calculations may also be accurate.

The septum may need to be fairly accurately segmented in the same cardiac phase that non-viable tissue is segmented. Providing that both these structures are accurate in the same cardiac phase, septal involvement calculations may also be accurate. This gives an advantage in that non-viable tissue images are captured close to the end-diastolic phase and segmentation of the septum is less of a problem in this time frame. If the non-viable tissue is not exactly in the end-diastolic phase. it may be possible to segment the septum in the end-diastolic phase as both phases can be close and there may not be any great change in the septal triangle between these phases.

In certain embodiments, the septum may be segmented in the same phase as non-viable tissue and then wrapped using a bullseye plot similar to that used for non-viable tissue (see FIG. 55 for an example of a bullseye plot). Assuming that every three-dimensional model across the cardiac cycle is created in a uniform manner, vertices may be labeled as septal in the non-viable tissue phase. These vertex labels may be used throughout the rest of the cardiac cycle.

Segmentation of the septum in end-diastole may be easier in the four-chamber images. In some embodiments, the length of the septum may be taken from long-axis segmentation in a four-chamber image and combined with the short axis segmentations.

Figure 68:
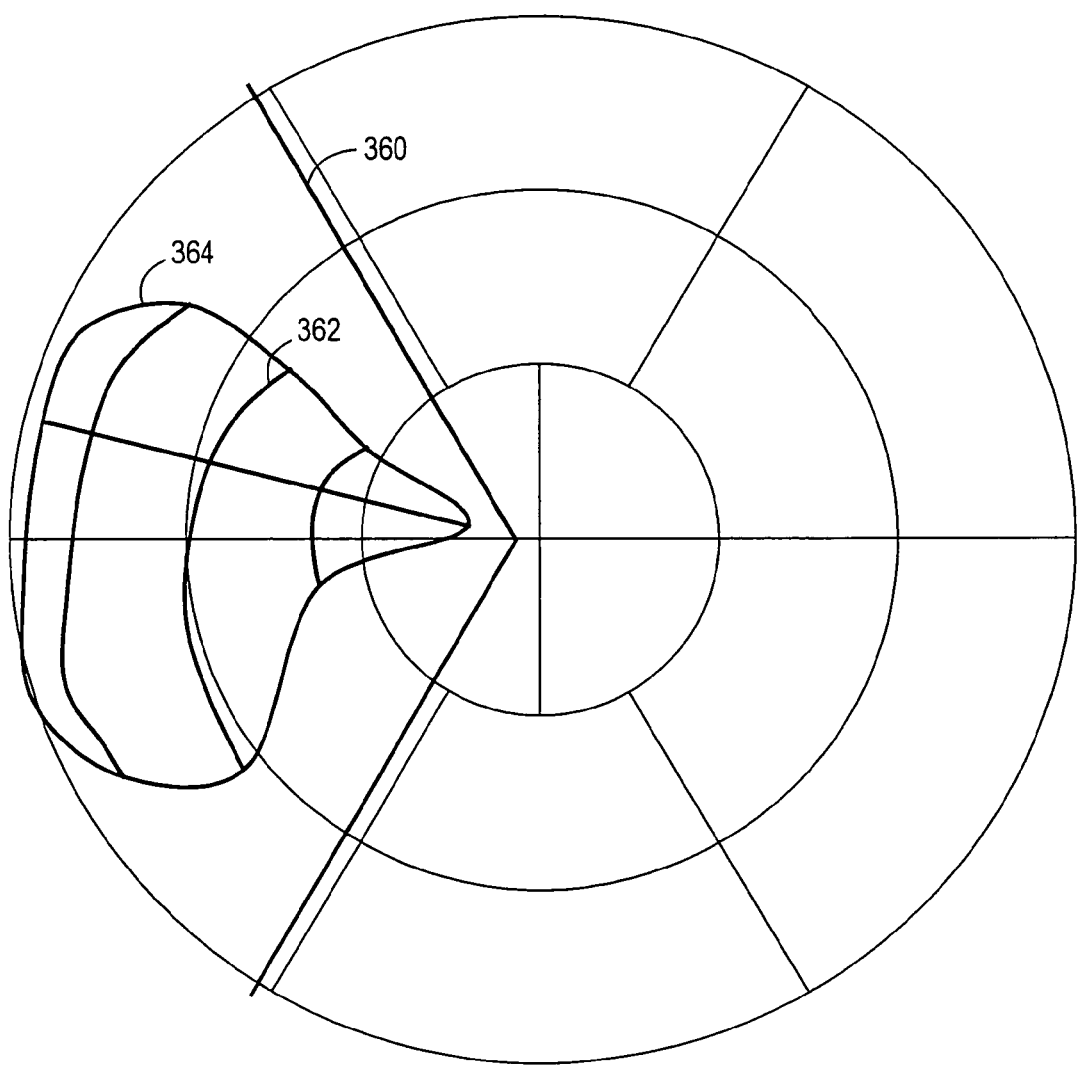
FIG. 68 depicts an embodiment of an example of a bullseye plot with an example anatomical septum interpolated from septal contours that have been segmented from long and short axes.

The anatomical septum that is segmented may not be an exact sector of a circle as represented by the bullseye plot. The segmented septum may, however, be aligned to the septal sector of the bullseye plot to ensure that the user can correctly identify regions of the heart on the bullseye plot. This may be achieved using simple rotation. For ease of further calculations, short axis endocardial and epicardial contours may be zeroed to the bullseye mid-septum. FIG. 68 shows a bullseye plot with an example anatomical septum interpolated from septal contours that have been segmented from long and short axes. The anatomical septum may be centered in the bullseye septum. Contours may be created with zero point at the center of the bullseye septum. Both model bullseye and anatomical septum may be registered. Lines 360 mark the extents of the bullseye septal segment. Line 362 represents the segmented short and long axis septal contours. Line 364 represents the interpolated septum.

Figure 69:
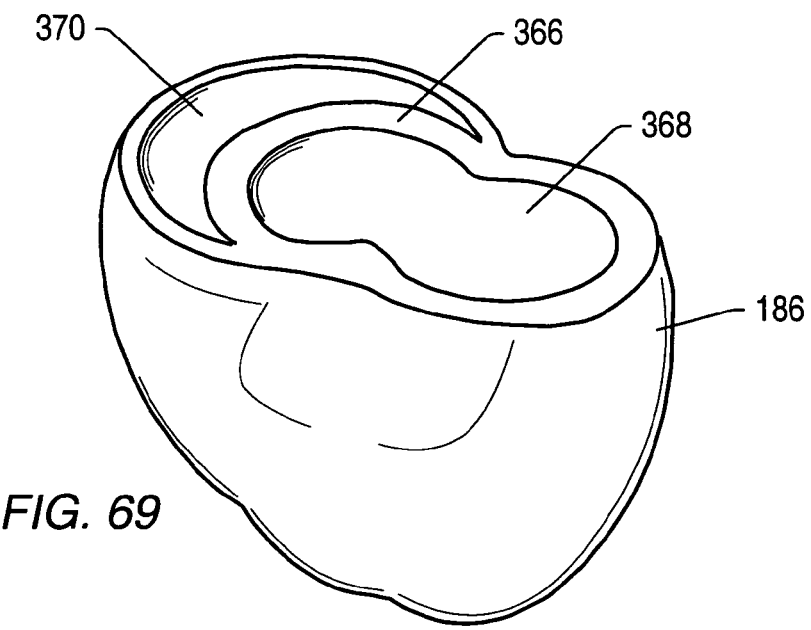
FIG. 69 depicts an embodiment of a pictorial representation of a cross-sectional view of a heart.

FIG. 69 depicts an embodiment of a pictorial representation of a cross-sectional view of a heart 186. In certain embodiments, the position of septum wall 366 of a human heart may be assessed. Left ventricle 368 may be identified, specifically the left ventricle cavity. The left ventricle cavity may be modeled. The left ventricular wall may be modeled. Right ventricle 370 may be identified. The right ventricle cavity may be modeled. A portion of the right ventricle cavity which is adjacent the left ventricle wall may be identified. Identifying the portion of the right ventricle cavity which is adjacent the left ventricle wall may assist in identifying and/or modeling the septum wall. Modeling any of the elements of the heart to identify the septum wall may include an automated segmentation method. Automated segmentation methods may be based on known methods or on modifications of known methods described herein. Identification of the cavities may be based on the intensity or density of areas or sections of images provided to a computer system.

In certain embodiments, methods for creating finite element models and/or segmenting data (e.g., an image) may include methods which operate on the density of an image. Density based methods typically consider the intensity of each pixel independent of the intensity of the surrounding pixels. Structures are generated by grouping together "similar" contiguous pixels.

In some embodiments, a density based method used for assessing data (e.g., images) may include a technique commonly referred to as Fuzzy Region Growing (FRG). FRG keeps extending the threshold to include lower and lower densities until the change in the numbers of pixels included increases by a predetermined amount. An increase of equal to or greater than a predetermined amount in the number of included pixels typically indicates that the FRG has "bled" or "grown" from one feature (e.g., a structural feature of a human heart) to a second feature.

In certain embodiments, FRG may be employed to extract the location and shape of the left ventricle of the human heart from an image by:

a. Given a seed point with density, d, include in the region all the pixels with density higher than d and measure their number; and b. For each step, i, consider the number of pixels with density greater than d-i and adjacent to the region selected. If the number of pixels now considered is small relative to the number already included in the region, then extend the region, otherwise stop.

In certain embodiments, left ventricle wall segmentation may work in a similar fashion to the segmentation of the left ventricle. Segmentation of the left ventricular wall may differ from segmentation of the left ventricle in that the segmentation may be initialized with all the pixels outside the boundary of the left ventricle.

Many of the methods described herein for creating finite element models and/or segmenting data (e.g., an image) may be capable alone or in combination with another method to determine most or all of the borders in a digital image. Many of these methods, however, have a common problem in that these methods may not be able to assign any of the determined borders to a particular feature (e.g., a structural feature in a human heart). In some embodiments, a gradients method may be used to assign a determined border in a digital image to a particular feature.

In some embodiments, a gradients method may be used to assess among all of the detected borders in a digital image which border(s) belongs to a left ventricle and which border(s) belong to the left ventricle wall. For the determination of the left ventricle border, a gradients method may select a first candidate (e.g., a pixel with high gradient strength) moving radially from the left ventricle center. In a similar fashion, the left ventricle wall border may be determined as a first candidate moving radially from the left ventricle center after the left ventricle border.

In some embodiments, a gradient coherency method may be used to assign determined borders in a digital image to a particular feature. Gradient coherency considers the gradient direction and how much the gradient points toward the center of, for example, the left ventricle for each border. Gradient direction may allow a system to discriminate several candidates for the identification of the left ventricle border.

In certain embodiments, methods for creating finite element models and/or segmenting data (e.g., an image) may include methods that operate on the boundaries and/or gradient of an image (e.g., boundary based methods). In some embodiments, a boundary based method may include "active contours" (i.e., snakes). Snakes, or active contours, are curves defined within an image domain, which can move under the influence of internal forces within the curve itself and external forces derived from the image data. The internal and external forces are defined so that the snake conforms to an object boundary or other desired features within an image. Snakes are widely used in many applications including edge detection, shape modeling, segmentation, and motion tracking.

There are two general types of active contour models in the literature today: parametric active contours and geometric active contours. Parametric active contours were originally developed by Kass, Witkin, and Terzopoulos. In parametric active contours formulation, the image data are used to define potential functions over the image domain. Usually, these potential functions have local minima at the image intensity edges that occur at object boundaries. Parametric curves are then synthesized within the image domain and are forced to move toward the potential function minima. The forces that move the curve are formed in part by the negative of the gradient of the potential function itself (i.e., potential forces). Additional forces, such as pressure forces, together with the potential forces comprise all the external forces. There are internal forces designed to hold the curve together (elasticity forces) and to keep it from bending too much (bending forces).

More recently, geometric active contour models were proposed by Caselles et al. and Malladi et al. Based on the theory of curve evolution and geometric flows, these models define a geometric active contour as a level-set of an evolving scalar function defined on a spatial domain. The computations causing the scalar function to change are based on a numerical algorithm proposed by Osher and Sethian.

Caselles has shown that parametric active contours and geometric contours are basically equivalent and that one formulation can be derived from the other. One basic difference, however, is in the handling of what is sometimes called "the topology problem." In particular, when there are several objects in the scene, the topology of the final curve is object-dependent and the algorithm must adjust. In the geometric active contour formulation, this is handled automatically since the parameterization of the level-set is calculated only after convergence. In the parametric active contour formulation, more extensive measures need to be taken to split active contours into two or more pieces or to instantiate separate active contours at different locations. Except for topological differences, however, the behavior of both active contour models is fundamentally characterized by the external and internal forces of the formulation.

There are three key difficulties with active contour algorithms. First, it is well known that the initial contour, in general, must be placed close to the boundary or else it will likely converge to the wrong result. Several methods have been proposed to address this problem including scale-space methods and pressure forces. The basic idea is to increase the "capture range" of the external fields and to guide the contour toward the desired boundary. The second problem is that active contours are known to have difficulties progressing into concave boundary regions, often leaving the contour split across the concave region. There is no satisfactory solution to this problem, although pressure forces, control points, adding nodes, and using solenoidal external fields have been proposed. The third problem stems from the fact that most algorithms use potential forces derived from a low-pass filtered image in order to increase the capture range. Unfortunately, this filtering also blurs the boundary detail, leaving the snake to converge to a blurry boundary. While multi-resolution approaches have addressed this problem, determining the required resolution for a given snake position is difficult to determine and leads to ad-hoc methods.

Active contours do provide several benefits when using them for segmenting an image. One advantage of active contours is allowing features with poorly defined boundaries to be segmented. A second advantage of active contours is allowing for the quantification of the similarity between a found solution and a desired solution. Many other methods discussed herein are sensitive to noise in an image. Other methods are mainly based at pixel level solutions and they do not consider the region segmented and the region's shape as a whole. Methods other than active contours tend to work poorly where the border is weak or nonexistent. In the case of active contours, the image as a whole is assessed based on that the shape of the object sought is known. Active contours offer the possibility to overcome some of the limitations of other methods described herein.

Active contours may be used to quantitatively measure the reliability of the solutions of other methods. Other methods may provide a solution that is close to the correct solution for a given feature. In some embodiments, active contours may be used to optimize a solution found using the gradients methods, FRG method, and/or Hough transform. In certain embodiments, active contours may be used to select and/or evaluate which method provides the best solution. For example, active contours may harmonize the shape segmented making sure boundaries are smooth. Smoothing the boundaries may involve changing the boundaries of the solution where the image does not present any boundary and in areas where very likely the original method failed.

In certain embodiments, a system and/or method may evaluate a quality of a solution of a method described herein and/or a method similar to one described herein. The ability of a system to assess the quality of a solution of a method may allow the system to quantitatively compare solutions from different segmentation methods. The ability of a system to assess solutions from different methods may allow the system to determine an optimal solution. In some embodiments, assessment by a system of solutions from different segmentation methods may be substantially automated.

In some embodiments, a system may evaluate a quality of a solution of a method by analyzing a histogram of densities contained in two or more related features in an image. In certain embodiments, two related features in an image may include the left ventricle of a human heart and the left ventricle wall of the human heart. In embodiments with solutions from segmentation methods based on different assessment criteria, an unbiased quantitative comparison of the solutions may be provided. For example, when a solution from an active contours method is compared to a solution from a density based method, an unbiased quantitative comparison may result due to the active contours method considering only the borders of an image and not considering the brightness of the pixels as in the density based method.

Once the two regions of an image(s) of related features have been segmented, the two histograms may be calculated. The histograms may be normalized. Normalizing the histograms may allow the solutions to be interpreted as posteriori probabilities. Normalization is advantageous in that normalization removes any dependency on the actual number of pixels present in the two related features and thus allows the comparison of values in the two histograms.

Figure 70:
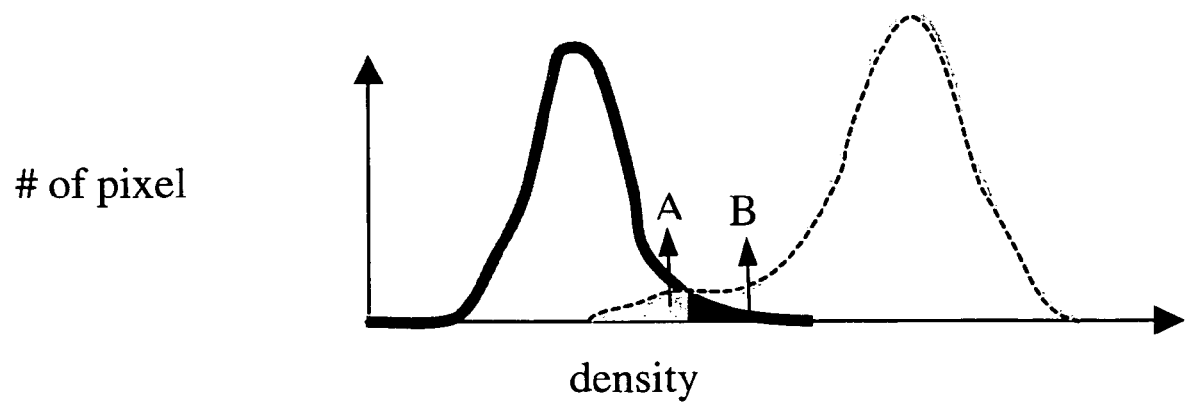
FIG. 70 depicts an embodiment of an example of two histograms of segmentation data from a left ventricle and a left ventricle wall of a human heart.

In an example of an analysis of a solution of two related features of an image of human heart tissue, one may consider the left ventricle and the left ventricle wall. In a general example, the two histograms of the left ventricle and the left ventricle wall may overlap as depicted in FIG. 70. FIG. 70 depicts an embodiment of an example of two histograms of segmentation data from a left ventricle and a left ventricle wall of a human heart. The darker line in the histograms depicted represents a histogram of the left ventricle wall. The lighter line in the histograms depicted represents a histogram of the left ventricle. Both histograms have been normalized such that the area (i.e., integral) is of Area A is such that $\text{Histogram}_{Lvw}(i) > \text{Histogram}_{Lv}(i)$ and of Area B is such that $\text{Histogram}_{Lv}(i) > \text{Histogram}_{Lvw}(i)$.

In this particular example including the left ventricle and the left ventricle wall, because of the presence of papillary muscle in the left ventricle, it is expected there are some low densities in the left ventricle. However, the left ventricle wall has a relatively larger number of such low densities due to the fact they are characteristic of the left ventricle wall. Because of this, overlapping in the area designated as A is expected. When segmented properly, a minimal amount of bright densities are expected in the left ventricle wall due to lack of contrast in the image segmented for the example given in FIG. 70. In an ideal situation the number of pixels in area B should be zero. Therefore, area B may be considered as a relatively accurate measure of the error in the segmentation method. Relatively high numbers for area B may indicate a problem with the segmentation method used.

In some embodiments, a method may be used in the three-dimensional reconstruction of non-viable tissue. The non-viable tissue may be located within the left ventricle wall. Single-plane, multi-phase TrueFISP images may provide anatomical information relating to the structure of the left ventricular wall. Gadolinium single-plane, single-phase images may highlight the non-viable tissue resulting from myocardial infarction through hyper enhancement. Epicardial and endocardial boundaries may be segmented from the TrueFISP images. Gadolinium hyper enhancement images may be registered to the TrueFISP images so that non-viable tissue segmentation is more accurately constrained to the left ventricular wall. The anatomical three-dimensional model may be constructed of short-axis style contours, each of n evenly spaced points, where n is fixed across the entire model.

True three-dimensional reconstruction and correct localization of non-viable tissue is not generally a simple task. Several challenges typically exist in initially segmenting the non-viable tissue and in reconstructing the non-viable tissue in a way that is consistent with a design of an anatomical model. Typical challenges may include:

Determining each 'side' of the non-viable tissue, both epicardial and endocardial;

Positioning of the segmented non-viable tissue correctly within the wall; and

Successful creation of a scarred area from sampled scar points, i.e., from scars highlighted in images that are discrete.

Figure 71:
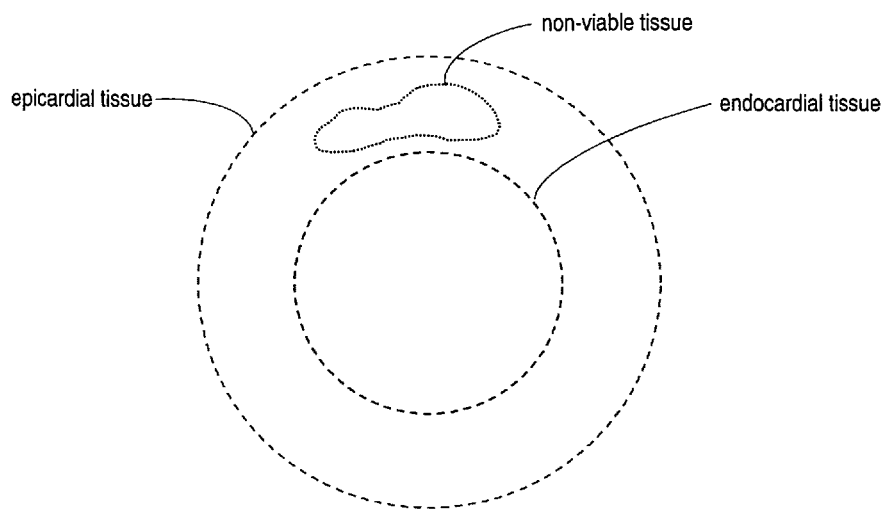
FIG. 71 depicts an embodiment of an image of segmented contours.

Three-dimensional models may be created from short-axis style contours. Each model may have a set number of evenly spaced points. A system (e.g., a computer system) may segment non-viable tissue as closed contours with the same number of points. This may more accurately portray the exact shape of the non-viable tissue. Measurements that are performed, including both measurement of the wall points and the non-viable tissue points, may, however, become more complicated. Thus, the non-viable tissue contours may be created in a similar fashion to the wall contours. FIG. 71 depicts an image of an embodiment of segmented contours including the epicardial contour, the endocardial contour, and the non-viable tissue.

As shown in FIG. 71, the number of points per contour may be relatively uniform. The density of points, however, may be much greater in the non-viable tissue contour. By evenly spacing the contour points in all contours, measurements such as wall thickness may be obtained far more easily.

Figure 72:
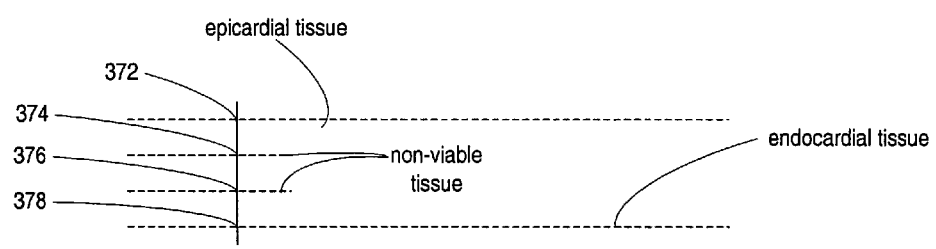
FIG. 72 depicts an embodiment of a short-axis contour after a polar to rectangle co-ordinate change.

FIG. 72 depicts an embodiment of a short-axis contour after a polar to rectangle coordinate change. Where non-viable tissue is present, four points exist; epicardial point 372, non-viable tissue point 374 closer to the epicardium, non-viable tissue point 376 closer to the endocardium, and endocardial point 378. The solid perpendicular line intersects an example set of these points.

Figure 73:
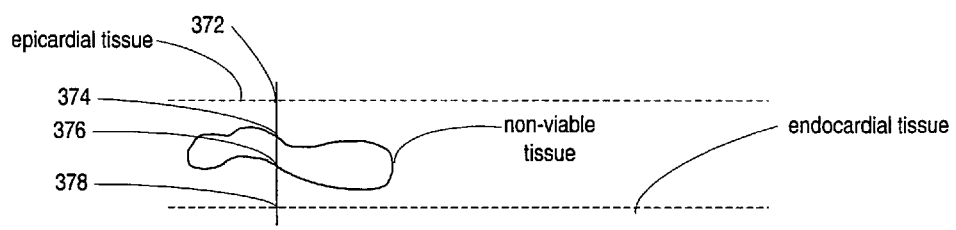
FIG. 73 depicts an embodiment of a diagrammatic representation of non-viable tissue contours in a left ventricle wall.

The diagrammatic representation of the non-viable tissue contours may not highlight the complex nature of the contours usually present in the left ventricle wall. A more accurate representation is depicted in FIG. 73. FIG. 73 depicts an embodiment of a diagrammatic representation of non-viable tissue contours in a left ventricle wall. Non-viable tissue scar is typically continuous until the tissue is segmented, at which point the tissue becomes a discrete set of points. These points, however, may not keep with the point spacing of the ventricular wall.

The solid perpendicular line of intersection shown in FIGS. 72 and 73 presents a possible solution to the problem. The non-viable tissue may be sampled along the intersection line to create points in keeping with that of the model. The position of the three-dimensional scar within the wall post-reconstruction may also be determined.

Figure 74:
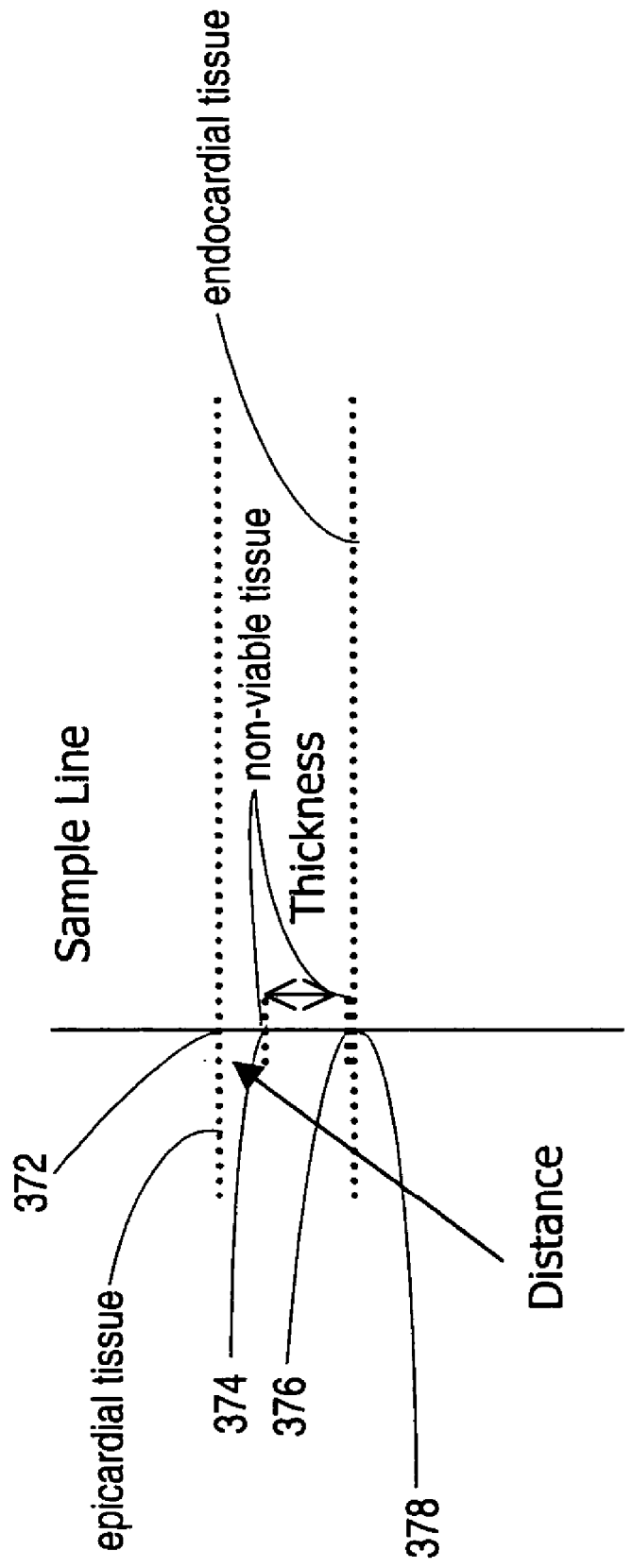
FIG. 74 depicts an embodiment of a diagrammatic representation of a sub endocardial scar.

By looking for non-viable tissue along any line defined by an epicardial/endocardial pair of pixels (as the contours are evenly spaced), two outer non-viable tissue points may be determined. In certain cases where the non-viable tissue at a sample line extends from the epicardium to the endocardium, the scar may be transmural. In cases where the non-viable tissue at a sample line does not extend from the epicardium to the endocardium, the scar may be classified as sub-endocardial (as depicted in FIG. 74). The method may allow measurement of the scars thickness and position. So for every pixel pair 1->n (epicardium and endocardium) it is possible to sample a non-viable tissue pixel pair from the hyper enhancement image.

In some embodiments, after applying the above described method to every short and long axis image, a non-viable tissue set of points may be created for every epicardium/endocardium pixel pair in the entire model. At some points in a model, there may be no non-viable tissue but these set members can be set to null.

The existence of non-viable tissue may be checked at any point in the model. The thickness and location of non-viable tissue may be determined at a certain location due to the sampled information.

In certain embodiments, scar wrapping using a two-dimensional bullseye plot for visualization may be used with the sampled points instead of the contours. One bullseye may be plotted for each non-viable tissue 'side' (e.g., inner and/or outer). Once the wrapping has been determined on this pair of bullseye plots the sampled distance data may be used to reposition these points back into the model at their exact location. A wire frame scar may be generated. A triangulation method may be applied.

A software system may be developed to encompass more and more metric values requested by clinical users. The addition of algorithms to perform measurements on a model with known point positions and locations may be invaluable. Current ray-tracing algorithms may be implemented and work without significant timing problems. New algorithms for complex wall motion analysis, however, may be needed. A model that has both walls and non-viable tissue constructed in a method as described herein may be more easily incorporated in complex wall motion analysis.

In certain embodiments, a method may include multi-dimensional modeling of at least portions of a human body (e.g., a heart). The method may include a specific segmentation protocol of images acquired of heart tissue. In some embodiments, a specific segmentation protocol may include a modified Active Appearance Model ("AAM"). The segmentation protocol may include what may be termed herein as "Delta Analysis." The segmentation protocol may also include what may be termed herein as "Constraint of the Segmentation." AAM was derived from the Active Shape Models ("ASM")based on snakes. ASM was modified by replacing energy minimizing splines with Point Distribution Models ("PDMs"). PDMs represent shapes as a "mean and variations" within a family of shapes. The resulting method is similar to snakes, but with the added restriction that the generated shape must fall within the plausible set of shapes governed by its family features. ASM may not take advantage of all the information present in an image. ASM may make use of edge and shape data, but it does not utilize texture (i.e., pixel intensity). Other disadvantages of ASM can include susceptibility to noise, local minima, and/or initialization biases.

AAM was developed to overcome the deficiencies of ASM. Building on ASM's shape representation, a texture model was added. Together the two allow AAM to model an object appearance. Segmentation within AAM, as opposed to ASM, now involves minimization of differences in appearance between the model and the object of interest.

Delta analysis may function to assist in limiting an area of one or more images to be segmented. For example, many images provided to a system that carries out the method are provided by an MRI system. It should be noted that although MRI images shall be used as an example they should not be seen as limiting, but merely as one embodiment. Data from other diagnostic medical devices described herein may also be used. NRI images typically include at least a majority of a cross section of a human body. Thus, images provided by MRI may include a great deal of data that is not of interest to a user. Due to the intense computational power typically required by known segmentation protocols, it may be advantageous to first limit the area to be studied to a particular region of interest ("ROI"). In certain embodiments, an ROI may include, but is not limited to, cardiac tissue. In some embodiments, an ROI may include any organ or area of the human body (e.g., the lungs, heart, liver, etc.). In certain embodiments, an ROI may include the left ventricle of a heart. Delta analysis may be relatively less computationally intensive than, for example, the constraint of the segmentation or the actual segmentation. Narrowing a region of study to a ROI using a less computationally intensive method may advantageously increase the speed and/or efficiency of the segmentation method. Narrowing a region of study to a ROI using a less computationally intensive method may advantageously decrease associated time and costs of the segmentation method.

Figure 75:
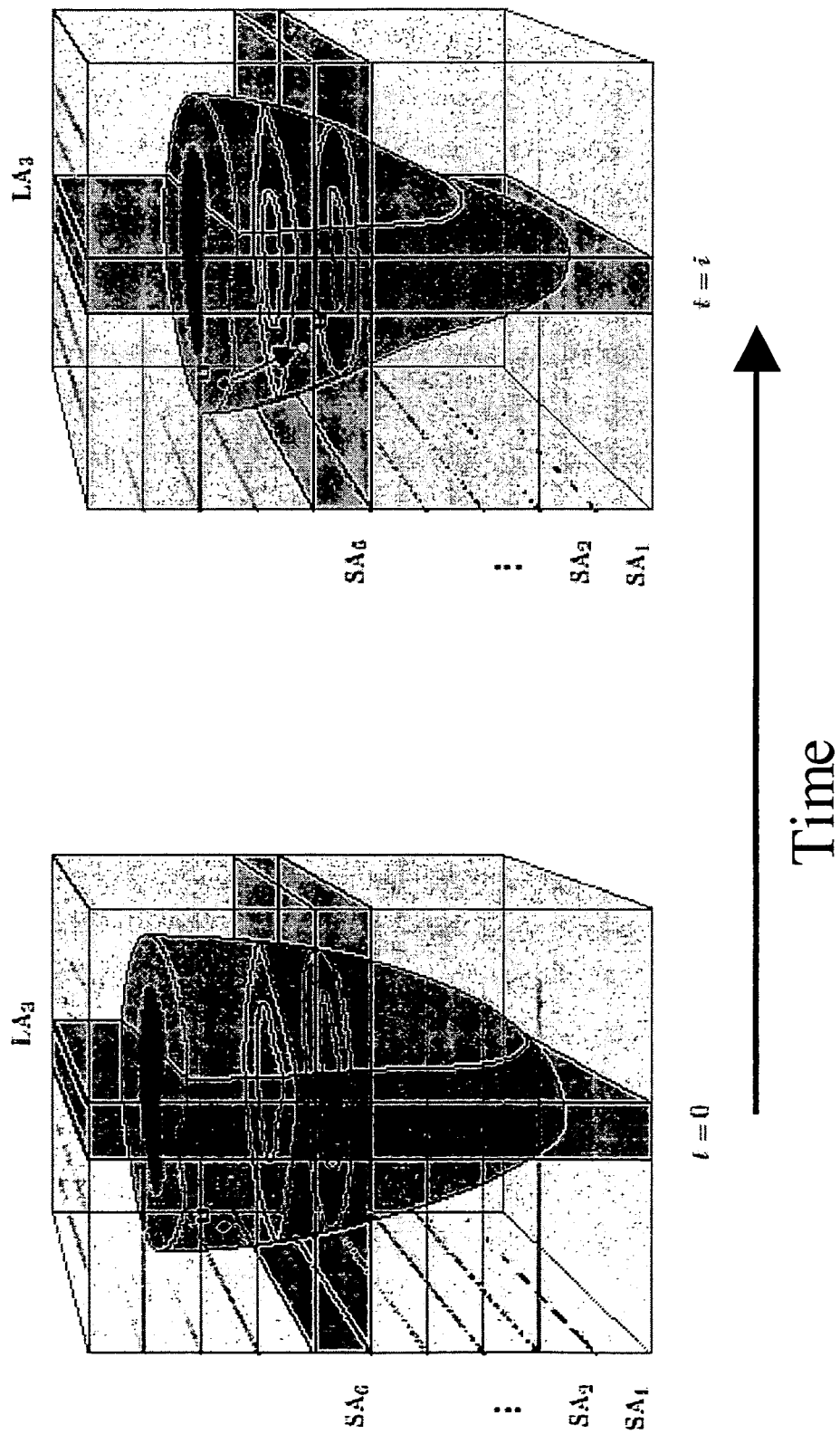
FIG. 75 depicts an embodiment of a pictorial representation of a beginning and end of a cardiac cycle over a time period starting at a diastolic phase of a heart and ending at a systolic phase of a heart.

Delta analysis may be at least partially based on the observation that in a specified time period, typically only portions of the heart demonstrate substantially significant movement relative to other portions of the body depicted in the provided image. In some embodiments, a specified time period may be, for example, greater than about the average cardiac cycle of a human being (e.g., about 800 milliseconds). FIG. 75 depicts an embodiment of a pictorial representation of a beginning and end of a cardiac cycle over a time period, i, starting at a diastolic phase of the heart and ending at a systolic phase of the heart. In some embodiments, a time period may be expanded to ensure capture of a total cardiac cycle. Typically, a patient or subject of an MRI is asked to refrain from breathing as much as possible during an MRI scan, which may help decrease a majority of the motion of the lungs and related organs. Delta analysis is at least partly based on identifying one or more portions of a series of images (taken over a period of time) that demonstrate a significant amount of motion relative to other portions of the image.

As part of a Delta analysis, for a given part of an image (e.g., a point as defined by x and y coordinates of a two dimensional plane and/or an individual pixel in a digital image), an average intensity may be calculated. In some embodiments, an average intensity may be calculated using EQN. 14. An average intensity may be calculated for every part of an image or for a predetermined area of an image for a location (e.g. including all the images at a specific location acquired over time). FIG. 76 depicts an embodiment of an example of a series of MRI images for a location I=2 over a phase. A multi-dimensional image of the calculated average intensity may be constructed by a system, an example of which is depicted in FIG. 77.

$$Average_i(x, y) = \sum_{p=0}^{nPhase} I_{p,i}(x, y) \qquad (14)$$

$$Variance_i(x, y) = \sum_{p=0}^{nPhase} (Average_i(x, y) - I_{p,i}(x, y))^2 \qquad (15)$$

For a given part of an image (e.g., a point as defined by x and y coordinates of a two dimensional plane or an individual pixel in a digital image), a variance may be calculated. The variance may include the standard deviation of the intensity of the part of the image. In some embodiments, an average variance may be calculated using EQN. 15. The variance may be calculated for every part of an image and/or for a predetermined area of an image for a given phase (e.g., time period over which a series of images were obtained). A multi-dimensional image of the calculated variance may be constructed by a system, an example of which is depicted in FIG. 78. The area of FIG. 78 with the greater intensity relative to the surrounding image includes portions of the heart.

Figure 79:
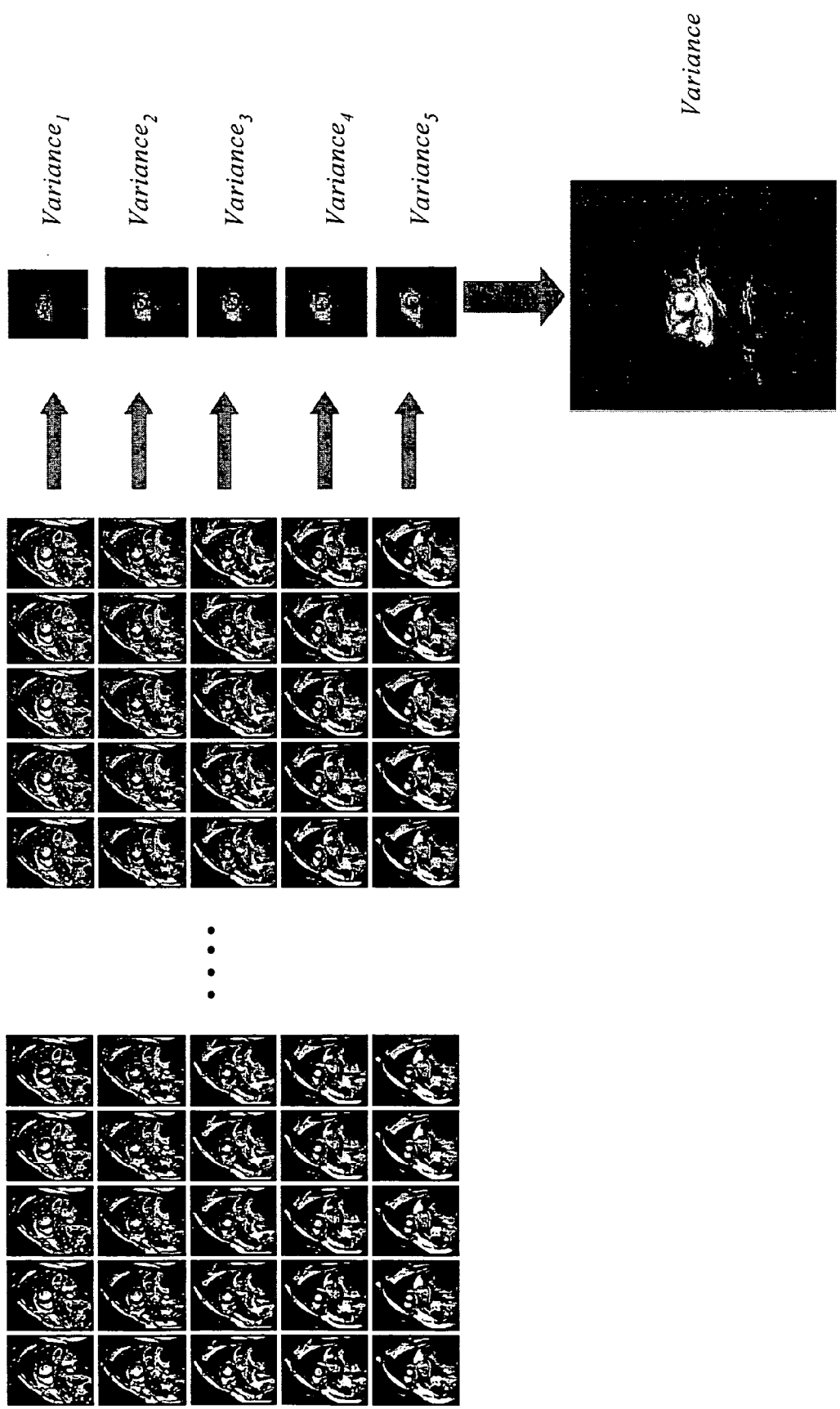
FIG. 79 depicts an embodiment of a multi-dimensional image of the integrated variance matrices.

In some embodiments, a delta analysis may include integrating at least some or all of the calculated variance matrices for all of the parts of the images over a specified time period. Integrating the variance matrices may compensate for areas of the ROI that have little relative movement but are of interest (e.g., the apex of the heart). Integrating the variance matrices may "average out" areas that contain minor artifacts of movement (e.g., artifacts associated with breathing or variance in the skin). In some embodiments, variance matrices may be integrated using EQN. 16. A multi-dimensional image of the integrated variance matrices may be constructed by a system, an example of which is depicted in FIG. 79. FIG. 79 depicts an embodiment of an example of a series of calculated variances of n locations I integrated together into a single image.

$$Variance(x, y) = \sum_{l=0}^{nLocation} Variance_l(x, y) \qquad (16)$$

Figure 80:
FIG. 80 depicts an embodiment of a rectangle located in an integrated variance matrix with the highest gray level.

A rectangle may be employed to locate a portion within the integrated variance matrices with the highest "gray level" (i.e., with the largest amount of relative movement). The shape used may not be limited to a rectangle but other shapes may be employed (e.g., a circle). The size of the rectangle may be predetermined. In some embodiments, the size of the rectangle may be based on an average width and/or height of a human heart. In some embodiments, a particular size rectangle may be chosen based on certain criteria associated with the patient/subject (e.g., age of the patient/subject). It is not necessary to determine the exact size of the heart of the subject, merely to use a rectangle large enough for the heart to fit within. Given the width and height of the heart, the rectangle of the given size with the highest gray level may be located in the variance. In some embodiments, the rectangle may located using EQN. 17. FIG. 80 depicts an embodiment of a rectangle located in an integrated variance matrix with the highest gray level.

$$Rectangle(w, h) = \qquad (17)$$
$$\operatorname{Max}_{x_0 \le ImageWidth-w, y_0 \le ImageHeight-h} \left\{ \sum_{x=x_0}^{x_0+w} \sum_{y=y_0}^{y_0+h} Variance(x, y) \right\}$$

In some embodiments, upon determining a ROI, the segmentation of the ROI may be further constrained prior to performing a segmentation and/or specific transformation (e.g., AAM). For example, a center constrain may be employed to constrain the center of a template in, for example, the AAM to lay in a region based on a number of factors. The factors may include a point or center based on the intersection of the long and short axis of, for example, the heart in the ROI. The long axis may be determined with the assistance of acquisition parameters. The short axis may be determined by analyzing the image using a transformation within the protocol of the AAM. Constraining the segmentation of the ROI around a center calculated for the object to be segmented may increase efficiency and/or reduce errors associated with unmodified AAM.

Figure 81:
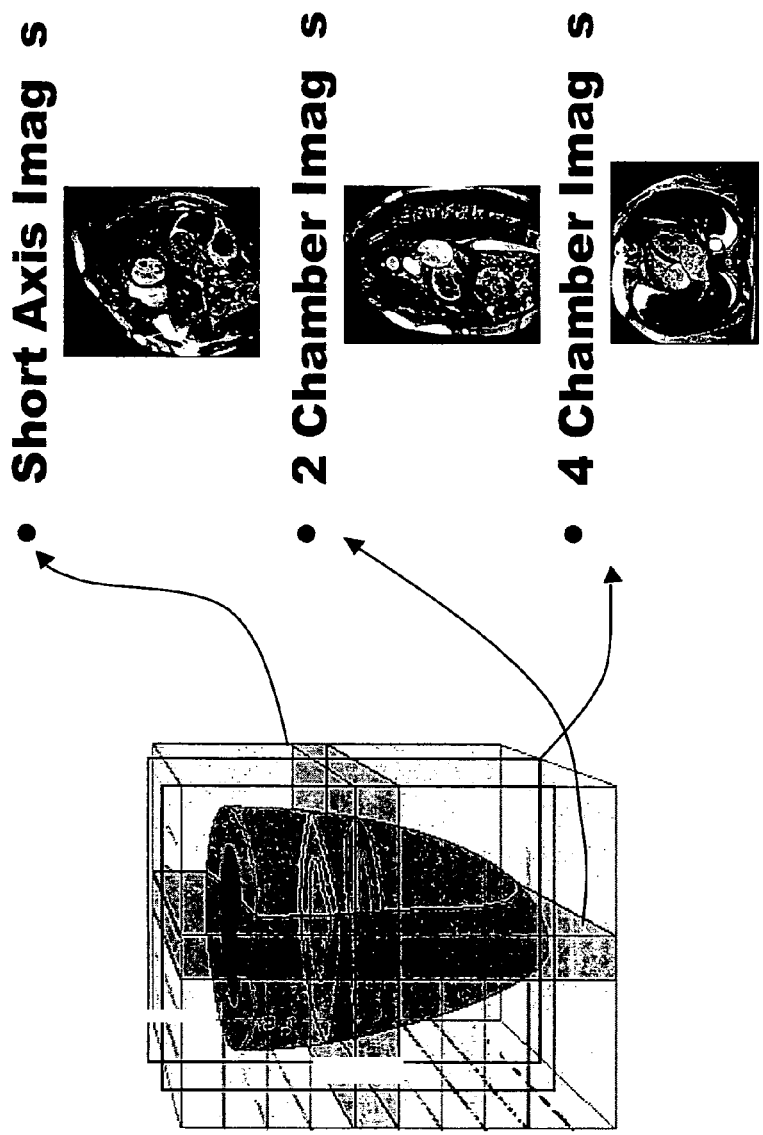
FIG. 81 depicts an embodiment of a pictorial representation of a short axis image, a two chamber image, and a four chamber image.
Figure 82:
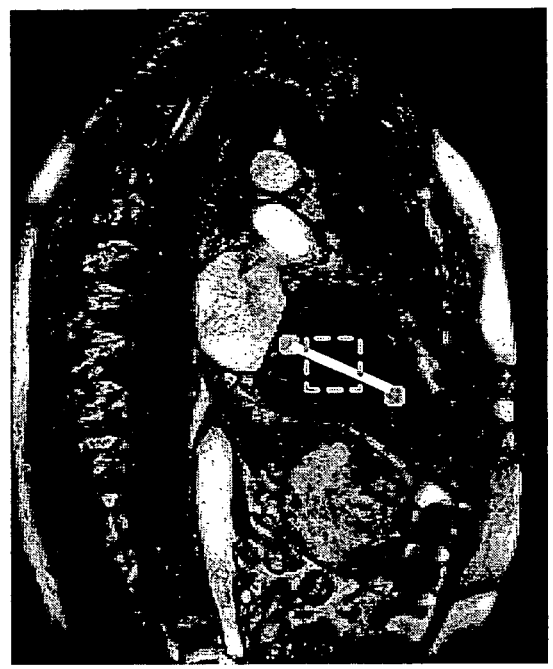
FIG. 82 depicts an embodiment of an example of a long axis of a heart based on two points including one point located about in the middle of a mitral valve and one point at an apex of a left ventricle.
Figure 83:
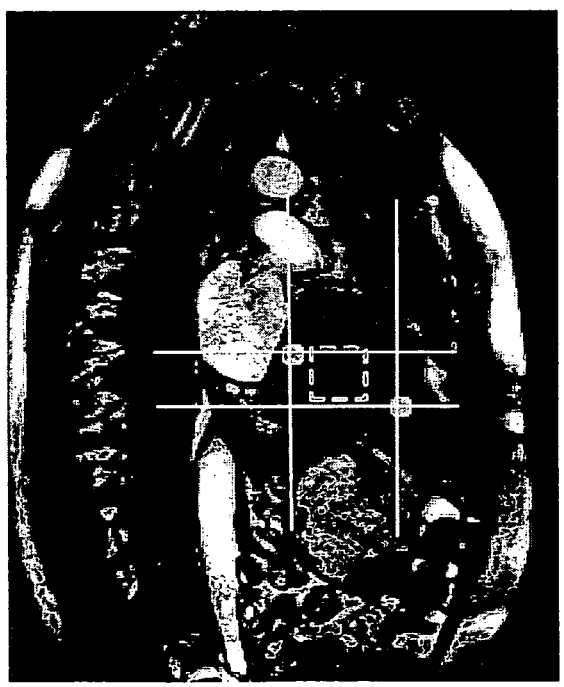
FIG. 83 depicts an embodiment of an example of a rectangle formed from the two points depicted in FIG. 82 used to constrain the AAM method.

The center of the long axis of the heart may be assessed using, for example, data from images of the heart from a short axis image, a two chamber image, and/or a four chamber image. FIG. 81 depicts an embodiment of a pictorial representation of a short axis image, a two chamber image, and a four chamber image. Within the long axis of the heart, the center of the model may be in the middle point between the intersection of the long axis and the short axis of the heart. The long axis may be based on locating at least two points including at least one point located about in the middle of the mitral valve and at least one point one point at the apex of the left ventricle. The point located about in the middle of the mitral valve may be assessed by the intersection of the top point of a two chamber view of the heart and the top point of a four chamber view of the heart and the top point of the short axis view of the heart. The point at the apex of the left ventricle may be assessed by the intersection of a plane within a two chamber view of the heart, a plane within a four chamber view of the heart, and a bottom of the short axis. FIG. 82 depicts an embodiment of an example of the long axis based on two points including one point located about in the middle of the mitral valve and one point at the apex of the left ventricle. In some embodiments, the two points may form the vertices of a rectangle, which may be located within the left ventricle of the heart. The rectangle may be used to constrain the AAM method. FIG. 83 depicts an embodiment of an example of a rectangle formed from the two points depicted in FIG. 82 used to constrain the AAM method.

Figure 84:
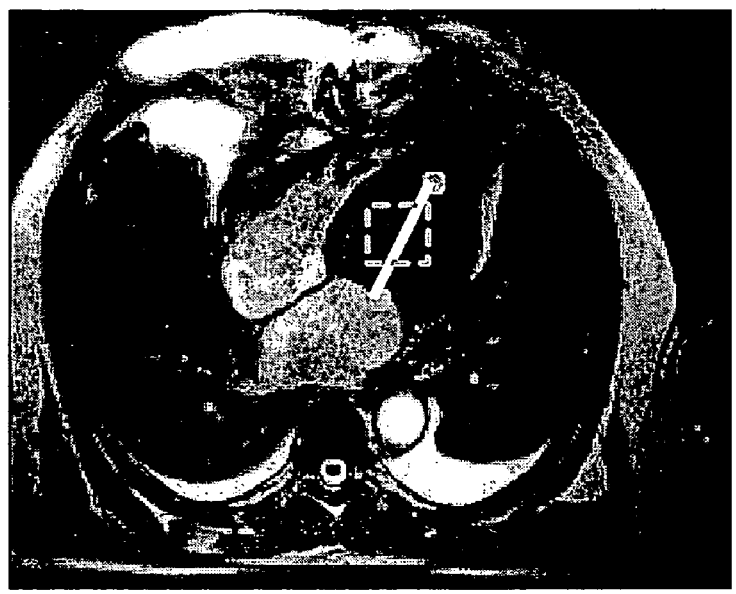
FIG. 84 depicts an embodiment of an example of a short axis of a heart based on two points.
Figure 85:
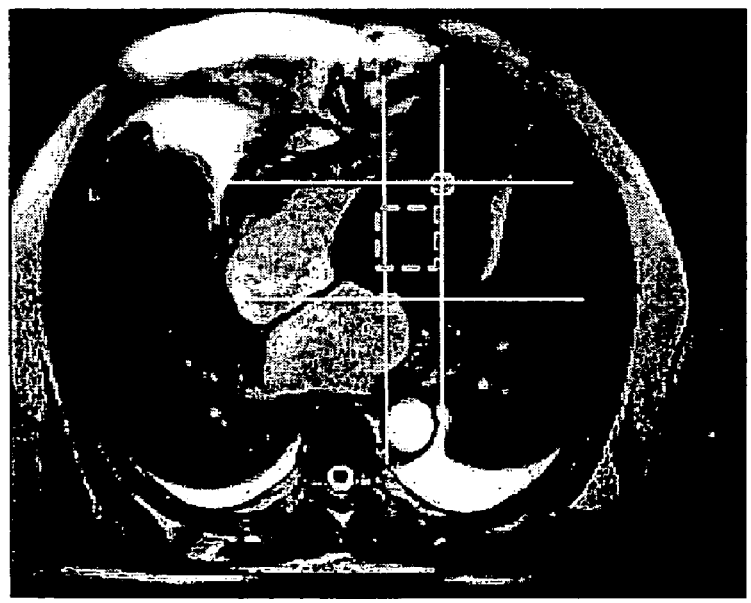
FIG. 85 depicts an embodiment of an example of a rectangle formed from the two points depicted in FIG. 84 used to constrain the AAM method.

A short axis may be assessed by locating at least two points. A first point may be assessed by locating the intersection of three planes including: a plane within a two chamber view of the heart; a plane within a four chamber view of the heart; and a top short axis view. A second point may be assessed by locating the intersection of three planes including: a plane within a two chamber view of the heart; a plane within a four chamber view of the heart; and a last short axis view. FIG. 84 depicts an embodiment of an example of the short axis. In some embodiments, the first and the second points may form the vertices of a rectangle, which may be located within the left ventricle of the heart. The rectangle may be used to constrain the AAM method. FIG. 85 depicts an embodiment of an example of a rectangle formed from the first and second points depicted in FIG. 84 and used to constrain the AAM method.

Figure 86:
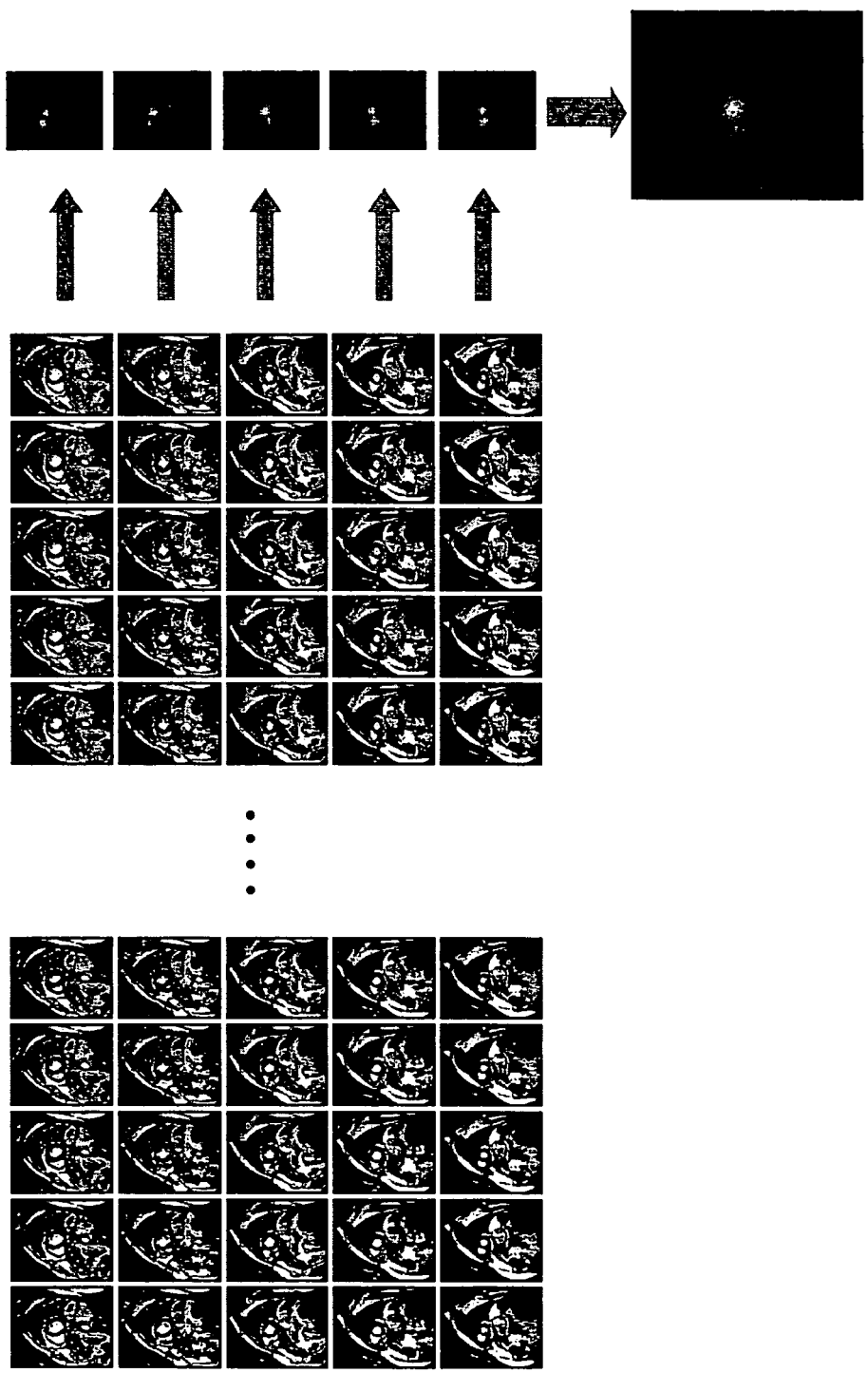
FIG. 86 depicts an embodiment of a representation of the generation of a global Hough transform integrated across location and phase.

In some embodiments, within the short axis of the heart, the center of the model may be assessed using known transforms and/or variations of known methods used in AAM. In some embodiments, known methods may include locating the center within the short axis of the heart using the Hough Transform. The Hough Transform was introduced to locate lines in an image. The Hough Transform may be modified to detect the center of round and/or substantially rounded objects (e.g., ventricles of a heart). The Hough transform may be used to assess the center for each image or slice and integrated across the phase. The Hough transform may be used to assess the center for all of the images or slices within one particular time segment and integrated across the location. Integrating across all locations lessens the intensity of the right ventricle, which is not visible on as many images as the left ventricle. Data from two or more Hough transform integrations may be compiled to generate a global Hough transform for the entire data set. FIG. 86 depicts an embodiment of a representation of the generation of a global Hough transform integrated across location and phase.

Figure 87:
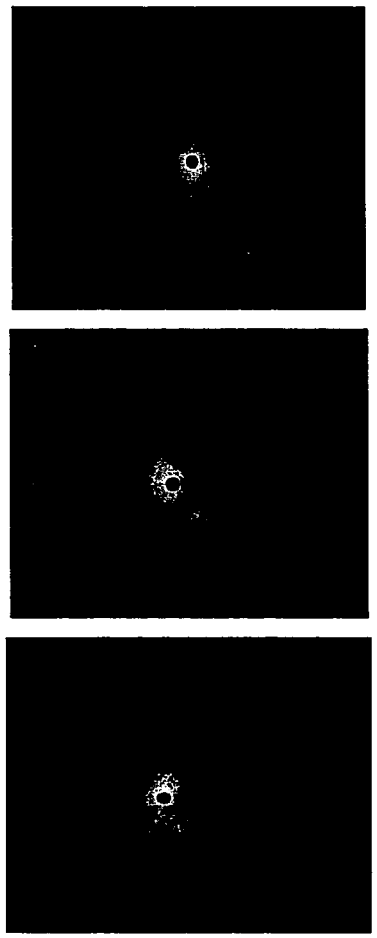
FIG. 87 depicts embodiments of examples of a first approximation of the center of the left ventricle within three locations of the global Hough transform.
Figure 88:
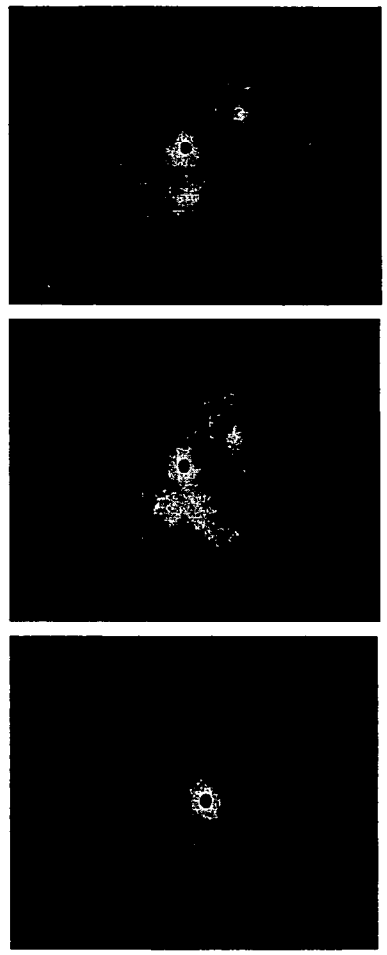
FIG. 88 depicts embodiments of examples of a refined approximation of the center of the left ventricle within three locations of the global Hough transform.
Figure 89:
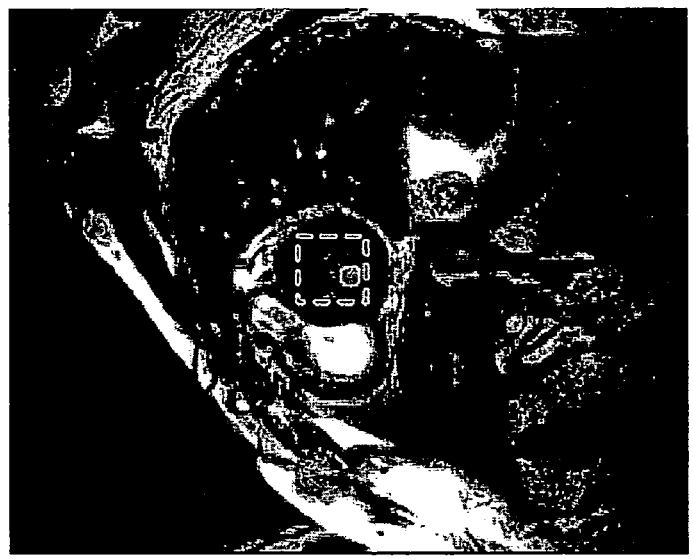
FIG. 89 depicts embodiments of examples of a constrained AAM center (represented by an overlaid square) assessed relative to an assessed center point.
Figure 89:
Figure 89:
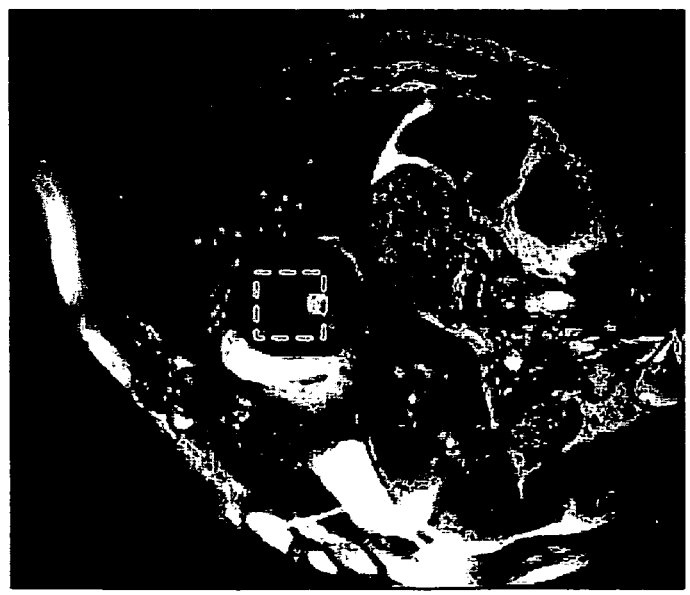

In certain embodiments, results for a Hough transform may be combined with results for a center located for the long axis of a heart. The brightest area closest to the long axis center may be located in the global Hough transform as a first approximation of the center of the left ventricle. FIG. 87 depicts embodiments of examples of a first approximation of the center of the left ventricle within three locations of the global Hough transform. Using the long axis center may assist in differentiating the left ventricle from the right ventricle in the short axis Hough transform center. For each location within the series, the approximation of the center obtained by combining the global Hough transformation with the long axis center is refined by locating the brightest area (e.g., the area with greatest intensity) within each location nearest the approximated center. FIG. 88 depicts embodiments of examples of a refined approximation of the center of the left ventricle within three locations of the global Hough transform. At least two different parameters may be used to locate the brightest area within each image. One parameter may include the intensity of an area relative to the remaining image (for example, focusing on the 10% brightest area within the image). One parameter may include distance from the area to the approximate center. Individual parameters may be weighted relative to one another. In one embodiment, parameters may be weighted equally. In certain embodiments, a plurality of parameters may be used to locate the brightest area in each image. In the short axis of the heart, the AAM's center may be constrained to lay within a small distance of the point located. FIG. 89 depicts embodiments of examples of a constrained AAM center (represented by an overlaid square formed from dotted lines) assessed relative to an assessed center point.

An AAM may contain a statistical model of the shape and gray-level appearance of the object of interest that may generalize to almost any valid example. Matching to an image may involve finding the model parameters that minimize the difference between the image and a synthesized model example, which may be projected into the image. The potentially large number of parameters makes this a difficult problem. Therefore, it may be advantageous to constrain the AAM method and effectively minimize the number of parameters used.

Displacing each model parameter from the correct value can induce a particular pattern in the residuals. In a training phase, the AAM learns a linear model of the relationship between parameter displacements and the induced residuals. During search, the AAM measures the residuals and uses this model to correct the current parameters, thus leading to a better fit. A good overall match may be obtained in a few iterations, even from poor starting estimates.

Using AAM, a system may learn what is a left ventricle (e.g., based on contours). It may be more efficient to place an AAM matching algorithm in a statistical framework and allow extra constraints to be applied. Effectively, the learning phase of the AAM method may be modified to increase reliability and accuracy of the model matching during the search phase of AAM. In certain embodiments, extra constraints may come from user input. Extra constraints may be automatically generated using other methods such as some of the methods described herein. In some embodiments, the point intersection between long and short axis may be used to constrain the AAM method during the learning phase to assist the algorithm in learning the relative location of the contour of the left ventricle from the intersection points.

In some embodiments, a color gradient-based image processing method may be applied to a grayscale cardiac magnetic resonance image before segmentation is attempted. Image masks may be created utilizing such a method to allow greater accuracy in further image segmentation processes.

An 8-bit grayscale image may be thought of as having pixels with equal red, green, and blue values that range from, for example, 0 to 255. A color gradient may be applied to these values.

Figure 90:
FIG. 90 depicts an embodiment of a color gradient applied to a grayscale MRI image followed by applying a filter.

Once such a gradient has been applied to a grayscale image, the images red, green and blue channels may be split into separate grayscale images. Each pixel may take a gray value based on either the red, green, or blue pixel value. FIG. 90 depicts an embodiment of a color gradient applied to a grayscale MRI image followed by applying a filter. FIG. 90 depicts an embodiment of a grayscale MRI image (labeled "Original" in FIG. 90) to which a color gradient has been applied (labeled "Gradient Mapped" in FIG. 90) to transform the grayscale image to a color image. Note within FIG. 90 the color image is depicted in black and white. A filter may be applied to the Gradient Mapped image to remove everything from the image except, for example, any pixels falling within the range assigned to red. The predetermined range assigned to red may be rescaled. The predetermined range assigned to red may be rescaled to, for example, the original scale (e.g., 0 to 255). Upon rescaling, the filtered image may be converted back to grayscale with the rescaled range representing shades of gray from white to black to create a filtered image (labeled "Red Channel" in FIG. 90). Different filters may be used to remove different ranges (i.e., colors) to assist in providing greater clarity to different parts of the original image. Providing greater clarity to a portion of an image may facilitate, for example, segmentation and/or mapping of the image.

Figure 91:
FIG. 91 depicts an embodiment of a color gradient applied to a grayscale MRI image of an apical portion of a heart followed by applying a filter.

This process may be a simple way of implementing a complex band pass filter. This filter may be shown to work even in the apical regions of the left ventricle where it is generally difficult to find edges in images. FIG. 91 depicts an embodiment of a color gradient applied to a grayscale MRI image of an apical portion of a heart followed by applying a filter.

Figure 92:
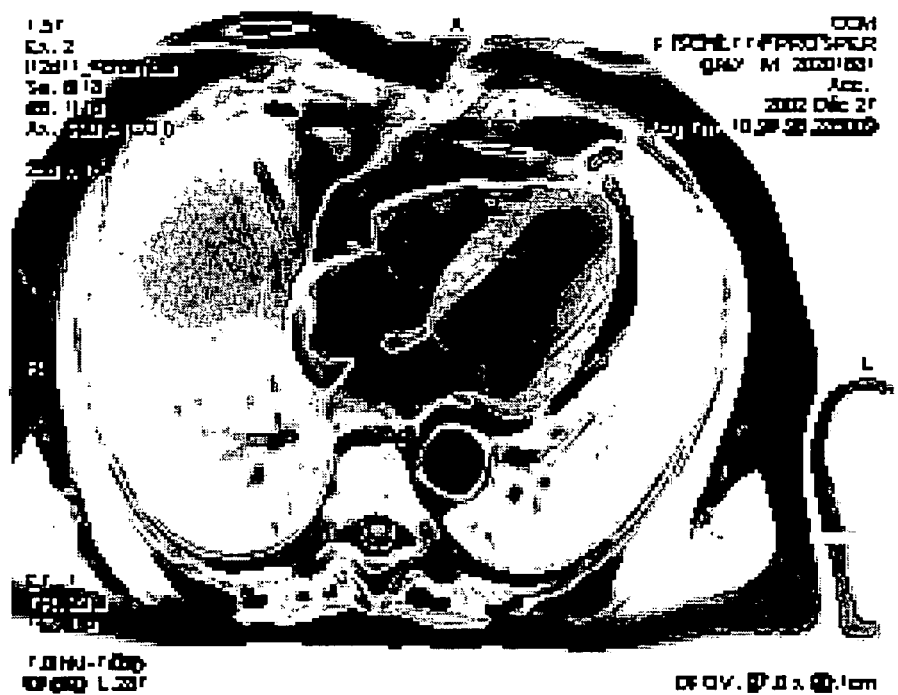
FIG. 92 depicts an embodiment of a color gradient processed image with edge-detection.
Figure 93:
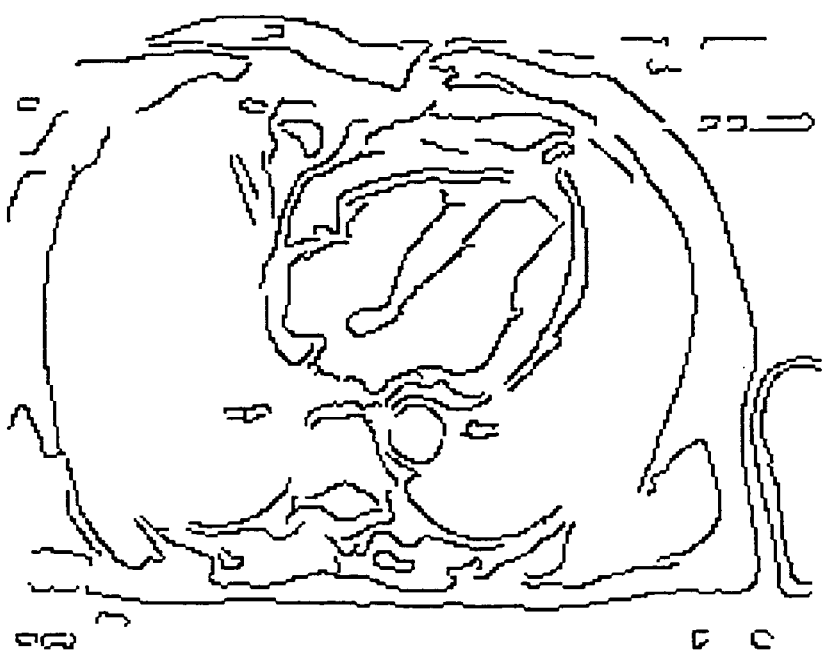
FIG. 93 depicts an embodiment of a color gradient processed image with edge-detection depicting only the edges.

In some embodiments, after processing an image, an edge detection method may be implemented. An edge detection method may be able to find edges in these processed images. Once these edges have been found, automatic region of interest calculation and interpolation for missing contour portions may provide an accurate method of segmenting a portion of the heart (e.g., the left ventricle). FIG. 92 depicts an embodiment of a color gradient processed image with edge-detection. FIG. 93 depicts an embodiment of a color gradient processed image with edge-detection depicting only the edges.

In recent years, image guided surgery has become more and more common. Image guides surgery has become more common because of the ability of a user to view internal images of a patient's anatomy and pre-plan a medical operation. Pre-acquired images of the anatomical body (e.g., a heart) may be used to plan the course of the medical procedure, whether the medical procedure is diagnostic, therapeutic, and/or surgical in nature. Pre-acquired images may be used to create models of a portion of the body. The models may be used to determine an optimized diagnosis and/or treatment of the portion of the body. The pre-acquired images and/or model may also be used during the medical procedure for orientation of the user with respect to the internal anatomy of the patient.

The images of a patient's external or internal anatomy used in image guided surgery may be generated by a number of imaging methods, including, but not limited to, computerized tomography (CT), magnetic resonance imaging (MRI), video, ultrasound, and X-rays. Images may also be captured using angiography, single photon emission computer tomography, and positron emission tomography (PET). In certain embodiments, at least two, and generally more than two, images of the patient's internal anatomy are generated. The images may be captured such that the relative position of the images is known. The images, along with information indicating the relative position of the images, may be stored in a data-base to create a model based on the pre-acquired images and corresponding to the anatomical body of the patient at the time the images were captured.

This model may be used for a number of purposes including, but not limited to, diagnosis or pre-planning the medical procedure and/or treatment. A method for creating such a model is described herein.

Users may pre-plan the course of a medical procedure by marking, either manually or electronically, on the model the course of the medical procedure. A computer system may propose a treatment plan. The treatment plan may be based on minimal or no input from the user. Proposed treatment plans may include models with markings outlining a surgical procedure. The markings may indicate areas of interest, objects of concern, as well as proposed cuts or drilling locations and orientations, and locations that may be irradiated with specific types of radiation for diagnostic or therapeutic procedures. During the medical procedure, the user may refer to the markings on the images to assist in performing the procedure.

Prior art imaging devices may project a representation of the instrument or tool being used by the user onto the pre-acquired images during a medical procedure. The representation corresponds to the position of the actual instrument or tool with respect to the patient. By viewing the position of the representation of the instrument or tool with respect to the data-base body of pre-acquired images, the user may extrapolate the position of the actual probe or instrument with respect to the internal anatomy of the patient. In addition, the user may simultaneously follow the pre-planned markings on the pre-acquired images. However, unnecessary error may be introduced in this process and the process may not provide a very accurate guide to the user. The user may become confused because the pre-acquired images and/or representation of the instrument or tool may appear unrealistic and/or unrepresentative of what is actually occurring before him.

Errors occurring because of the superposition of the position of the represented tool and the pre-acquired image may result in possibly disastrous effects. There is a risk that a user may not notice that the user has struck, or could strike, a "critical structure" within the patient or subject. Critical structures may include an organ or blood vessel, which if struck may critically or severely damage the patient. This possibility is compounded by the fact that several imaging techniques may not provide detailed images of critical structures such as organs or blood vessels.

A disadvantage of the prior art imaging systems is that all pre-planned markings made by the user are located on the pre-acquired images. Accordingly, in order to use the pre-planned markings, the user may have to constantly refer to the images and orient the images and pre-planned markings to the anatomical body during the course of the medical procedure.

In certain embodiments, a method and system may facilitate image guided surgery by superimposing portions of a patient specific model on at least one portion of an image. The model may include portions of markings and/or details from a proposed treatment (e.g., a surgical procedure). The image may include a substantially live feed image and/or video. Live feed images may include a slight delay due to the superimposition process. The delay may be imperceptible under normal operating conditions (e.g., under operating room conditions).

The model may have been derived from images provided to a computer system using a method as outlined in, for example, FIG. 3. The method may assess a position of one or more heart features during the creation of the model. A position of one or more similar heart features may be assessed in the live feed image. The position of a heart feature within the model may be compared to the similar heart feature within the live feed image. Comparing the two positions may allow for a more accurate superposition of the model and the live feed image. Superimposing these two images may allow the user to more accurately carry out the proposed surgical procedure. The superimposed images may allow the user to better orient himself and more quickly and easily identify features within the heart.

In some embodiments, a model of the heart may include markings to better guide a user during a surgical procedure. Markings may include color gradients, lines, grids, arrows, and/or specific text. In certain embodiments, the model and the markings thereon may automatically update as the treatment progresses. For example, after an incision has been made in heart tissue during a surgical procedure, the model may automatically update to reflect the incision. Updating the model may include displaying new markings depicting a next step in a surgical procedure. This type of image guided surgery may take some or all of the guess work out of heart surgery, which currently is thought of more as an art than a science. Currently, results of a surgical procedure performed on a heart are highly dependent on the skill and experience of a surgeon performing the operation. Image guided surgery may allow the user to optimize a treatment of a heart before performing the procedure and image guided surgery may assist the user in carrying out the procedure. Models used in combination with image guided surgery may assist a user in producing more consistent results.

In some embodiments, a model and markings thereon may automatically update as a treatment progresses. Automatically updating the model may include assessing relevant data (e.g., ejection fraction) associated with assessing a state of the heart during a procedure. The state of the heart may be assessed using relevant data gathered from the live feed image and/or from other medical diagnostic instruments.

In some embodiments, a method and system may facilitate image guided surgery by projecting onto the anatomical body during the medical procedure any markings made onto the data-base body of pre-acquired images.

In this patent, certain U.S. patents, U.S. patent applications, and/or other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of assessing a state of human heart tissue, comprising:
    providing to a computer system a plurality of images of heart tissue, wherein at least one of the images comprises the heart in a substantially expanded condition, and wherein at least one of the images comprises the heart in a substantially contracted condition;
    creating a model of at least a portion of a wall of a left ventricle of the heart using the computer system, wherein the model comprises the left ventricle in at least an end-systolic state and an end-diastolic state;
    assessing a movement of one or more parts of the wall model between the end-systolic state and the end-diastolic state;
    assessing a transmurality of one or more parts of the wall model;
    comparing the movement to the transmurality to assess a ratio of recoverable heart tissue verses nonrecoverable heart tissue; and
    comparing the ratio to a predetermined number to assess a state of the heart and an optimal treatment of the heart.

2. The method of claim 1, wherein the predetermined number comprises an average of a plurality of normal hearts.

3. The method of claim 1, further comprising displaying the state of the heart visually within the model.

4. The method of claim 1, further comprising displaying the state of the heart visually within the model using a color gradient.

5. The method of claim 1, further comprising matching at least one part of the wall of the model in the end-systolic state with a corresponding part of the wall of the model in the end-diastolic state.

6. The method of claim 1, further comprising matching at least one part of the wall of the model in the end-systolic state with a corresponding part of the wall of the model in the end-diastolic state using one or more normals associated with the parts.

7. The method of claim 1, further comprising determining a number of parts in which the movement of each part is greater than a range from the predetermined number.

8. The method of claim 1, further comprising:
    determining a number of parts in which the movement of each part is greater than a range from the predetermined number; and
    dividing the number of parts by a total number of parts.

9. The method of claim 1, wherein the assessed movement comprises movement towards a centerline of the heart.

10. The method of claim 1, wherein the assessed movement comprises wall thickness variation.

11. The method of claim 1, wherein at least one part with assessed movement comprises a point in the wall.

12. The method of claim 1, wherein at least one part with assessed movement comprises a plurality of points in the wall.

13. The method of claim 1, further comprising displaying the state of the heart visually with a plurality of colors, wherein the colors represent kinetic properties of at least one part.

14. The method of claim 1, further comprising displaying the state of the heart visually with a plurality of colors, wherein each of the colors represent different kinetic properties.

15. The method of claim 1, further comprising assessing kinetics of at least a portion of the heart tissue.

16. The method of claim 15, further comprising identifying hyper-kinetic tissue from the assessed kinetics.

17. The method of claim 15, further comprising identifying hyper-kinetic tissue from the assessed kinetics, wherein hyper-kinetic tissue comprises tissue with movement of two or more standard deviations greater than the predetermined number.

18. The method of claim 15, further comprising identifying akinetic tissue from the assessed kinetics, wherein akinetic tissue comprises tissue with movement of two or more standard deviations less than the predetermined number.

19. The method of claim 15, further comprising identifying normal tissue from the assessed kinetics.

20. The method of claim 15, further comprising identifying normal tissue from the assessed kinetics, wherein normal tissue comprises tissue with movement that deviates in an amount that is from zero to about two standard deviations from the predetermined number.

21. The method of claim 15, further comprising identifying diskinetic tissue from the assessed kinetics.

22. The method of claim 15, further comprising identifying diskinetic tissue from the assessed kinetics, wherein diskinetic tissue comprises tissue with movement away from a centerline of the heart.

23. The method of claim 15, further comprising identifying akinetic tissue from the assessed kinetics.

24. The method of claim 23, further comprising assessing tissue suitable for revascularization, wherein tissue suitable for revascularization comprises viable, akinetic tissue.

25. The method of claim 23, further comprising assessing tissue suitable for revascularization, wherein tissue suitable for revascularization comprises viable, akinetic tissue with an akinetic area greater than a predetermined akinetic area.

26. The method of claim 23, further comprising assessing tissue suitable for revascularization, wherein tissue suitable for revascularization comprises viable, akinetic tissue with a non-viable area less than a predetermined non-viable area, wherein the non-viable area is assessed from the plurality of images.

27. The method of claim 23, further comprising assessing tissue suitable for revascularization, wherein tissue suitable for revascularization comprises viable, akinetic tissue with an akinetic area greater than a predetermined akinetic area and akinetic tissue with a non-viable area less than a predetermined non-viable area, wherein the non-viable area is assessed from the plurality of images.

28. The method of claim 1, wherein the model comprises a three-dimensional model.

29. The method of claim 1, further comprising assessing if a heart is a potential candidate for ventricular reconstruction, wherein the heart is a potential candidate for ventricular reconstruction if the heart comprises at least a predetermined amount of non-viable tissue area, and wherein the non-viable tissue area is assessed from the plurality of images.

30. The method of claim 1, further comprising assessing if a heart is a potential candidate for ventricular reconstruction, wherein the heart is a potential candidate for ventricular reconstruction if the heart comprises at least a predetermined amount of non-viable tissue volume, and wherein the non-viable tissue volume is assessed from the plurality of images.

31. The method of claim 1, further comprising assessing if a heart is a potential candidate for ventricular reconstruction, wherein the heart is a potential candidate for ventricular reconstruction if the heart comprises at least a predetermined amount of non-viable tissue mass, and wherein the non-viable tissue mass is assessed from the plurality of images.

32. The method of claim 1, further comprising assessing if a heart is a potential candidate for ventricular reconstruction, wherein the heart is a potential candidate for ventricular reconstruction if the heart comprises at least a predetermined amount of non-viable tissue and at least a predetermined amount of akinetic tissue.

33. The method of claim 1, further comprising assessing if a heart is a potential candidate for ventricular reconstruction, wherein the heart is a potential candidate for ventricular reconstruction if the heart comprises at least a predetermined amount of non-viable tissue and at least a predetermined end diastolic volume.

34. The method of claim 1, further comprising assessing if a heart is a potential candidate for ventricular reconstruction, wherein the heart is a potential candidate for ventricular reconstruction if the heart comprises at least a predetermined amount of non-viable tissue and at least a predetermined transmurality.

35. The method of claim 1, further comprising assessing if a heart is a potential candidate for ventricular reconstruction, wherein the heart is a potential candidate for ventricular reconstruction if the heart comprises an ejection fraction less than a predetermined ejection fraction.

36. The method of claim 1, further comprising assessing if a heart is a potential candidate for ventricular reconstruction, wherein the heart is a potential candidate for ventricular reconstruction if the heart comprises an ejection fraction less than about 35%.

37. The method of claim 1, further comprising assessing if a heart is a potential candidate for mitral valve repair, wherein the heart is a potential candidate for mitral valve repair if the heart comprises at least a selected papillary muscle distance, at least a selected papillary muscle angle, and at least a selected amount of mitral regurgitation.

38. The method of claim 1, further comprising assessing if a heart is a potential candidate for mitral valve repair, wherein the heart is a potential candidate for mitral valve repair if the heart comprises at least a selected papillary muscle distance.

39. The method of claim 1, further comprising assessing if a heart is a potential candidate for mitral valve repair, wherein the heart is a potential candidate for mitral valve repair if the heart comprises at least a selected papillary muscle angle.

40. The method of claim 1, further comprising assessing if a heart is a potential candidate for mitral valve repair, wherein the heart is a potential candidate for mitral valve repair if the heart comprises at least a selected amount of mitral regurgitation.

\* \* \* \* \*